United States Patent
Takada et al.

(10) Patent No.: US 10,885,629 B2
(45) Date of Patent: Jan. 5, 2021

(54) MEDICAL IMAGE PROCESSING APPARATUS, MEDICAL IMAGE PROCESSING METHOD, MEDIUM, AND MEDICAL IMAGE PROCESSING SYSTEM

(71) Applicants: Masahiro Takada, Tokyo (JP); Akira Kinoshita, Tokyo (JP); Kazuya Niyagawa, Kanagawa (JP)

(72) Inventors: Masahiro Takada, Tokyo (JP); Akira Kinoshita, Tokyo (JP); Kazuya Niyagawa, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 83 days.

(21) Appl. No.: 16/250,322

(22) Filed: Jan. 17, 2019

(65) Prior Publication Data

US 2019/0236777 A1 Aug. 1, 2019

(30) Foreign Application Priority Data

Jan. 31, 2018 (JP) .................. 2018-015941
Jun. 12, 2018 (JP) .................. 2018-111788

(51) Int. Cl.
*G06T 7/00* (2017.01)
*G06T 11/60* (2006.01)
*G06T 7/77* (2017.01)

(52) U.S. Cl.
CPC ............ *G06T 7/0012* (2013.01); *G06T 7/77* (2017.01); *G06T 11/60* (2013.01); *G06T 2207/10088* (2013.01); *G06T 2207/10116* (2013.01); *G06T 2207/20076* (2013.01); *G06T 2207/30012* (2013.01)

(58) Field of Classification Search
CPC .......... G06T 7/0012; G06T 7/77; G06T 11/60
See application file for complete search history.

(56) References Cited

U.S. PATENT DOCUMENTS

| 10,043,111 | B2* | 8/2018 | Akahori | .................... G06T 7/11 |
| 2009/0226062 | A1* | 9/2009 | Nakamura | .............. G06F 16/51 |
| | | | | 382/128 |
| 2013/0131486 | A1* | 5/2013 | Copf | ................... A61F 2/30942 |
| | | | | 600/407 |
| 2015/0248593 | A1* | 9/2015 | Nakashima | .......... A61B 6/5217 |
| | | | | 382/131 |

(Continued)

FOREIGN PATENT DOCUMENTS

| JP | 2016-168166 | 9/2016 |
| JP | 6218569 | 10/2017 |

*Primary Examiner* — Md K Talukder
(74) *Attorney, Agent, or Firm* — IPUSA, PLLC

(57) ABSTRACT

A medical image processing apparatus includes a memory; and at least one processor configured to execute detecting one or more vertebral bodies and one or more intervertebral disks in a medical image; labeling each part satisfying a predetermined condition among the one or more vertebral bodies and the one or more intervertebral disks detected by the detecting; interpolating a vertebral body or an intervertebral disk in a case where the one or more vertebral bodies and the one or more intervertebral disks detected by the detecting do not include the vertebral body or the intervertebral disk that satisfies the predetermined condition; and executing the labeling also for the vertebral body or the intervertebral disk interpolated by the interpolating.

19 Claims, 48 Drawing Sheets

(56) References Cited

U.S. PATENT DOCUMENTS

| | | | |
|---|---|---|---|
| 2015/0260814 A1* | 9/2015 | Sakurai | A61B 5/055 |
| | | | 324/322 |
| 2016/0089074 A1* | 3/2016 | Wang | G16H 50/30 |
| | | | 600/407 |
| 2016/0267655 A1* | 9/2016 | Akahori | G06K 9/6267 |
| 2019/0005660 A1* | 1/2019 | Kinoshita | A61B 6/5247 |
| 2019/0236777 A1* | 8/2019 | Takada | G06T 11/60 |
| 2019/0336097 A1* | 11/2019 | Bregman-Amitai | G06K 9/627 |
| 2020/0008702 A1* | 1/2020 | Yokosawa | G01R 33/4833 |
| 2020/0058098 A1* | 2/2020 | Hirakawa | G06T 3/4053 |
| 2020/0069243 A1* | 3/2020 | Matsumoto | A61B 5/1071 |

* cited by examiner

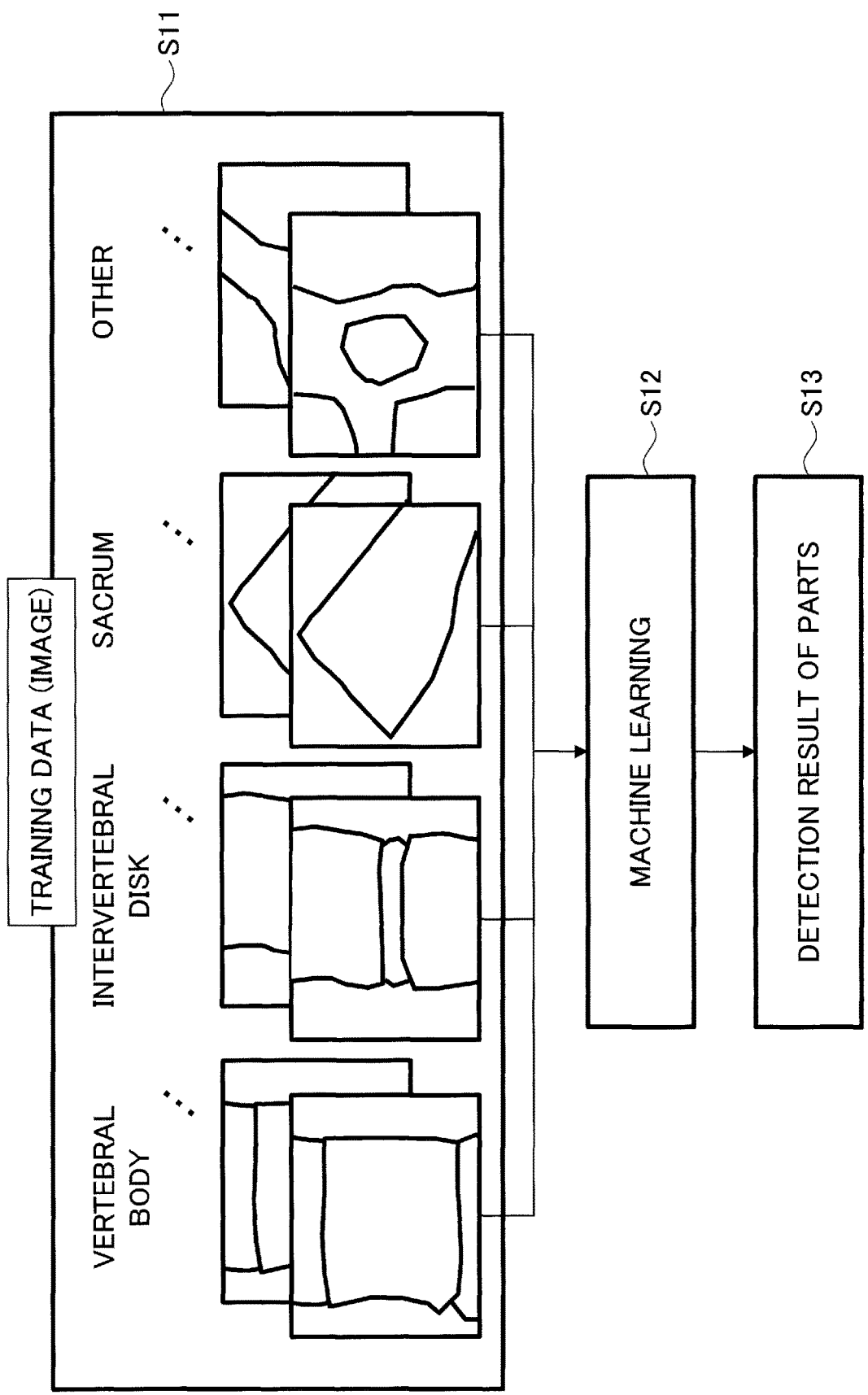

MEDICAL IMAGE PROCESSING APPARATUS, MEDICAL IMAGE PROCESSING METHOD, MEDIUM, AND MEDICAL IMAGE PROCESSING SYSTEM

BACKGROUND OF THE INVENTION

1. Field of the Invention

The present disclosure relates to a medical image processing apparatus, a medical image processing method, a medium, and a medical image processing system.

2. Description of the Related Art

Conventionally, from a medical image obtained by a medical image diagnostic device such as an X-ray CT device, an MRI device (magnetic resonance device), or the like, in order to determine an abnormal part and to align the position, parts of the body such as vertebrae, intervertebral disks, sacrums, and the like are detected to assign labels to these parts.

For example, a method has been proposed for executing labeling on an MRI image while estimating the positions of vertebral bodies and intervertebral disks.

However, medical images to be processed may often include unclear vertebral bodies, with which it may be difficult to detect vertebral bodies in such medical images. In particular, in the case where the medical image is an X-ray image, the vertebral bodies tend to be unclear. Also, since an intervertebral disk is not imaged to have a disk form in an X-ray image, in the case where the medical image is an X-ray image, intervertebral disks cannot be detected. Furthermore, if an intervertebral disk has been compressed to become thinner than a normal one, the intervertebral disk may look unclear even in an MRI image or the like. The conventional method of executing labeling on the MRI image has been targeted at clear images in which parts are clear enough to be detected, and is not capable of estimating the positions of vertebral bodies and intervertebral disks in the case of the images of the vertebral bodies and intervertebral disks being unclear.

As such, according to the conventional techniques, it has been often the case that some of the parts included in a medical image cannot be detected, and hence, labeling cannot be executed appropriately.

SUMMARY OF THE INVENTION

According to an aspect, a medical image processing apparatus includes a memory; and at least one processor configured to execute detecting one or more vertebral bodies and one or more intervertebral disks in a medical image; labeling each part satisfying a predetermined condition among the one or more vertebral bodies and the one or more intervertebral disks detected by the detecting; interpolating a vertebral body or an intervertebral disk in a case where the one or more vertebral bodies and the one or more intervertebral disks detected by the detecting do not include the vertebral body or the intervertebral disk that satisfies the predetermined condition; and executing the labeling also for the vertebral body or the intervertebral disk interpolated by the interpolating.

BRIEF DESCRIPTION OF DRAWINGS

FIG. 13A is a flowchart (first example) illustrating a process of learning and detection executed by a detector;

DETAILED DESCRIPTION OF THE EMBODIMENTS

In the following, example embodiments in the present disclosure will be described in detail. Note that the present disclosure is not limited to the following example embodiments at all and can be implemented with appropriate modification within the scope of the object in the present disclosure.

According to the disclosed techniques, it is possible to appropriately execute labeling on a medical image even when an unclear part is included.

Figure 1:
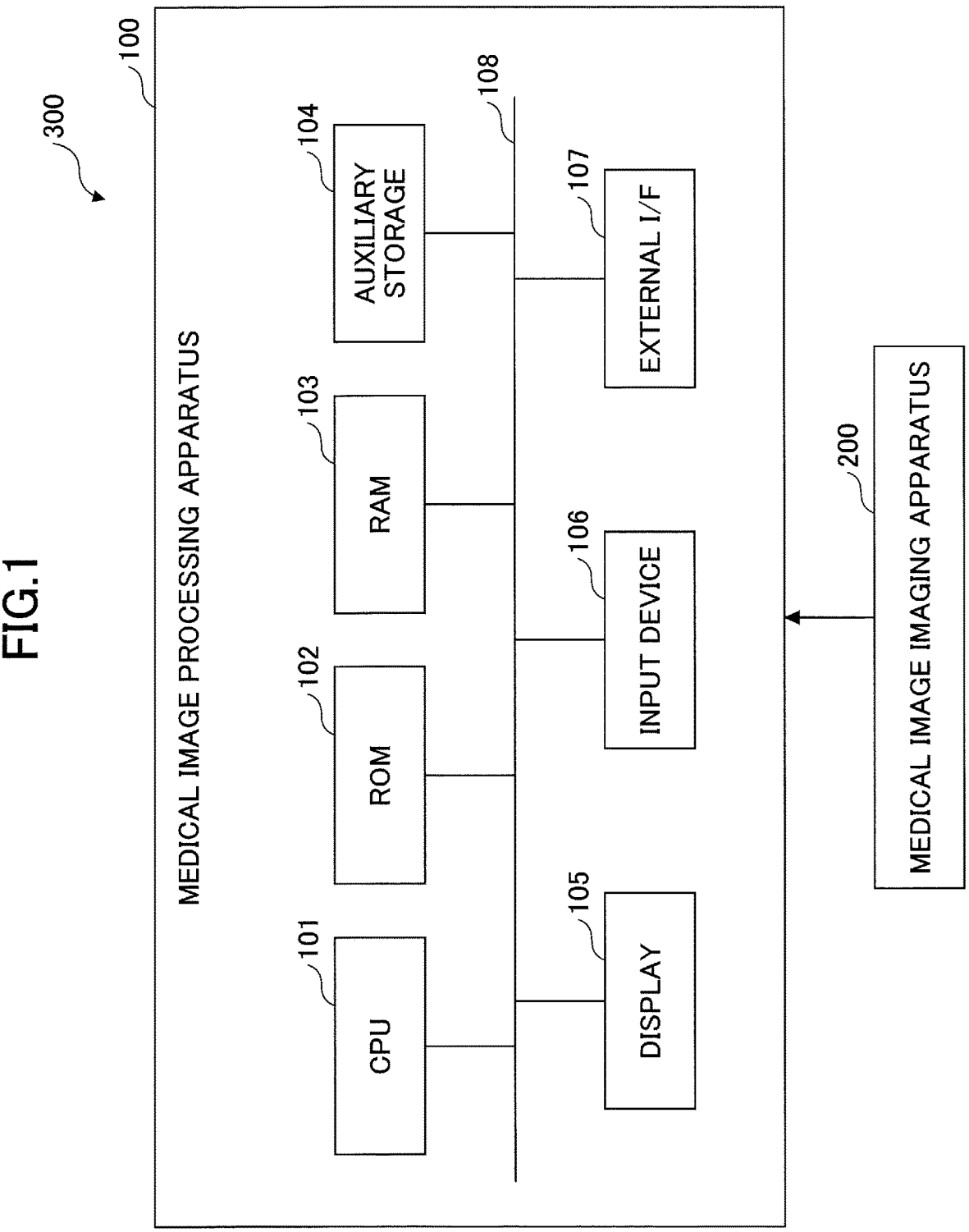
FIG. 1 is a diagram illustrating a medical image processing system according to an example embodiment in the present disclosure.

FIG. 1 is a diagram illustrating a medical image processing system according to an example embodiment in the present disclosure. The medical image processing system 300 includes a medical image processing apparatus 100 and a medical image capturing apparatus 200.

The medical image capturing apparatus 200 captures an X-ray image (X-ray picture) of a subject, and includes, for example, a flat panel detector (FPD). The medical image capturing apparatus 200 may capture an MRI (Magnetic Resonance Imaging) image by MRI. The medical image processing apparatus 100 processes medical image data such as a medical image captured by the medical image capturing apparatus 200.

The medical image processing apparatus 100 includes a CPU (Central Processing Unit) 101, a ROM (Read-Only Memory) 102, and a RAM (Random Access Memory) 103. The CPU 101, the ROM 102, and the RAM 103 constitute a so-called computer. The medical image processing apparatus 100 includes an auxiliary storage 104, a display 105, an input device 106, and an external interface (I/F) 107. These components of the medical image processing apparatus 100 are mutually connected via a bus 108.

The CPU 101 executes various programs (e.g., a medical image processing program) stored in the auxiliary storage 104.

The ROM 102 is a nonvolatile main memory device. The ROM 102 stores various programs, data, and the like necessary for the CPU 101 to execute various programs stored in the auxiliary storage 104. Specifically, the ROM 102 stores a boot program such as BIOS (Basic Input/Output System) and/or EFI (Extensible Firmware Interface).

The RAM 103 is a volatile main memory device such as a DRAM (Dynamic Random Access Memory) or an SRAM (Static Random Access Memory). The RAM 103 functions as a work area on which the various programs stored in the auxiliary storage 104 are loaded when executed by the CPU 101.

The auxiliary storage 104 is an auxiliary storage device to store various programs executed by the CPU 101, and various items of data generated by the CPU 101 when executing the various programs.

The display 105 displays a medical image to which labeling has been applied, or the like. The input device 106 includes a mouse, a keyboard, or both of these, and is used by a doctor or the like to input various commands (data selection command, superimposed display command, etc.) into the medical image processing apparatus 100. The external I/F 107 includes, for example, a communication device for communicating with the medical image capturing apparatus 200, into which a medical image captured by the medical image capturing apparatus 200 is input. The external I/F 107 may include a slot for an external recording medium, and a medical image may be obtained from an external recording medium such as an IC card, a flexible disk, a CD, a DVD, an SD memory card, a USB memory, or the like.

Figure 2:
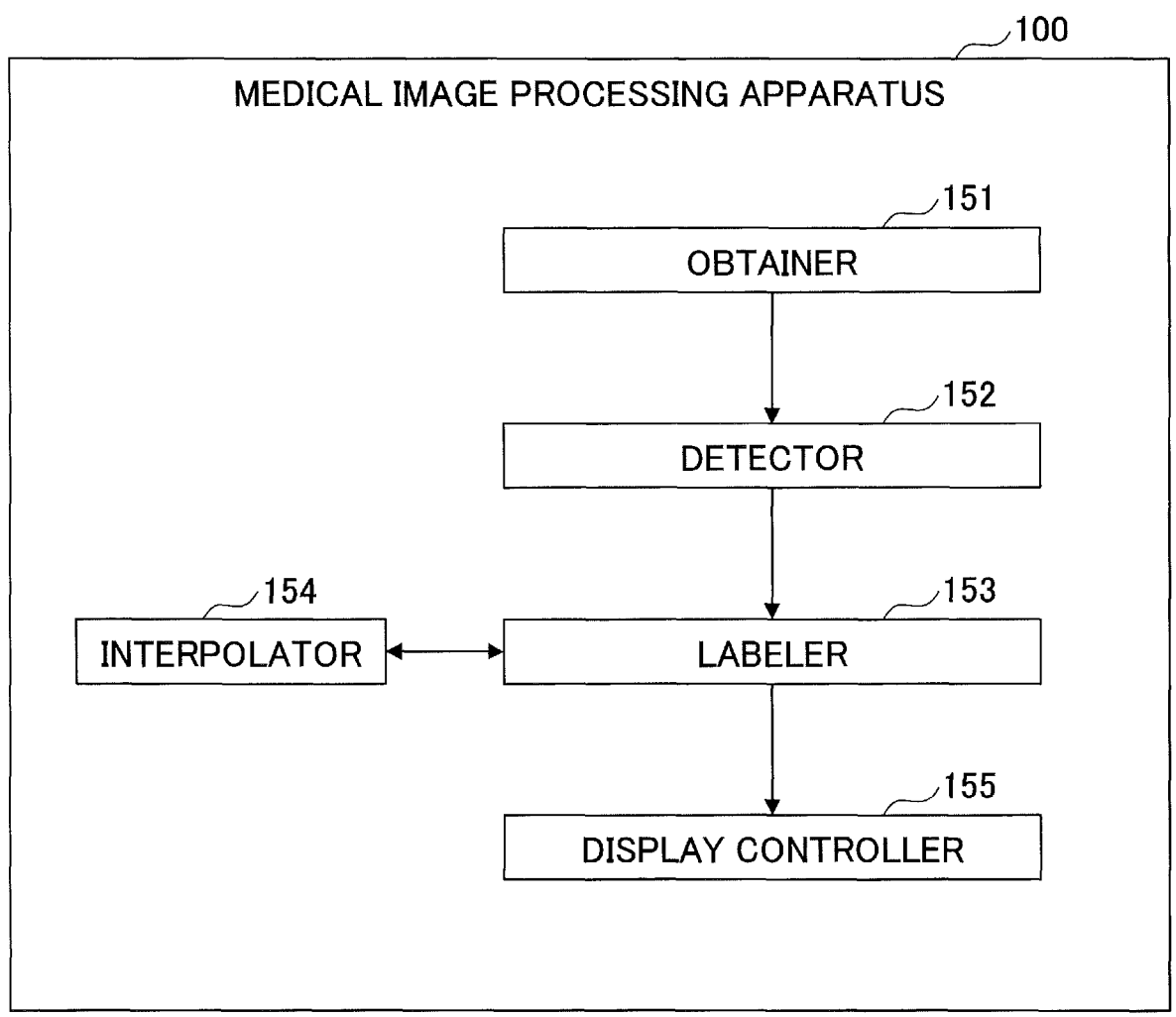
FIG. 2 is a functional block diagram illustrating a configuration of a medical image processing apparatus.

Next, a functional configuration of the medical image processing apparatus 100 will be described. As described above, the CPU 101 implements each function of the medical image processing apparatus 100 by loading programs and data stored in the ROM 102, the auxiliary storage 104, and the like on the RAM 103 and executing a process. FIG. 2 is a functional block diagram illustrating a configuration of the medical image processing apparatus 100. As illustrated in FIG. 2, the medical image processing apparatus 100 includes an obtainer 151, a detector 152, a labeler 153, an interpolator 154, and a display controller 155.

The obtainer 151 obtains medical image data from the outside via the external I/F 107.

Based on a result of learning executed in advance, the detector 152 detects predetermined parts such as vertebral bodies (including second cervical vertebrae), intervertebral disks, sacrums, and the like in a medical image obtained by the obtainer 151, to detect detection points for the respective detected parts. The method of learning is not limited in particular. For example, the detector 152 may generate patches by using a sliding window for the entirety or a selected region of a medical image, to identify a part of each patch. Also, when generating patches, object detection may be executed to identify each extracted region. A detection result may be classified by using at least two groups among the vertebral bodies, intervertebral disks, sacrums, and second cervical vertebrae; and the other regions.

The labeler 153 executes labeling sacrums, vertebral bodies (including second cervical vertebrae), and intervertebral disks detected by the detector 152 that satisfy predetermined conditions. For example, in the case where vertebral bodies, intervertebral disks, and sacrums have been detected, the labeler 153 sets the detection point of a sacrum as the first reference point to executes labeling the sacrum, an intervertebral disk, a vertebral body, another intervertebral disk, another vertebral body, and so on in this order.

When it has been determined by the labeler 153 that the vertebral bodies (including the second cervical vertebrae) and the intervertebral disks detected by the detector 152 include a part not satisfying the predetermined condition described above, the interpolator 154 interpolates such a vertebral body or intervertebral disk. For example, if there is a vertebral body or intervertebral disk in a medical image that cannot be detected by the detector 152, the interpolator 154 interpolates this part by using, for example, at least two groups among the vertebral bodies, intervertebral disks, sacrums, and second cervical vertebrae that have been detected. The labeler 153 also labels the vertebral body or intervertebral disk interpolated by the interpolator 154. The process of the labeler 153 may be executed in parallel with the process executed by the interpolator 154.

The display controller 155 causes the display 105 to display data on which labeling has been executed by the labeler 153. The data is not limited to be displayed via the display controller 155, and may be output as a file.

Figure 3:
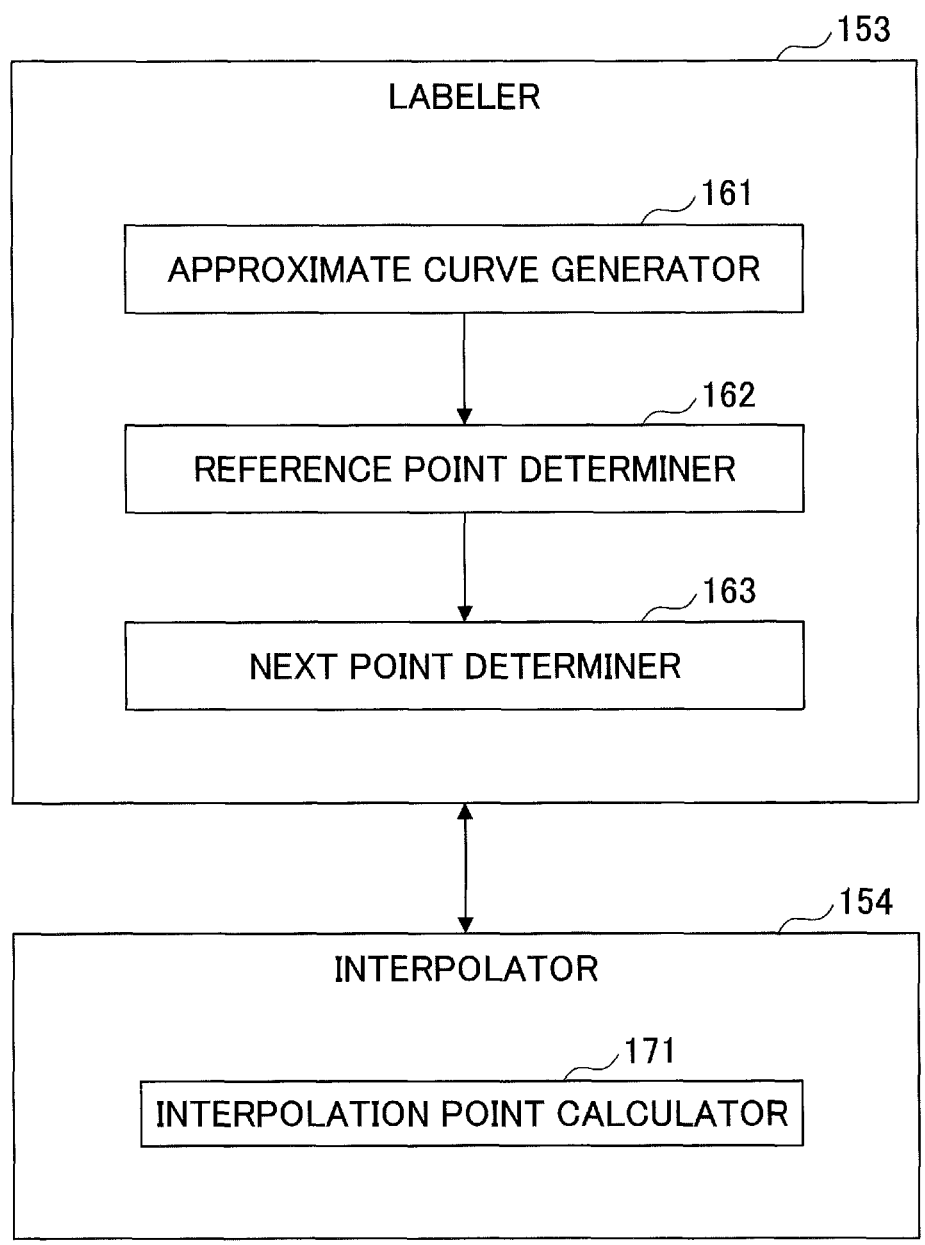
FIG. 3 is a functional block diagram illustrating details of a labeler and an interpolator.

Next, the labeler 153 and the interpolator 154 will be described in detail. FIG. 3 is a functional block diagram illustrating the labeler 153 and the interpolator 154 in detail. As illustrated in FIG. 3, the labeler 153 includes an approximate curve generator 161, a reference point determiner 162, and a next point determiner 163, and the interpolator 154 includes an interpolation point calculator 171.

The approximate curve generator 161 generates an approximate curve constituted with multiple line segments connecting the detection points of parts detected by the detector 152.

The reference point determiner 162 determines a point served as a reference when executing labeling, and updates the reference point as the process progresses. For example, if a sacrum is included, the sacrum is set as the first reference point, and the reference point is updated as the process progresses. For example, if a second cervical vertebra is included, the second cervical vertebra is set as the first reference point, and the reference point is updated as the process progresses.

Based on the reference point determined by the reference point determiner 162, the next point determiner 163 determines whether a vertebral body or an intervertebral disk that satisfies a predetermined condition set for the reference point has been detected, and depending on the determination result, determines a point to be served as the next reference point (next point).

If it has been determined by the next point determiner 163 that a vertebral body or an intervertebral disk satisfying the above-mentioned predetermined condition has not been detected, the interpolation point calculator 171 refers to the above-mentioned predetermined condition to calculate the interpolation point of the vertebral body or intervertebral disk. The method of calculating an interpolation point will be described in detail later.

Figure 4:
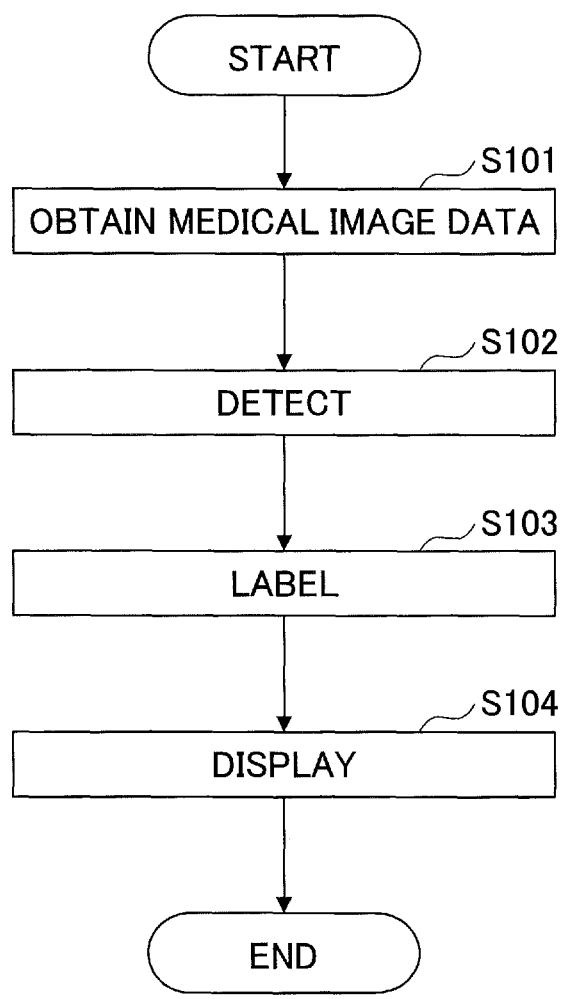
FIG. 4 is a flowchart illustrating operations of a medical image processing apparatus.

Next, operations of the medical image processing apparatus 100 will be described. FIG. 4 is a flowchart illustrating operations of the medical image processing apparatus 100. These operations are implemented by the CPU 101 executing a program stored in the auxiliary storage 104.

First, the obtainer 151 obtains medical image data via the external I/F 107 (Step S101). Next, the detector 152 detects predetermined parts such as vertebral bodies, intervertebral disks, sacrums, and the like from the medical image data obtained by the obtainer 151, to determine a detection point for each of the detected parts (Step S102). Thereafter, the labeler 153 labels the predetermined parts included in the medical image data obtained by the obtainer 151 (Step S103). Although the process executed by the labeler 153 will be described in detail later, the labeler 153 causes the interpolator 154 to interpolate a vertebral body or intervertebral disk where necessary, to execute labeling. After the labeling executed by the labeler 153, the display controller 155 causes the display 105 to display the labeled medical image. Examples of the display on the display 105 will be described later.

Figure 5:
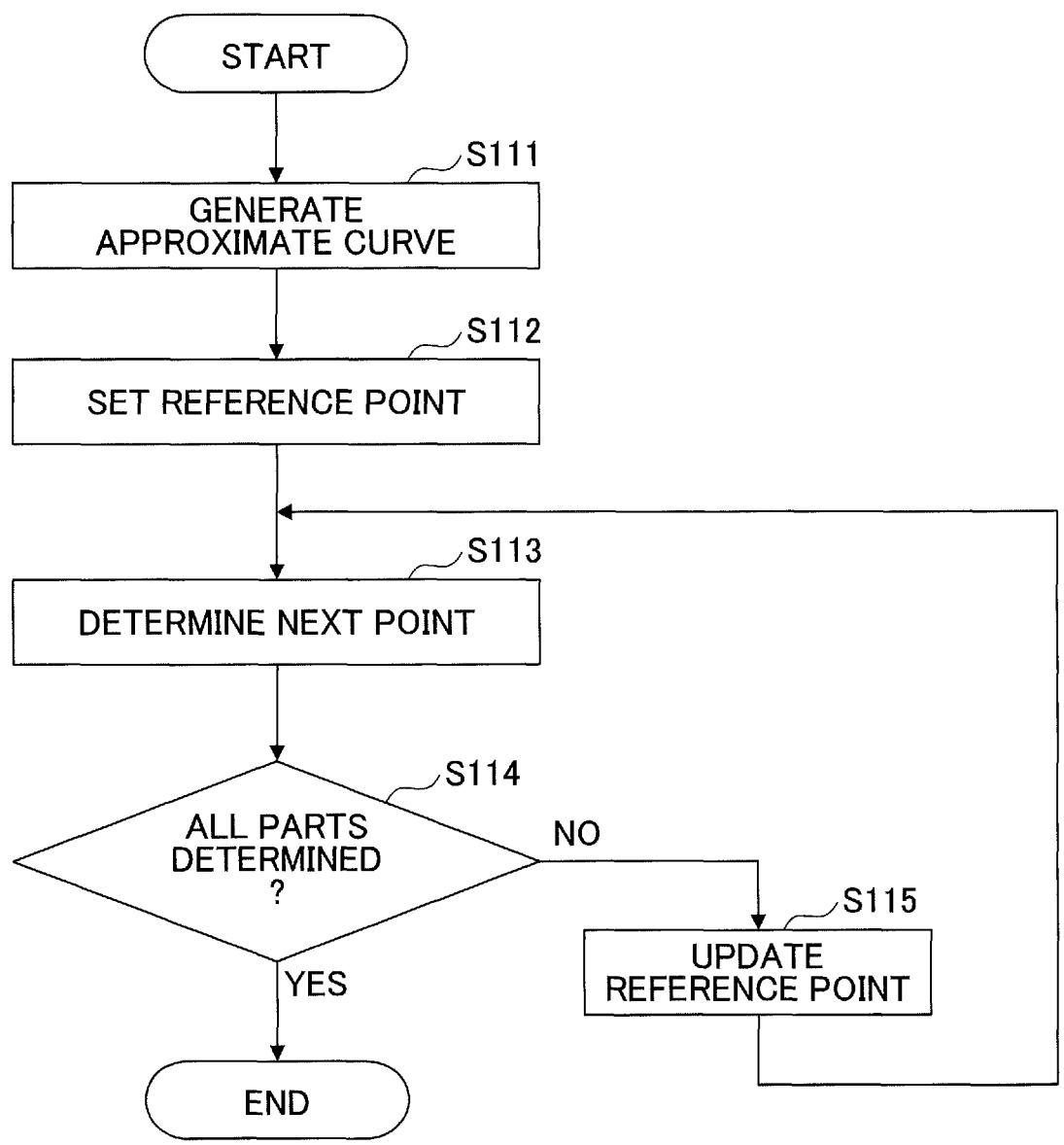
FIG. 5 is a flowchart illustrating a process executed by a labeler and an interpolator.

Next, a process executed by the labeler 153 and the interpolator 154 will be described in detail. FIG. 5 is a flowchart illustrating a process executed by the labeler 153 and the interpolator 154. This process is implemented by the CPU 101 executing a program stored in the auxiliary storage 104.

First, the approximate curve generator 161 generates an approximate curve of multiple line segments connecting the detection points determined by the detector 152 (Step S111). Next, the reference point determiner 162 determines the first reference point from among the detection points determined by the detector 152. For example, if a sacrum is included, the detection point of the sacrum is set as the first reference point, or if the second cervical vertebra is included, the second cervical vertebra is set as the first reference point (Step S112). Thereafter, the next point determiner 163 interoperates with the interpolation point calculator 171 when necessary to determine a point to be set as the next reference point based on the reference point determined by the reference point determiner 162 (Step S113). The process executed the next point determiner 163 and the interpolation point calculator 171 will be described in detail later. After a determination executed by the next point determiner 163, the reference point determiner 162 determines whether the determination has been completed for all of the predetermined parts (Step S114), and if not completed, updates the reference point to a labeling point determined at Step S113 (Step S115), and Step S113 is executed again. Meanwhile, it is preferable that the approximate curve is formed, for example, to pass through a detection point set as the first reference point, or to have this detection point located outside the arc. This is because a tangent passing through the reference point may be generated later.

Figure 6:
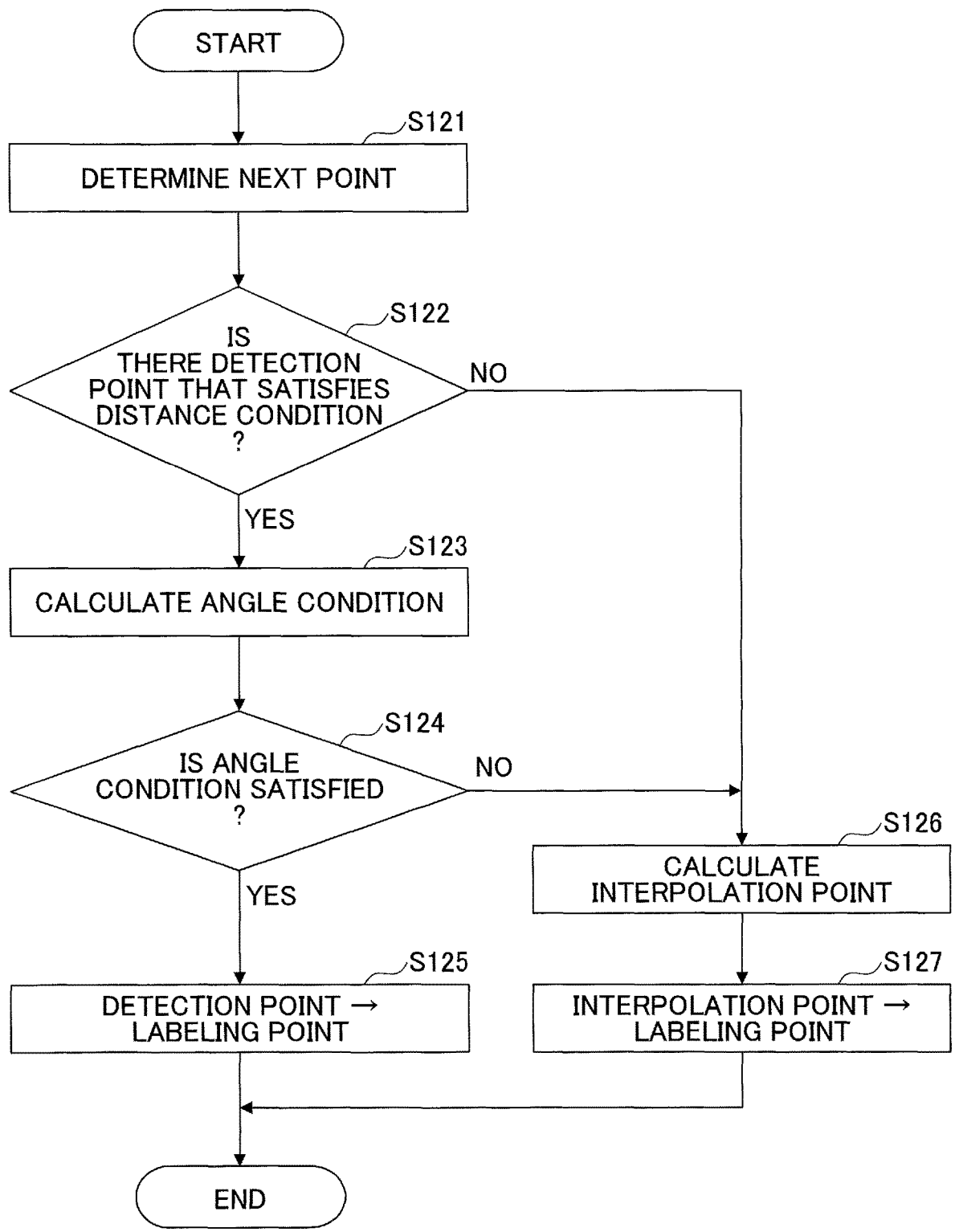
FIG. 6 is a flowchart illustrating a process executed by a next point determiner and an interpolation point calculator.

Next, the process executed by the next point determiner 163 and the interpolation point calculator 171 will be described in detail. FIG. 6 is a flowchart illustrating the process executed by the next point determiner 163 and the interpolation point calculator 171. This process is implemented by the CPU 101 executing a program stored in the auxiliary storage 104.

First, the next point determiner 163 determines candidates for the next point from among the detection points determined by the detector 152 (Step S121). For example, if the current reference point is set on a sacrum, a second cervical vertebra, or another vertebral body, the detection points of intervertebral disks are determined as candidates for the next point. Also, if the current reference point is an intervertebral disk, the detected points of vertebral bodies are detected as candidates of the next point. Next, the next point determiner 163 determines whether there is a detection point that satisfies a distance condition predetermined with respect to the current reference point among the candidates of the next point (Step S122). If there is a detection point that satisfies the distance condition, the next point determiner 163 calculates an angle condition with respect to the current reference point (Step S123), to determine whether the detection point that satisfies the distance condition satisfies this angle condition (Step S124). If this detection point satisfies the angle condition, the next point determiner 163 determines this detection point as the labeling point of a part adjacent to the current reference point (Step S125). On the other hand, if there is no detection point that satisfies the distance condition at Step S122 or if the angle condition is not satisfied at Step S124, the interpolation point calculator 171 calculates an interpolation point (Step S126), and the next point determiner 163 determines this interpolation point as the labeling point of the part adjacent to the current reference point (Step S127). The next point determiner 163 sets the labeling point determined in this way as the next reference point (next point).

Note that in this example, although the executed process is based on both of the distance condition and the angle condition, the process may be executed based on only one of the distance condition and the angle condition.

Here, a specific example of the operations of the medical image processing apparatus 100 will be described. FIGS. 7A to 7M are diagrams illustrating a method of processing a medical image including a sacrum.

Figure 7A:
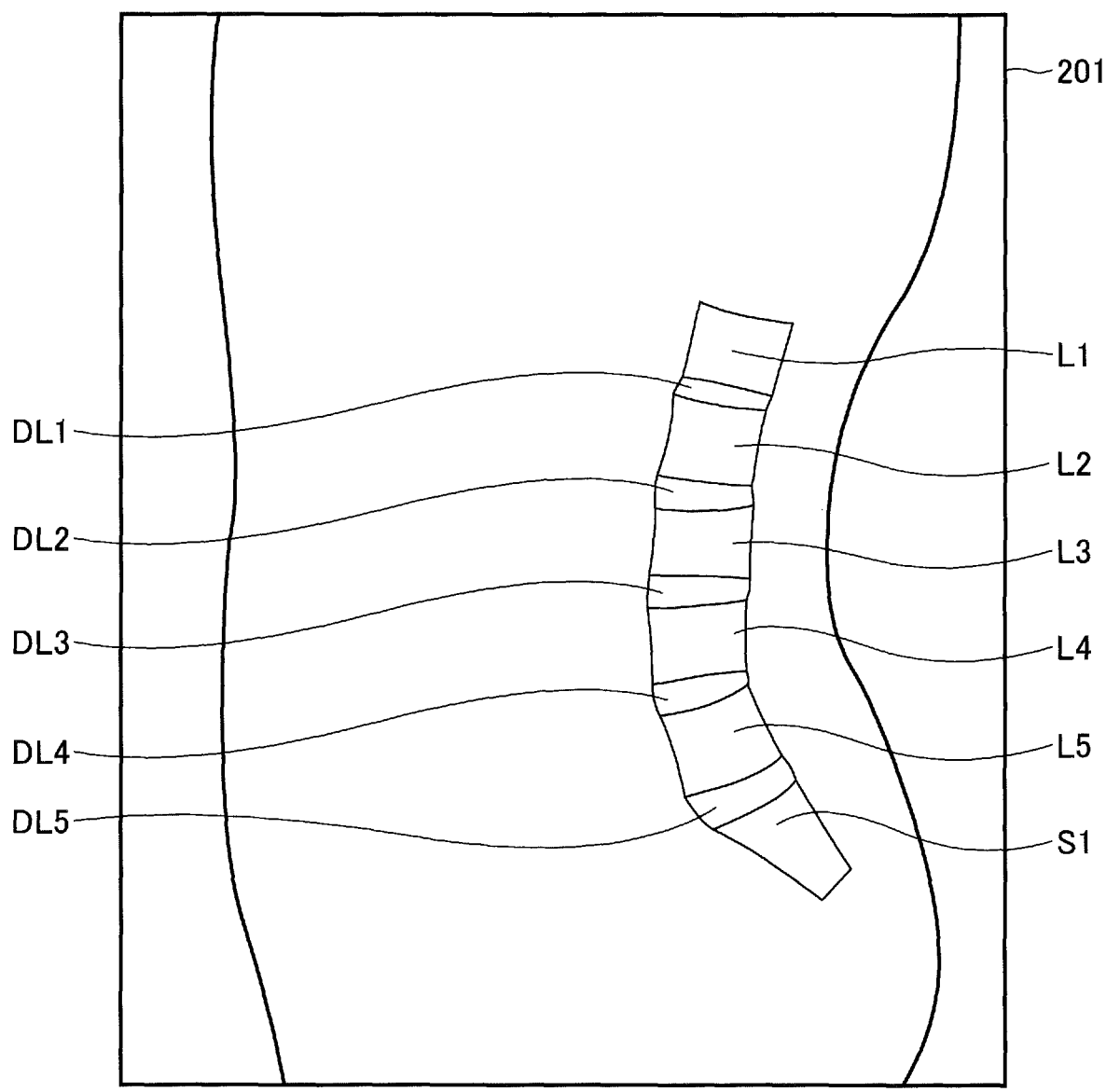
FIG. 7A is a diagram (first example) illustrating a method of processing a medical image including a sacrum.

In this example, as illustrated in FIG. 7A, assume that a medical image 201 is used in which a first lumbar vertebra L1, a second lumbar vertebra L2, a third lumbar vertebra L3, a fourth lumbar vertebra L4, a fifth lumbar vertebra L5, and a sacrum S1 are imaged. There is an intervertebral disk DL1 between the first lumbar vertebra L1 and the second lumbar vertebra L2; there is an intervertebral disk DL2 between the second lumbar vertebra L2 and the third lumbar vertebra L3; there is an intervertebral disk DL3 between the third lumbar vertebra L3 and the fourth lumbar vertebra L4; there is an intervertebral disk DL4 between the fourth lumbar vertebra L4 and the fifth lumbar vertebra L5; and there is an intervertebral disk DL5 between the fifth lumbar vertebra L5 and the sacrum S1. The data of this medical image 201 is obtained by the obtainer 151.

Figure 7B:
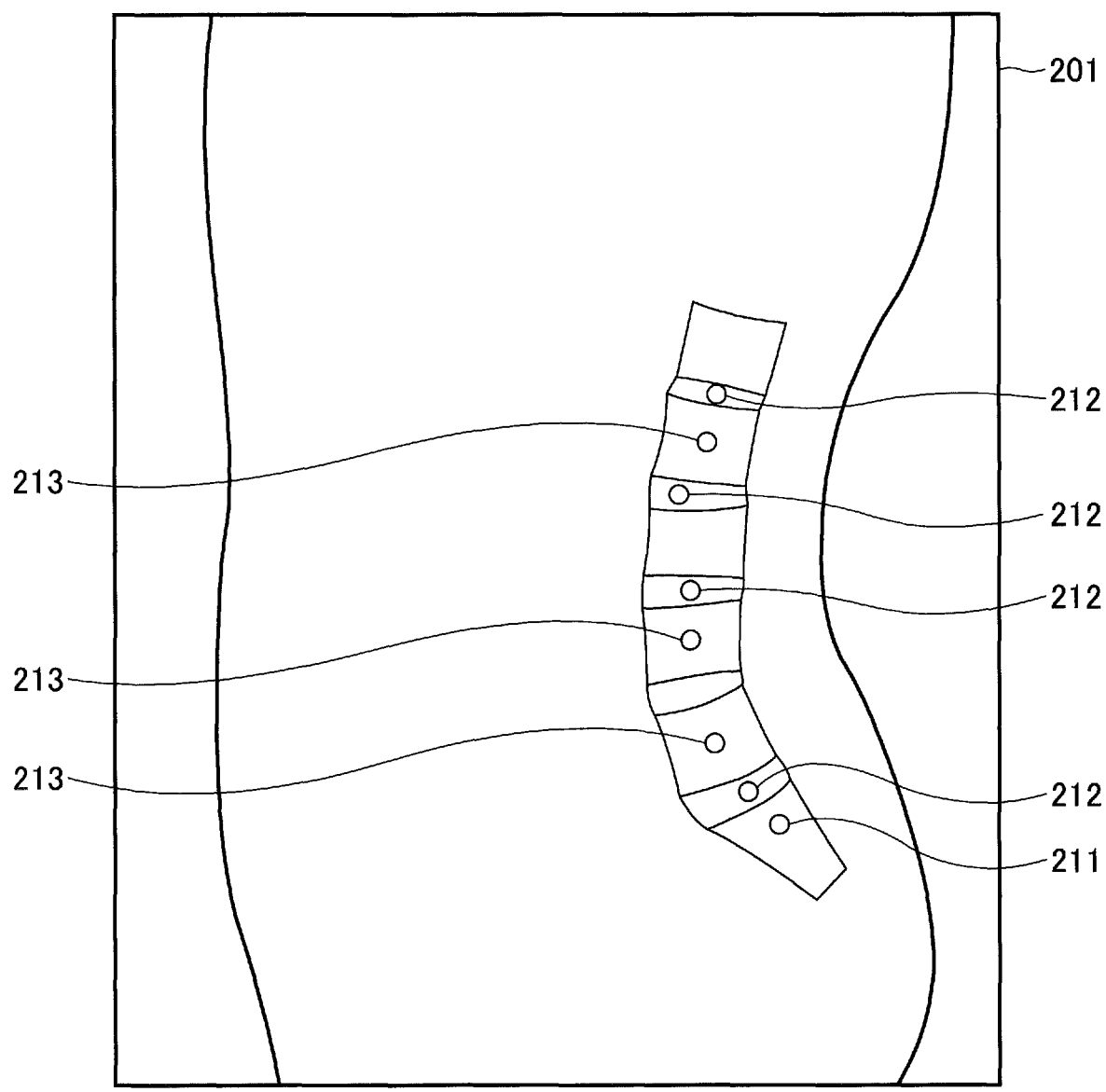
FIG. 7B is a diagram (second example) illustrating a method of processing a medical image including a sacrum.

The detector 152 attempts to detect the first lumbar vertebra L1, the second lumbar vertebra L2, the third lumbar vertebra L3, the fourth lumbar vertebra L4, the fifth lumbar vertebra L5, the sacrum S1, the intervertebral disk DL1, the intervertebral disk DL2, the intervertebral disk DL3, the intervertebral disk DL4, and the intervertebral disk DL5, and then, determines detection points for the parts that have been detected. In this example, as illustrated in FIG. 7B, assume that a detection point 211 of the sacrum S1 has been determined, detection points 212 have been determined for a part of the intervertebral disks, and detection points 213 have been determined for a part of the lumbar vertebrae; however, detection points could not be detected for another part of the intervertebral disks and another part of the lumbar vertebrae.

Figure 7C:
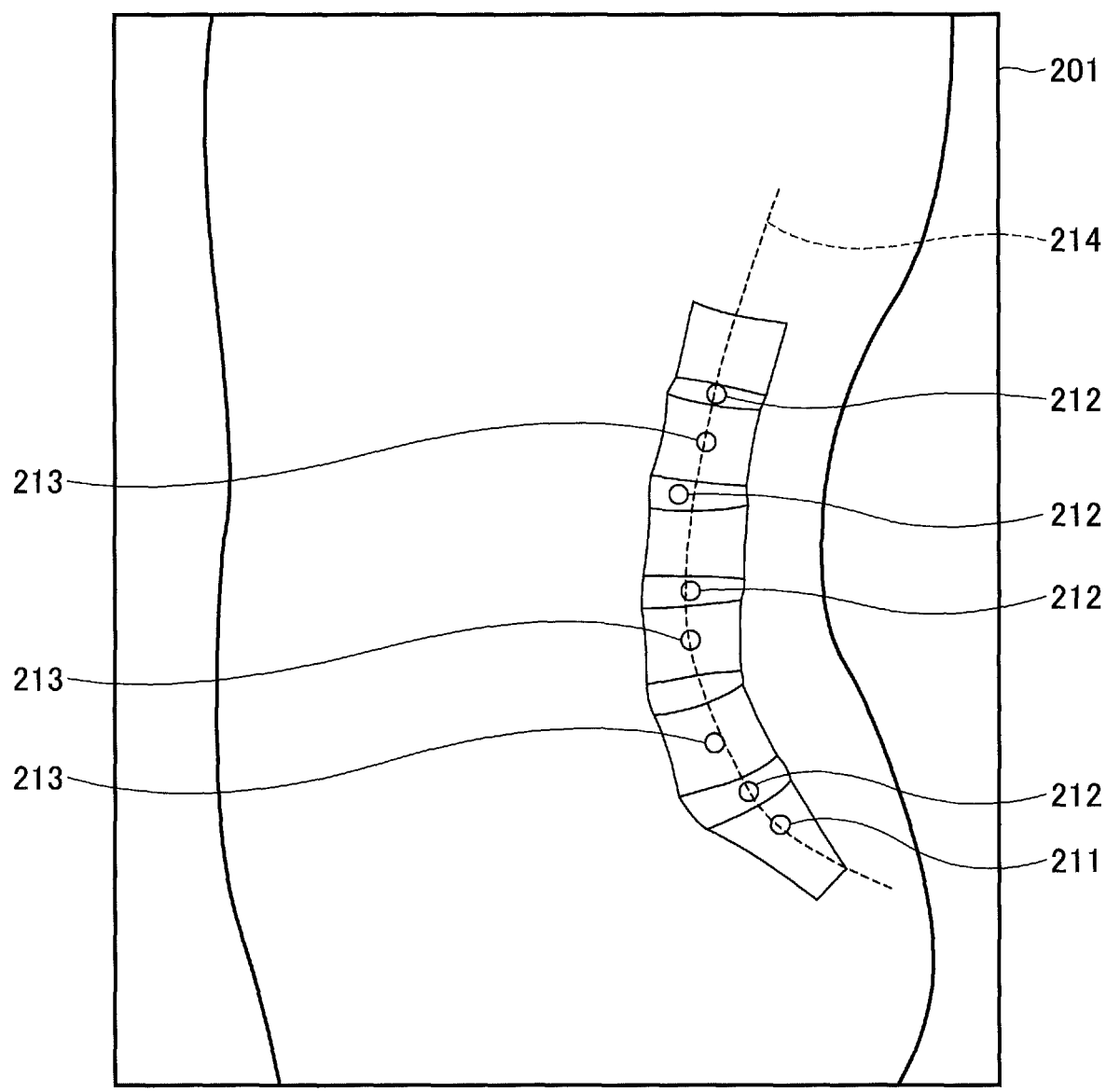
FIG. 7C is a diagram (third example) illustrating a method of processing a medical image including a sacrum.

As illustrated in FIG. 7C, the approximate curve generator 161 of the labeler 153 generates an approximate curve 214 of a group of line segments connecting the detection points 211, 212 and 213 determined by the detector 152.

Figure 7D:
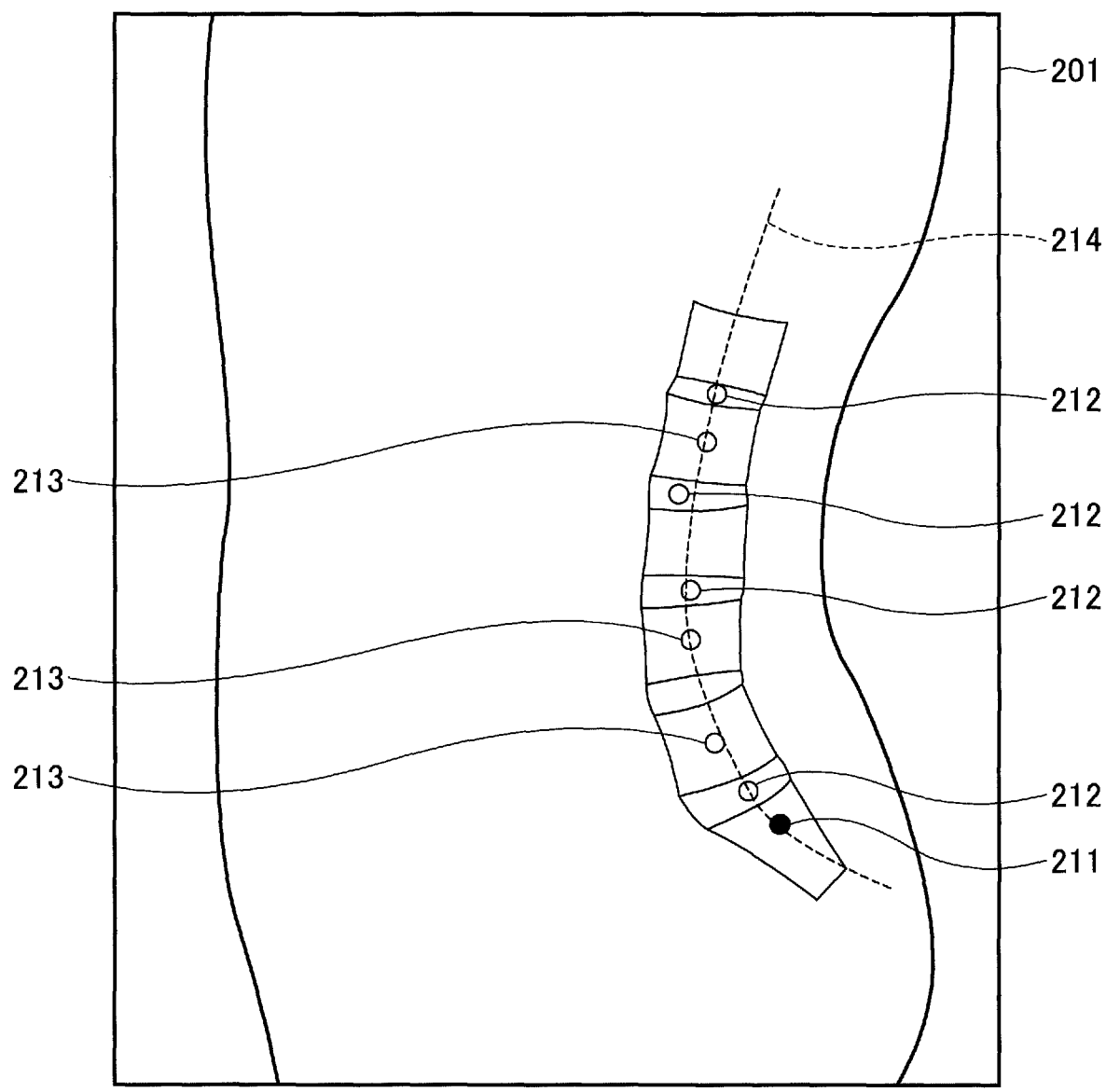
FIG. 7D is a diagram (fourth example) illustrating a method of processing a medical image including a sacrum.

As illustrated in FIG. 7D, the reference point determiner 162 of the labeler 153 determines the first reference point from among the detection points 211, 212 and 213 determined by the detector 152. In this example, the detection point 211 of the sacrum S1 is determined as the first reference point.

Figure 7E:
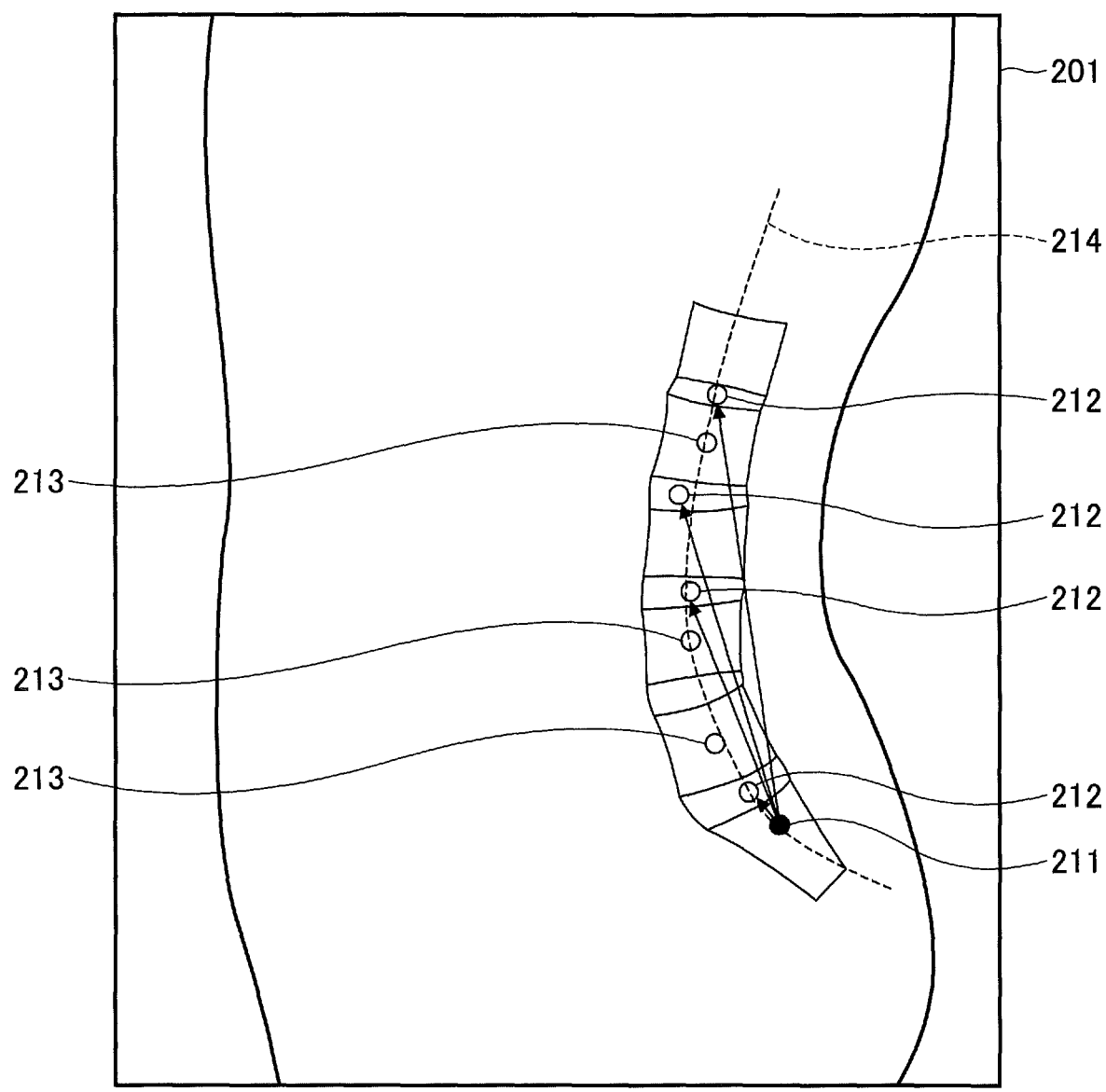
FIG. 7E is a diagram (fifth example) illustrating a method of processing a medical image including a sacrum.

As illustrated in FIG. 7E, since the current reference point is set on the sacrum S1, the next point determiner 163 of the labeler 153 determines multiple detection points 212 of the intervertebral disks as candidates for the next point.

Figure 7F:
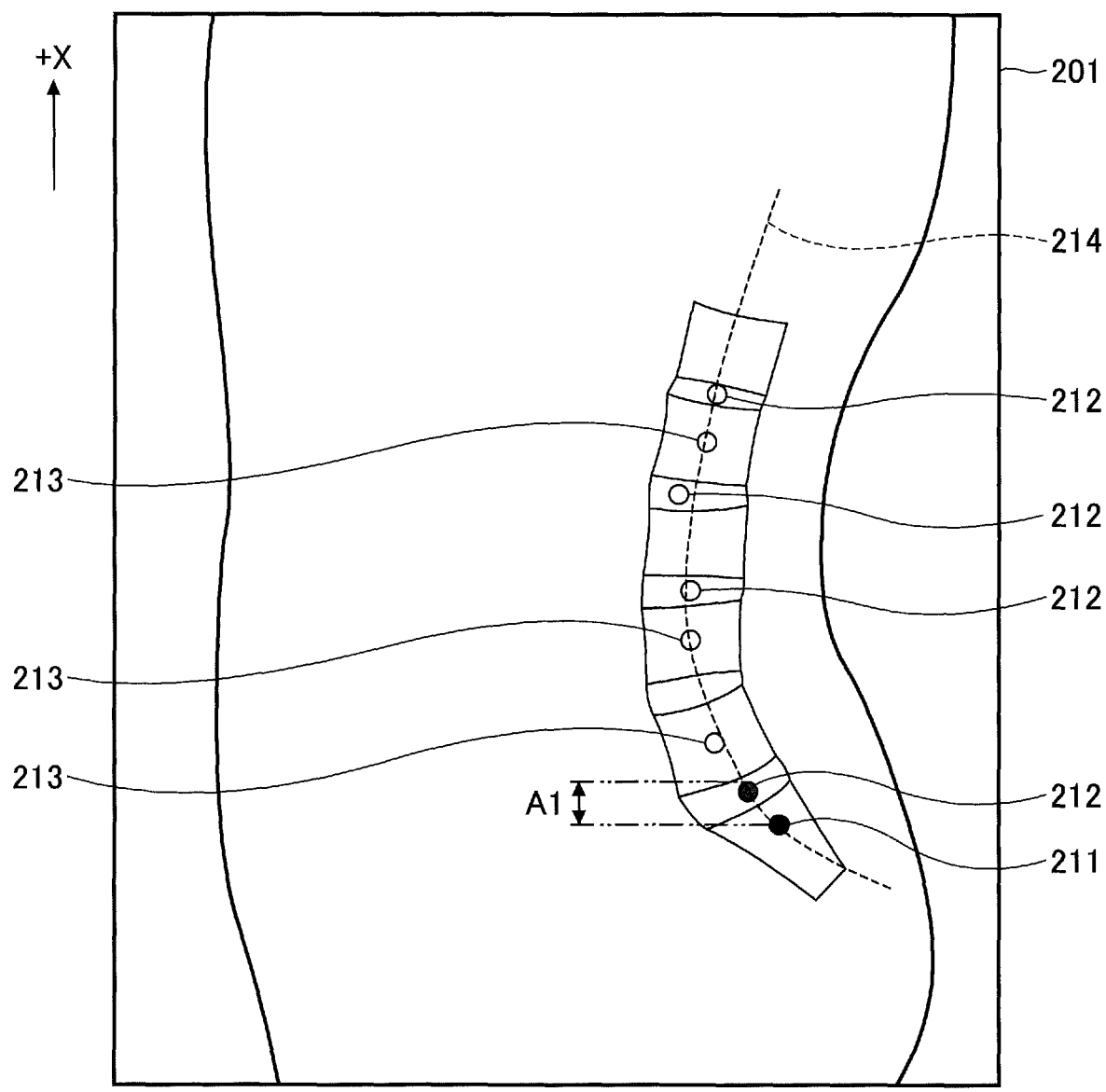
FIG. 7F is a diagram (sixth example) illustrating a method of processing a medical image including a sacrum.

Then, the next point determiner 163 determines whether there is a detection point that satisfies a predetermined distance condition with respect to the sacrum S1 among the multiple detection points 212 of the intervertebral disks. For example, as illustrated in FIG. 7F, in a certain direction, for example, a direction from the foot toward the head (+X direction), the next point determiner 163 determines whether there is a detection point whose distance from the detection point 211 is less than or equal to an interpolation distance A1 predetermined with respect to the sacrum S1. Here, assume that the detection point 212 of the intervertebral disk DL5 satisfies the distance condition.

Figure 7G:
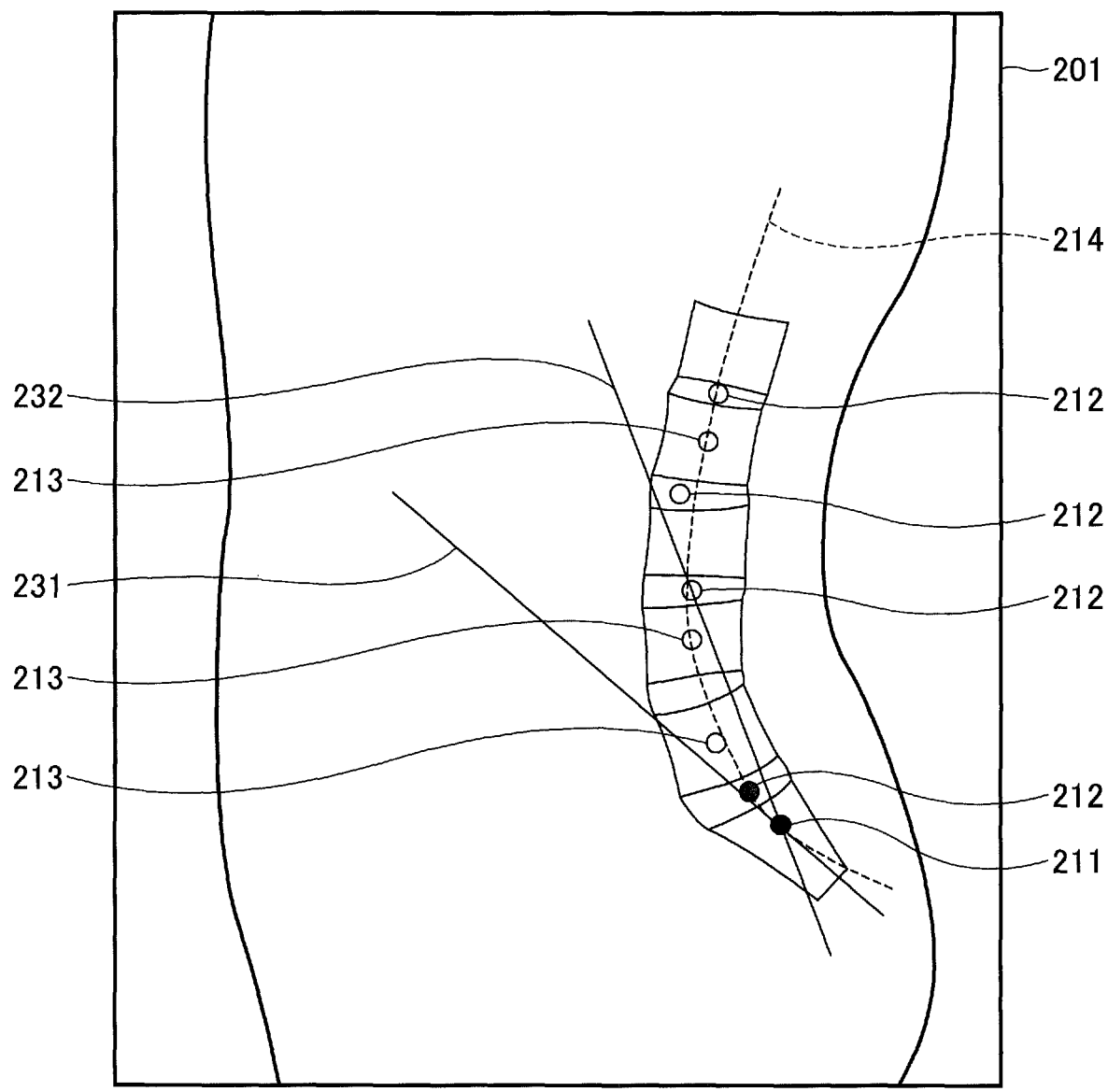
FIG. 7G is a diagram (seventh example) illustrating a method of processing a medical image including a sacrum.

Next, the next point determiner 163 calculates an angle condition with respect to the detection point 211, to determine whether the detection point 212 of the intervertebral disk DL5 satisfies this angle condition. For example, as illustrated in FIG. 7G, the next point determiner 163 calculates two straight lines 231 and 232 by using the approximate curve 214, to determine whether the relationship between the angle formed by these straight lines and the position of the detection point 212 satisfies the predetermined condition.

Here, a method of determining an angle condition will be described. FIGS. 8A to 8E are diagrams illustrating an example of a method of determining an angle condition.

Figure 8A:
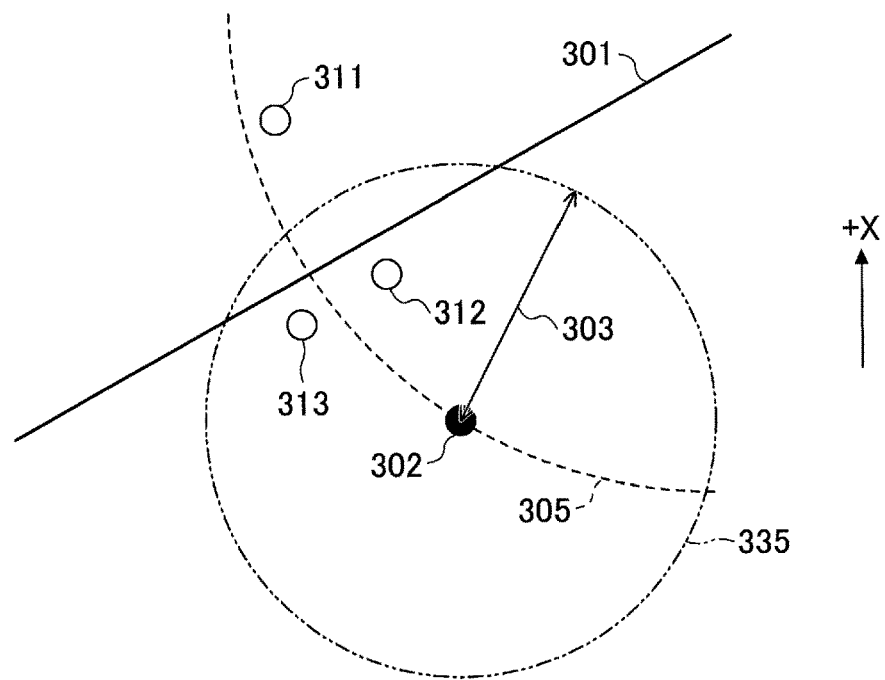
FIG. 8A is a diagram (first example) illustrating an example of a method of determining an angle condition.

In this example, as illustrated in FIG. 8A, assume that there are two parts having a boundary 301 interposed, one of which has a reference point 302, and the other has a candidate detection point of the next point. Also, assume that an approximate curve 305 has been obtained and an interpolation distance 303 is set with respect to the reference point 302.

Figure 8B:
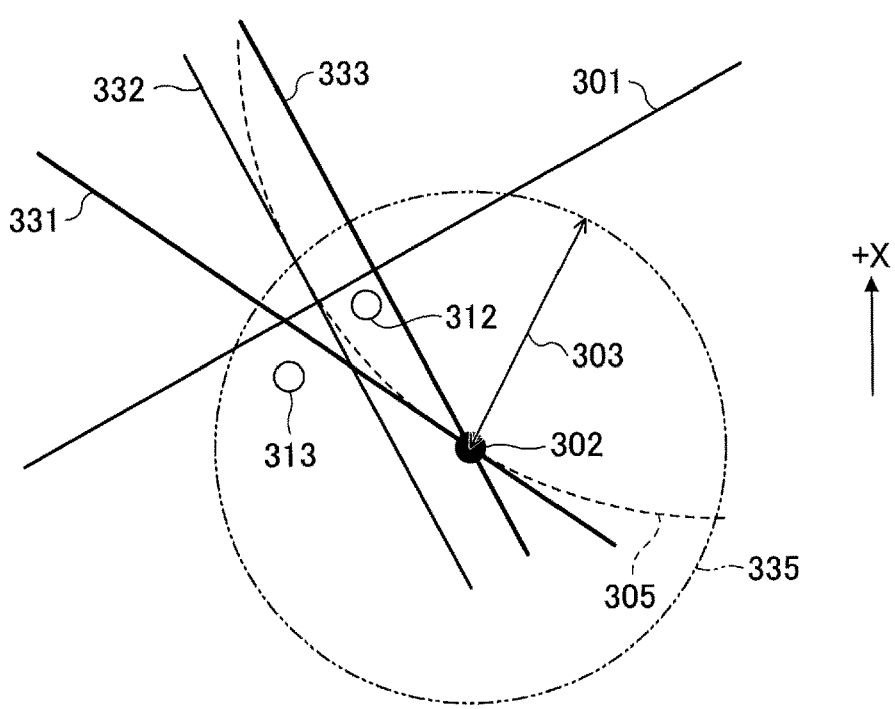
FIG. 8B is a diagram (second example) illustrating an example of a method of determining an angle condition.

As illustrated in FIG. 8B, if the candidate detection point of the next point is the detection point 312 or 313 whose distance from the reference point 302 is less than or equal to the interpolation distance 303, the next point determiner 163 calculates a tangent 331 of the approximation curve 305 that passes through the reference point 302. The next point determiner 163 further calculates a tangent 332 of the approximate curve 305 passing through the intersection between the curve 335, which is separated from the reference point 302 by the interpolation distance 303, and the approximate curve 305, to calculate a straight line 333 that is parallel with the tangent 332 and passes through the reference point 302. Then, by arithmetically using the magnitude of the angle, the next point determiner 163 determines whether the detection point 312 or 313 is located between the tangent 331 and the straight line 333. For example, assuming that an approximate curve is represented by Expression (1) where x represents the x coordinate, y represents the y coordinate, and pn represents a parameter of the approximate curve, the tangent passing through the reference point 302 is expressed as follows. In other words, representing the x coordinate by $x_s$ and the y coordinate by $y_s$ of the reference point 302, Equation (2) holds; therefore, the tangent passing through the reference point 302 is expressed by Equations (3) to (5).

$$x = p_1 y^3 + p_2 y^2 + p_3 y + p_4 \quad (1)$$

$$x_s = p_1 y_s^3 + p_2 y_s^2 + p_3 y_s + p_4 \quad (2)$$

$$y = ax + b \quad (3)$$

$$a = \frac{1}{3p_1 y_s^2 + 2p_2 y_s + p_3} \quad (4)$$

$$b = -ax_s + y_s \quad (5)$$

Figure 8C:
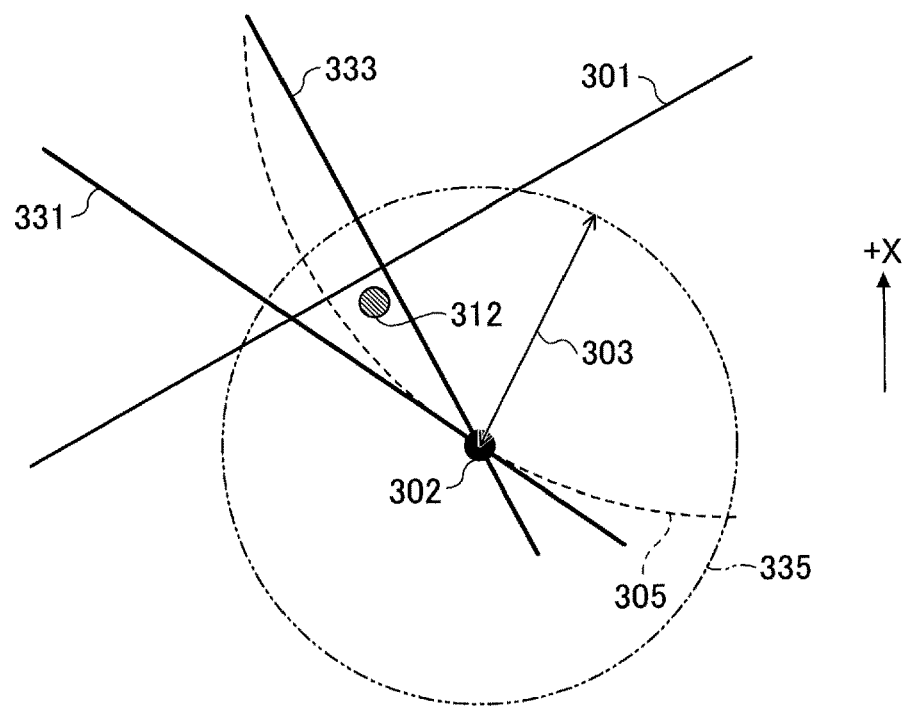
FIG. 8C is a diagram (third example) illustrating an example of a method of determining an angle condition.
Figure 8D:
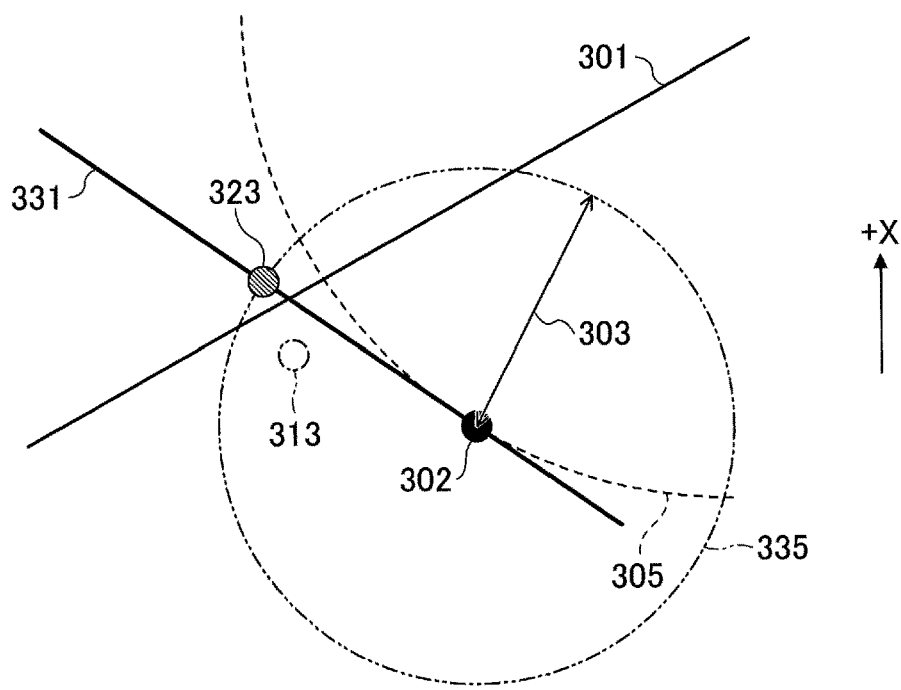
FIG. 8D is a diagram (fourth example) illustrating an example of a method of determining an angle condition.

If the candidate detection point of the next point is the detection point 312 located between the tangent 331 and the straight line 333, as illustrated in FIG. 8C, the next point determiner 163 determines the detection point 312 as it is as the labeling point. On the other hand, if the candidate detection point of the next point is the detection point 313 outside the area between the tangent 331 and the straight line 333, as illustrated in FIG. 8D, the interpolation point calculator 171 determines the intersection point between the tangent 331 and the curve 335 as an interpolation point 323, and the next point determiner 163 determines the interpolation point 323 as the labeling point. For example, assuming that the y coordinate of the reference point 302 is $y_s$, the x coordinate is $x_s$, and the curve 335 that is separated from the reference point 302 by the distance D is a circle, Equation (6) holds. Therefore, by solving simultaneous equations with Equation (3) of the tangent passing through the reference point 302, candidates of the y coordinate $y_d$ and the x coordinate $x_d$ of the interpolation point 323 can be calculated as represented by Equations (7) and (8).

$$(x - x_s)^2 + (y - y_s)^2 = D^2 \quad (6)$$

$$y_d = a \cdot x_d + b \quad (7)$$

$$x_d = -\frac{ab - ay_s - x_s}{a^2 + 1} \pm \sqrt{\text{abs}\left(\frac{D^2 - x_s^2 - (b - y_s)^2}{a^2 + 1} + \left(\frac{ab - ay_s - x_s}{a^2 + 1}\right)^2\right)} \quad (8)$$

Then, from among combinations of the y coordinate $y_d$ and the x coordinate $x_d$, a combination having the smallest y coordinate can be obtained as the interpolation point 323.

Figure 8E:
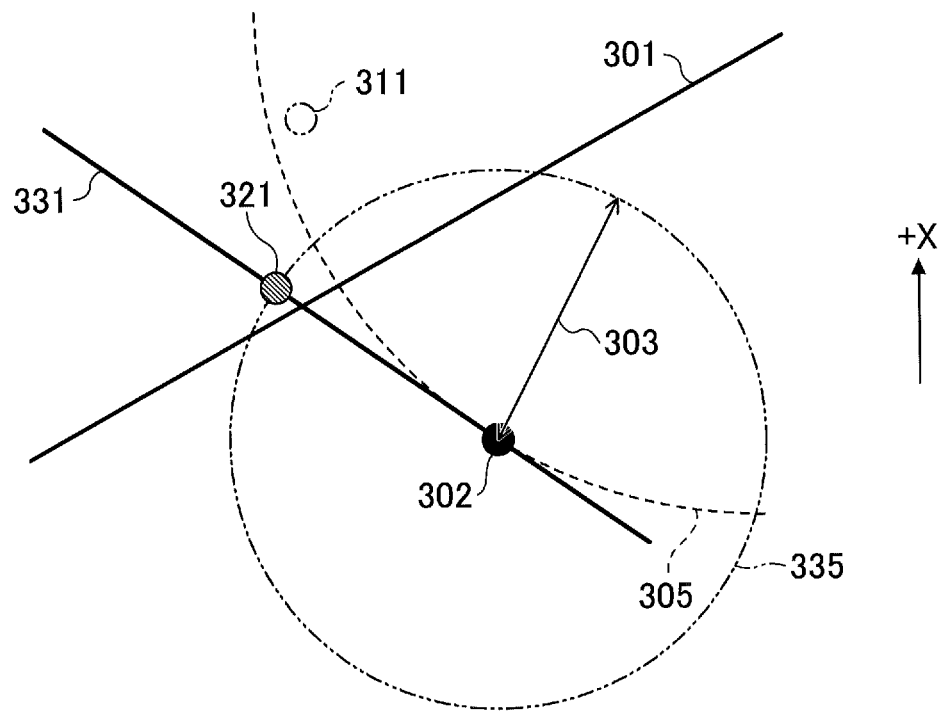
FIG. 8E is a diagram (fifth example) illustrating an example of a determination method of an angle condition.

If the candidate detection point of the next point is the detection point 311 whose distance from the reference point 302 is greater than the interpolation distance 303, as illustrated in FIG. 8E, the next point determiner 163 calculates the tangent 331 of the approximate curve 305 passing through the reference point 302. Then, the interpolation point calculator 171 determines the intersection point between the tangent 331 and the curve 335 as an interpolation point 321, and the next point determiner 163 determines the interpolation point 321 as the labeling point.

Note that as for the interpolation distance, information on a detection frame of the reference point may be used. The information on a detection frame may include, for example, information on the sizes of a vertebral body, an intervertebral disk, and a sacrum. For example, if the detection frame of a lumbar vertebra as the reference point is used, the size of the lumbar vertebra can be known, and hence, the boundary between the lumbar vertebra and the intervertebral disk can be obtained. Since the intervertebral disk has the size of approximately ½ to ⅓ times the size of the lumbar vertebra, the size of ½ to ⅓ times the detection frame of the lumbar vertebra can be estimated as the size of the intervertebral disk, namely, the interpolation distance. Therefore, if the detection frame of the lumbar vertebrae is known, the boundary between the lumbar vertebra and the intervertebral disk can be located, and the interpolation distance can also be estimated, and thereby, the position of the intervertebral disk as the next point can be estimated. Also, the straight line 333 may be calculated by using the information on the detection frame. Also, a distance centered on the reference point may be used as the interpolation distance.

Figure 7H:
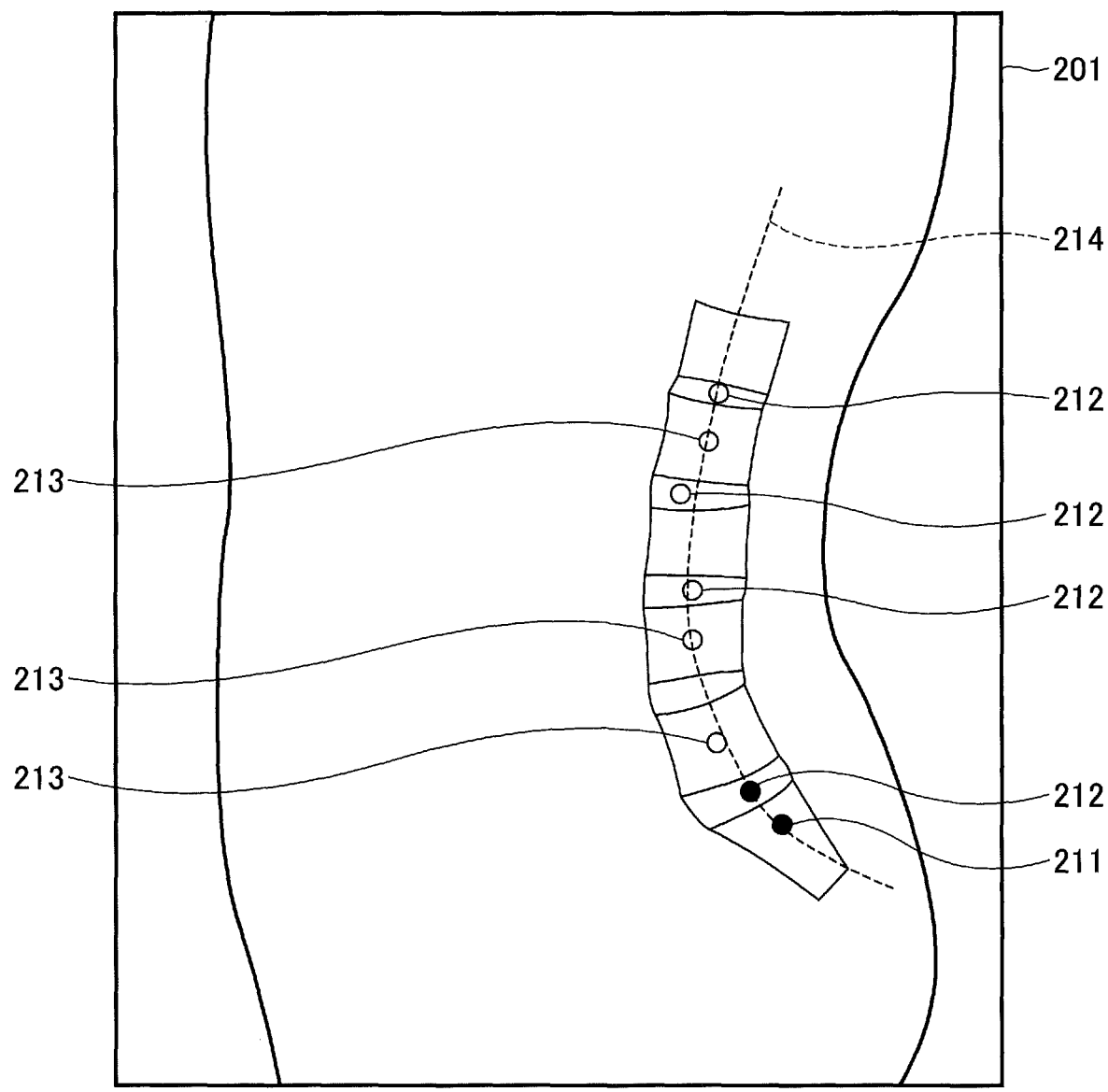
FIG. 7H is a diagram (eighth example) illustrating a method of processing a medical image including a sacrum.

In this way, it is possible to determine whether the angle condition is satisfied. In the example illustrated in FIG. 7G, assume that the detection point 212 of the intervertebral disk DL5 satisfies the angle condition. In this case, as illustrated in FIG. 7H, the next point determiner 163 sets the detection point 212 of the intervertebral disk DL5 as it is as the labeling point of the intervertebral disk DL5, to set the labeling point as the next reference point.

Figure 7I:
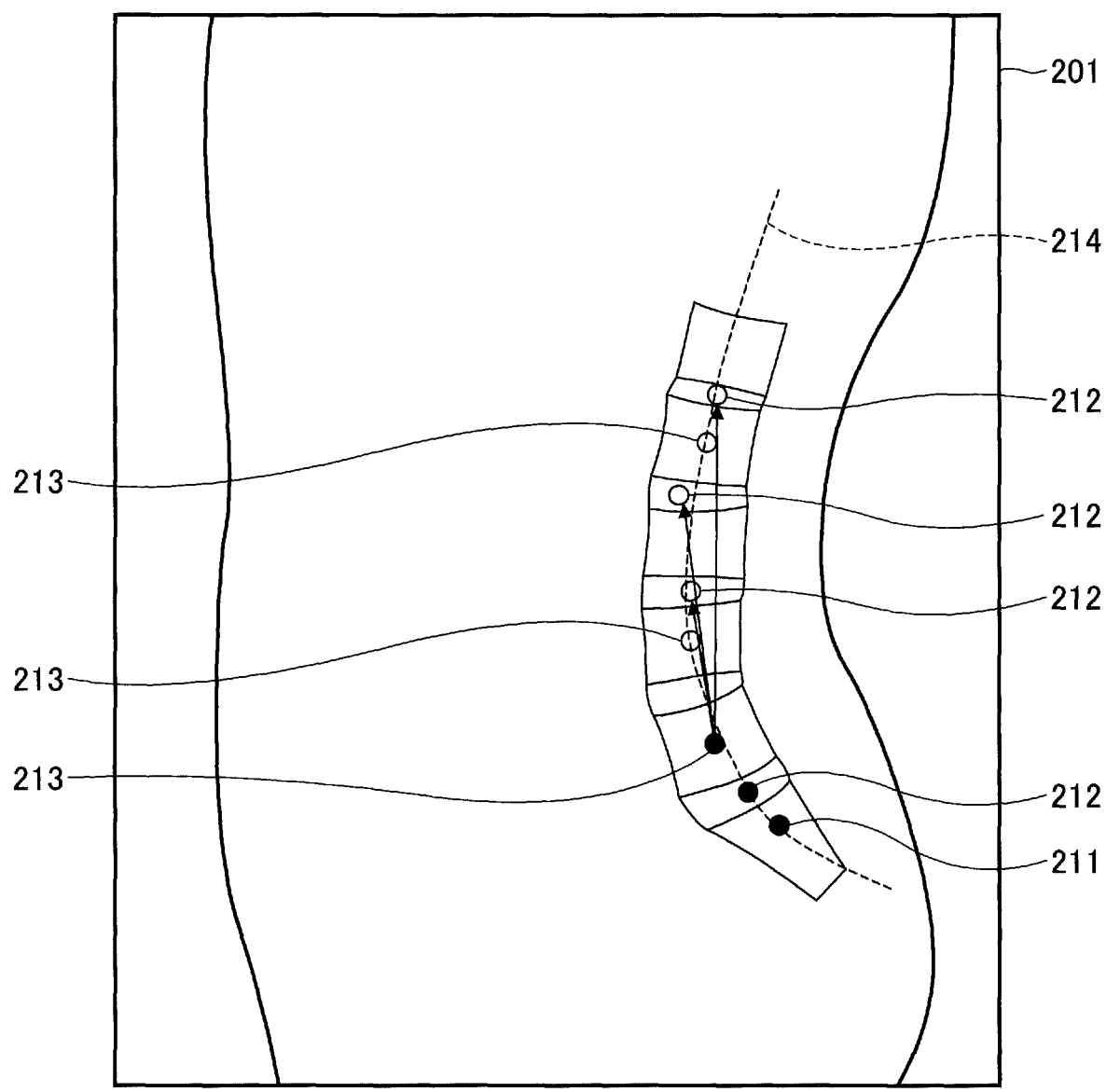
FIG. 7I is a diagram (ninth example) illustrating a method of processing a medical image including a sacrum.

Next, the next point determiner 163 executes a similar process with the detection point 212 of the intervertebral disk DL5 as the reference point. Then in this example, as illustrated in FIG. 7I, assume that the detection point 213 of the fifth lumbar vertebra L5 as it is is set as the labeling point of the fifth lumbar vertebra L5.

Figure 7J:
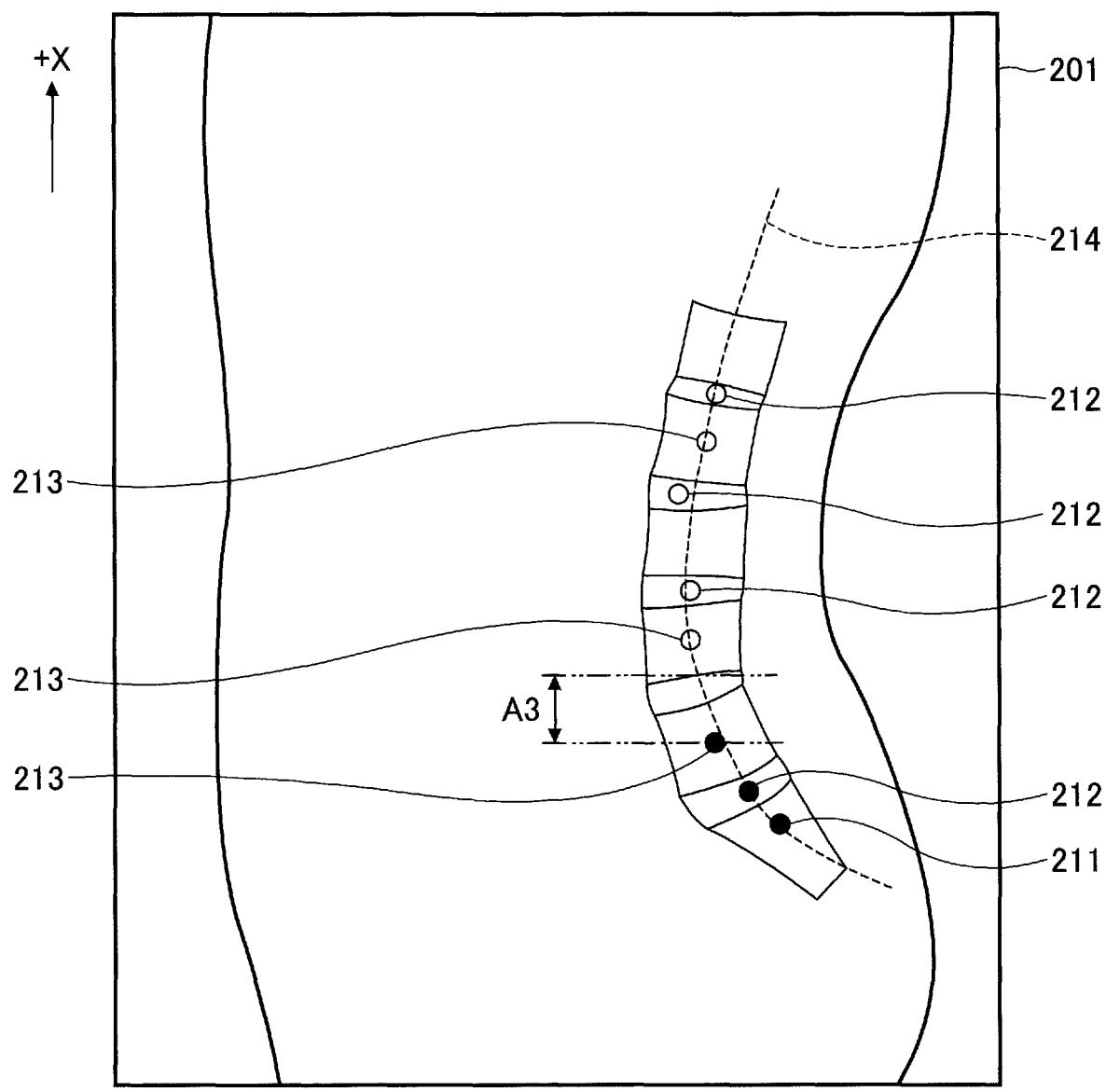
FIG. 7J is a diagram (tenth example) illustrating a method of processing a medical image including a sacrum.
Figure 7K:
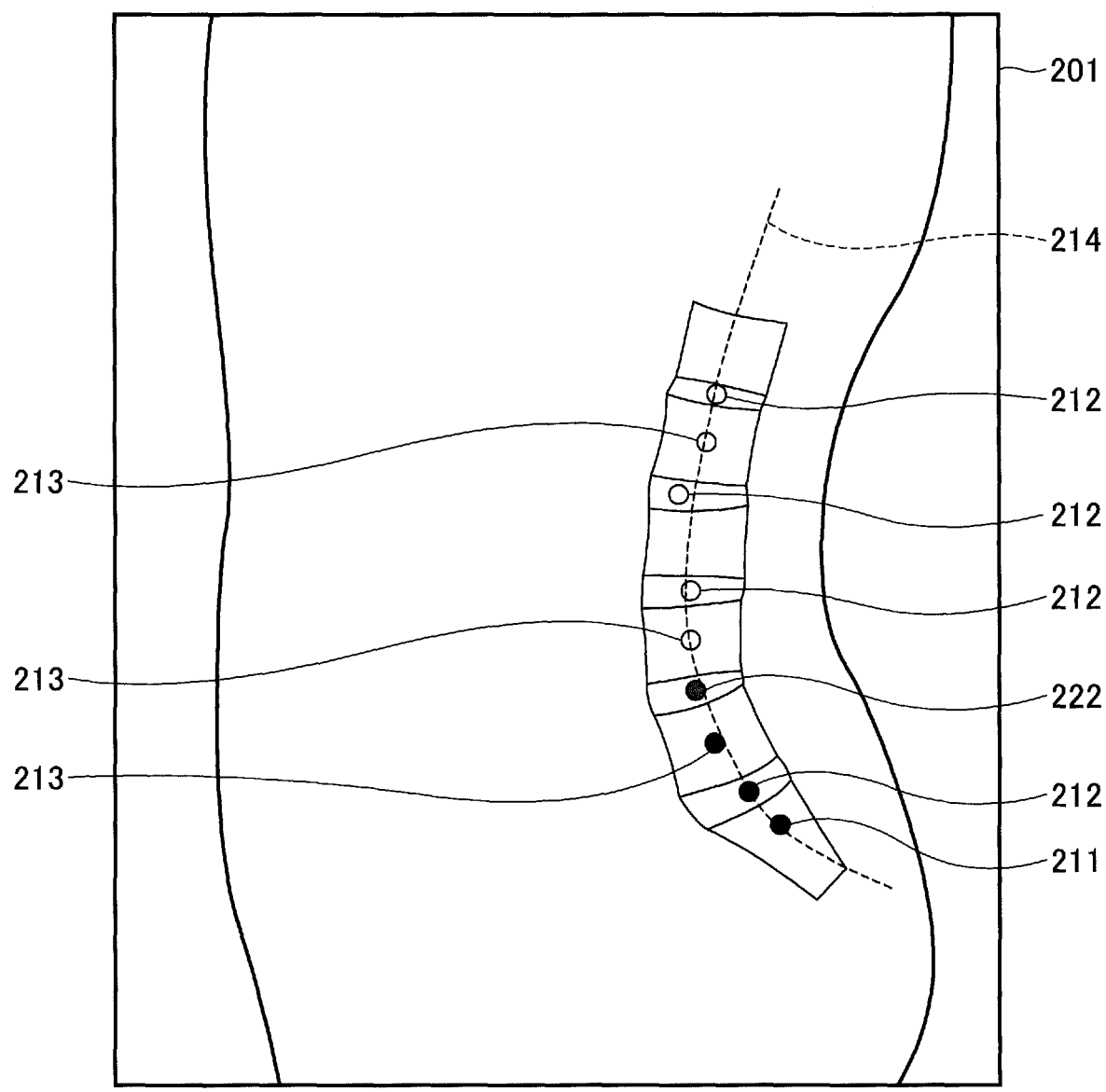
FIG. 7K is a diagram (eleventh example) illustrating a method of processing a medical image including a sacrum.
Figure 7L:
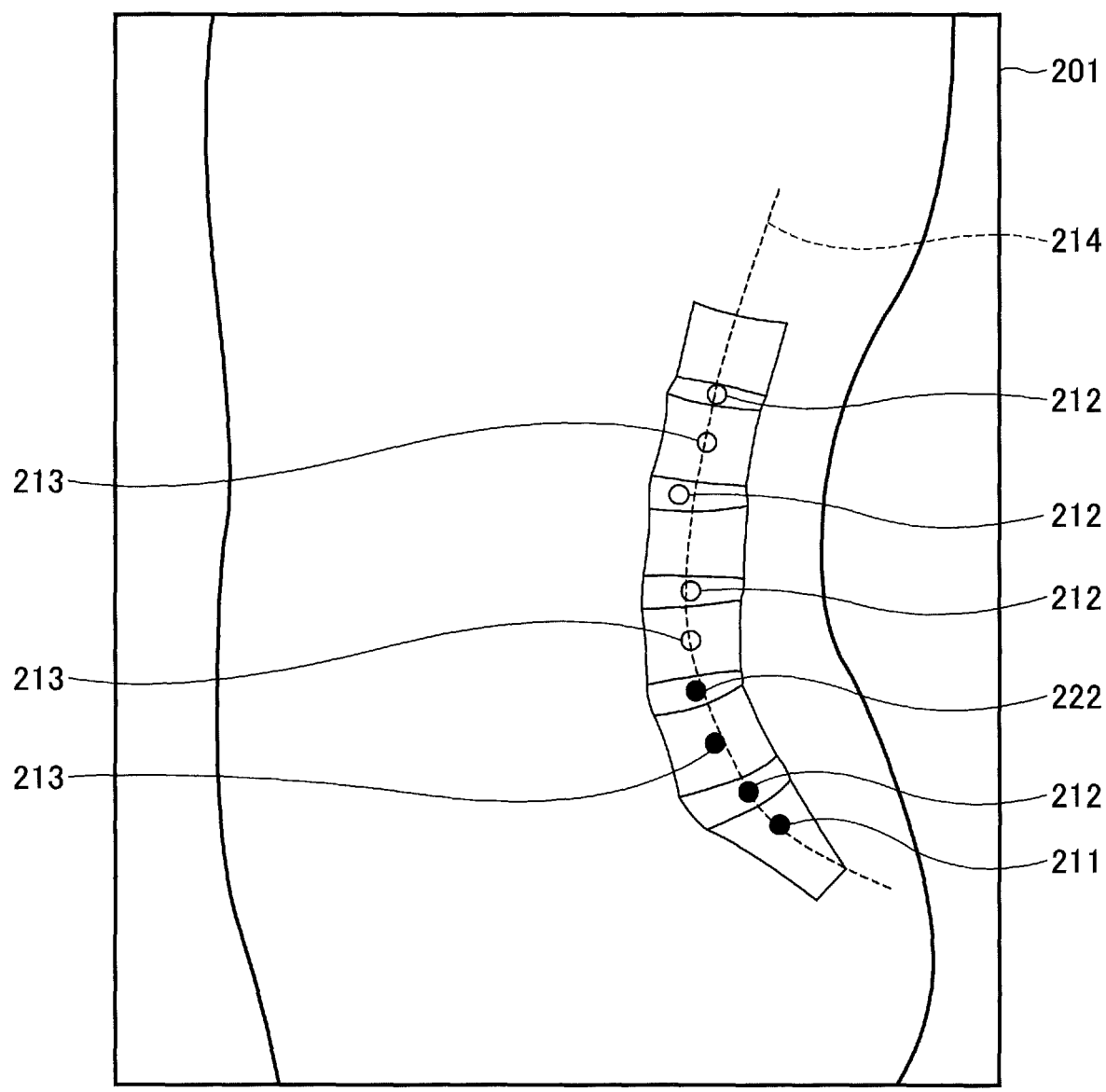
FIG. 7L is a diagram (twelfth example) illustrating a method of processing a medical image including a sacrum.

Next, the next point determiner 163 executes a similar process with the detection point 213 of the fifth lumbar vertebra L5 as the reference point. Then, in this example, as illustrated in FIG. 7J, assume that the intervertebral disk DL4 between the fourth lumbar vertebra L4 and the fifth lumbar vertebra L5 has not been detected. In this case, there is no detection point whose distance in the +X direction is less than or equal to the interpolation distance A3, which has been set for the reference point of the fifth lumbar vertebra L5. Therefore, as illustrated in FIG. 7K, the interpolation point calculator 171 calculates an interpolation point 222 of the intervertebral disk DL4. Then, as illustrated in FIG. 7L, the next point determiner 163 sets the interpolation point 222 of the intervertebral disk DL4 as the labeling point of the intervertebral disk DL4, and sets it as the next reference point.

Figure 7M:
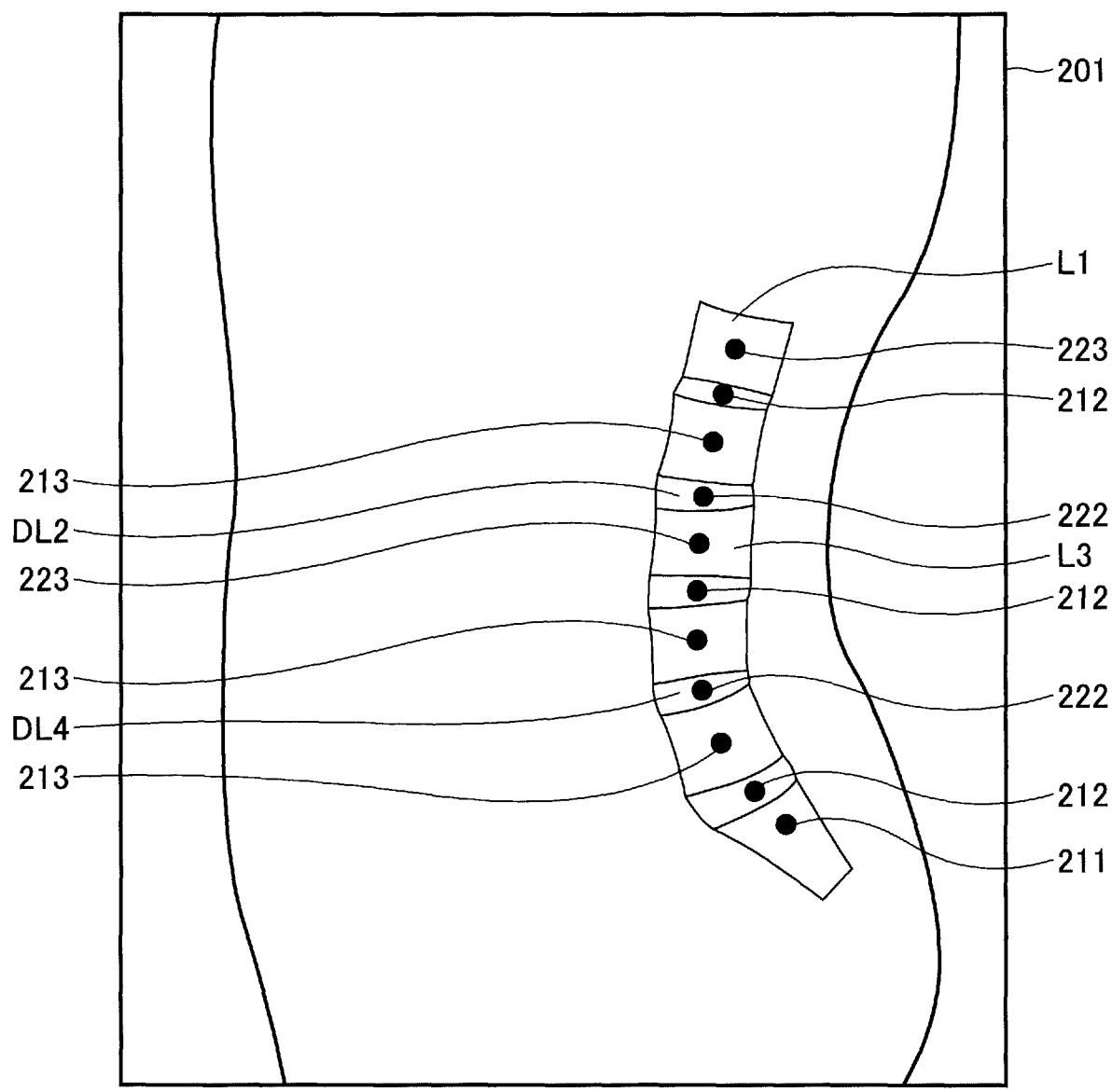
FIG. 7M is a diagram (thirteenth example) illustrating a method of processing a medical image including a sacrum.

By repeating such a process, as illustrated in FIG. 7M, labeling is executed for all of the parts. Note that in the example illustrated in FIG. 7M, assume that the first lumbar vertebra L1 and the third lumbar vertebra L3 are not detected, for which interpolation points 223 are set; the intervertebral disk DL4 is not detected, for which the interpolation point 222 is set; and although the intervertebral disk DL2 has been detected, but the detection point does not satisfy the angle condition, and hence, an interpolation point 222 is set.

Figure 9:
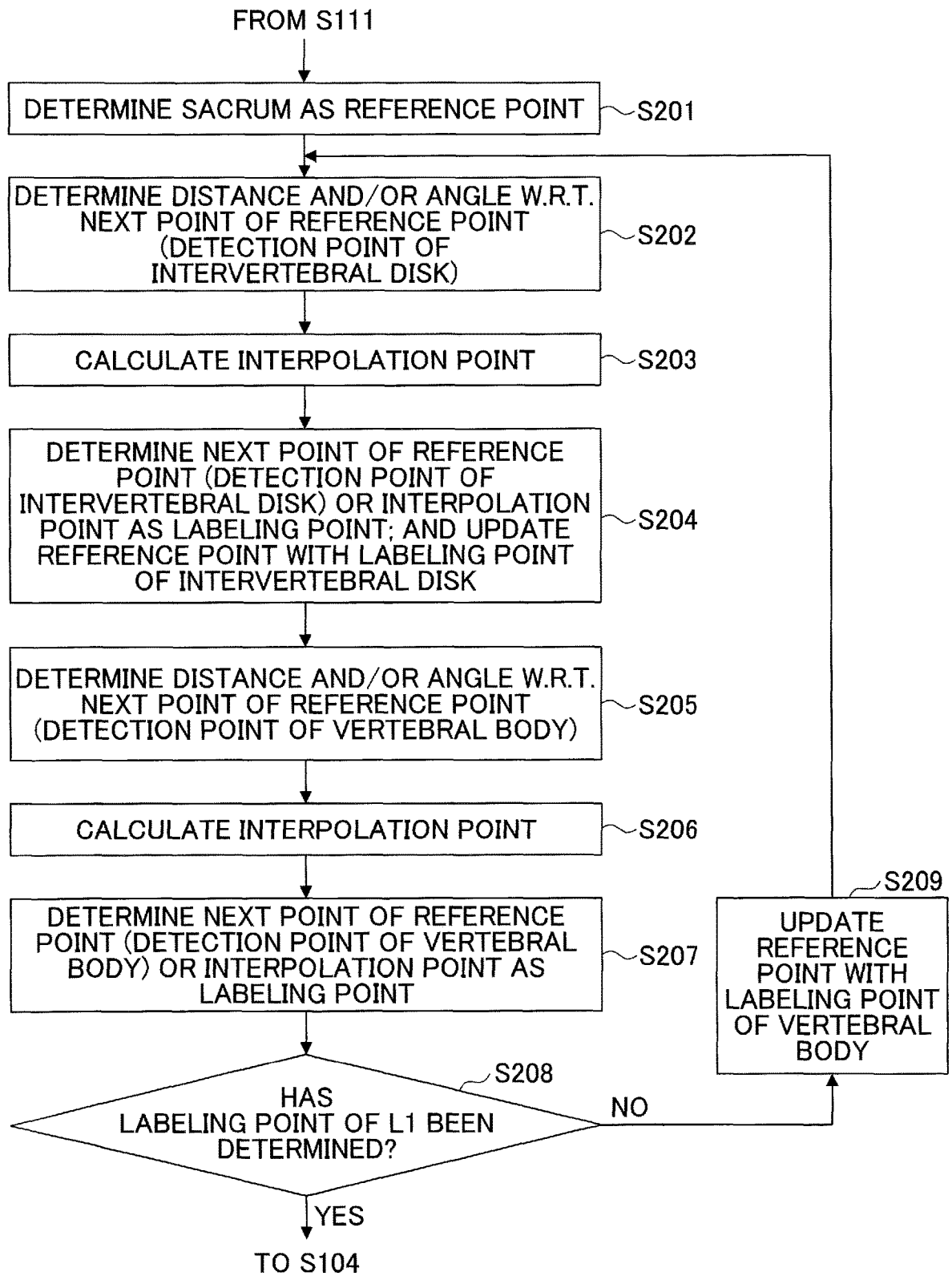
FIG. 9 is a flowchart illustrating a labeling process of a lumbar vertebra.

Such a labeling process of the lumbar vertebrae (Step S103) can be illustrated as a flowchart in FIG. 9. In other words, after generation of an approximate curve (Step S111), the detection point of a sacrum is determined as the first reference point (Step S201). Next, it is determined whether the distance condition and/or the angle condition with respect to the next point of the reference point (the detection point of the intervertebral disk) are satisfied (Step S202), and if either of the conditions is not satisfied, an interpolation point is calculated (Step S203). Then, the next point (the detection point of the intervertebral disk) or the interpolation point of the current reference point is determined as the labeling point, and the reference point is updated with this determined labeling point of the intervertebral disk (Step S204). Thereafter, it is determined whether the distance condition and/or the angle condition with respect to the next point of the current reference point (the detection point of the vertebral body) are satisfied (Step S205), and if either of the conditions is not satisfied, an interpolation point is calculated (Step S206). Then, the next point of the current reference point (the detection point of the vertebral body) or the interpolation point is determined as the labeling point (Step S207). Next, it is determined whether the labeling point of the first lumbar vertebra L1 has been determined (Step S208), and if not determined, the reference point is updated with the labeling point of the vertebral body determined most recently (Step S209), and the process returns to Step S202.

Next, examples of displays of labeling results will be described. FIGS. 10A to 10F are diagrams illustrating examples of displays of labeling results.

Figure 10A:
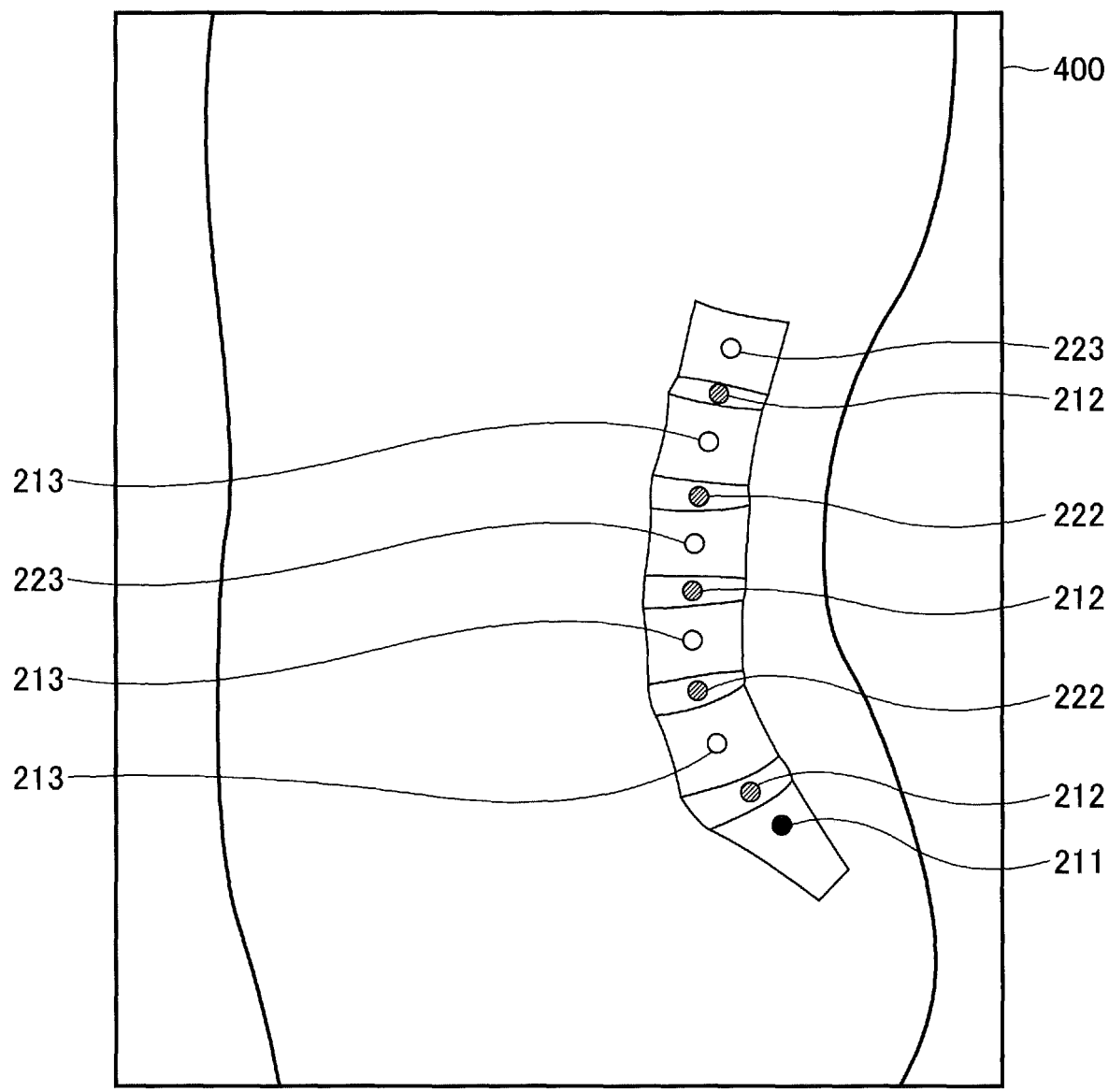
FIG. 10A is a diagram illustrating an example (first example) of a display of a result of labeling.

In the example illustrated in FIG. 10A, on a screen 400 of the display 105, the labeling point of a sacrum, the labeling points of lumbar vertebrae, and the labeling points of intervertebral disks are displayed in colors different from each other.

Figure 10B:
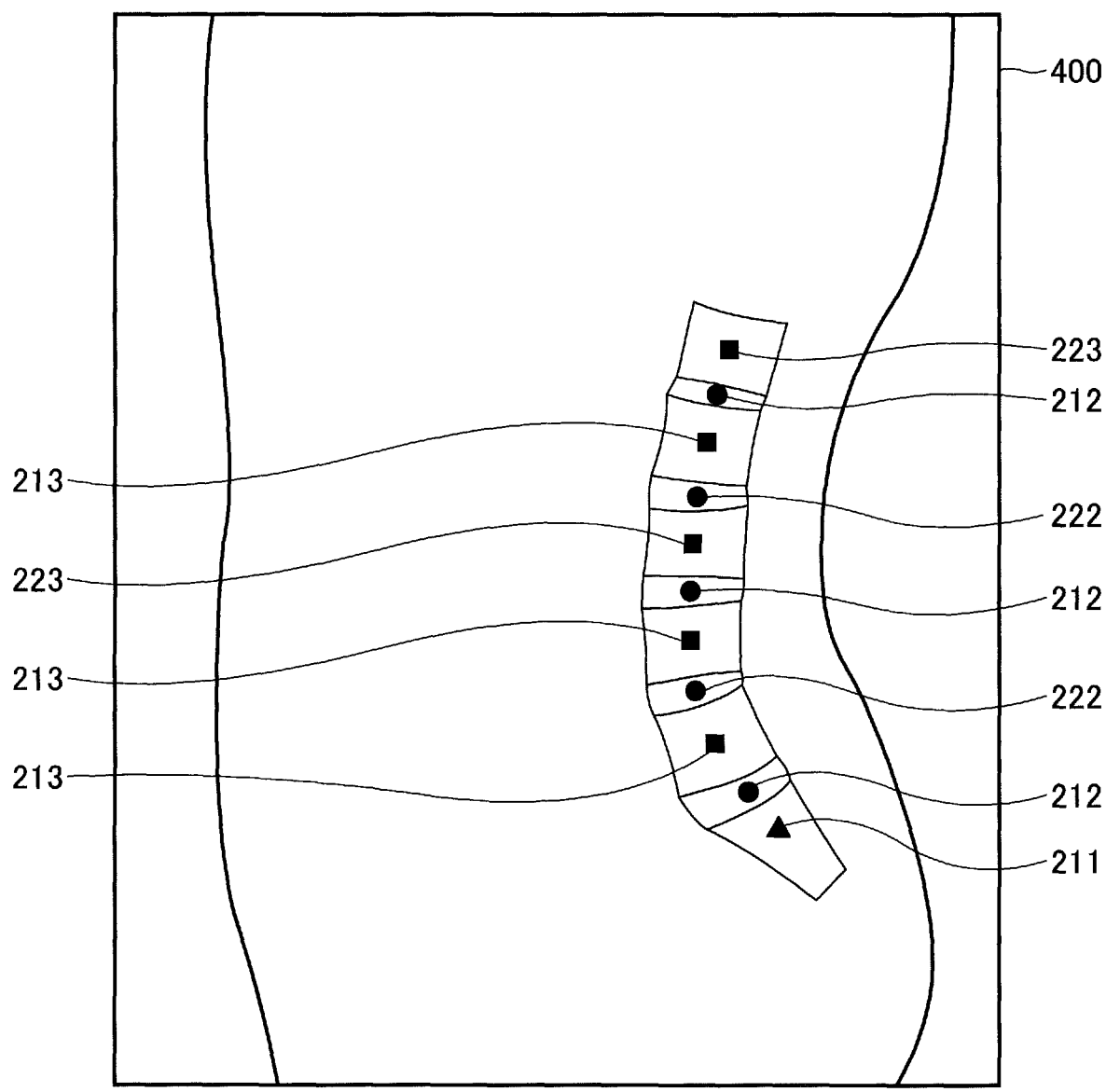
FIG. 10B is a diagram illustrating an example (second example) of a display of a result of labeling.

In the example illustrated in FIG. 10B, on the screen 400 of the display 105, the labeling point of the sacrum, the labeling points of the lumbar vertebrae, and the labeling points of the intervertebral disks are displayed in shapes different from each other.

Figure 10C:
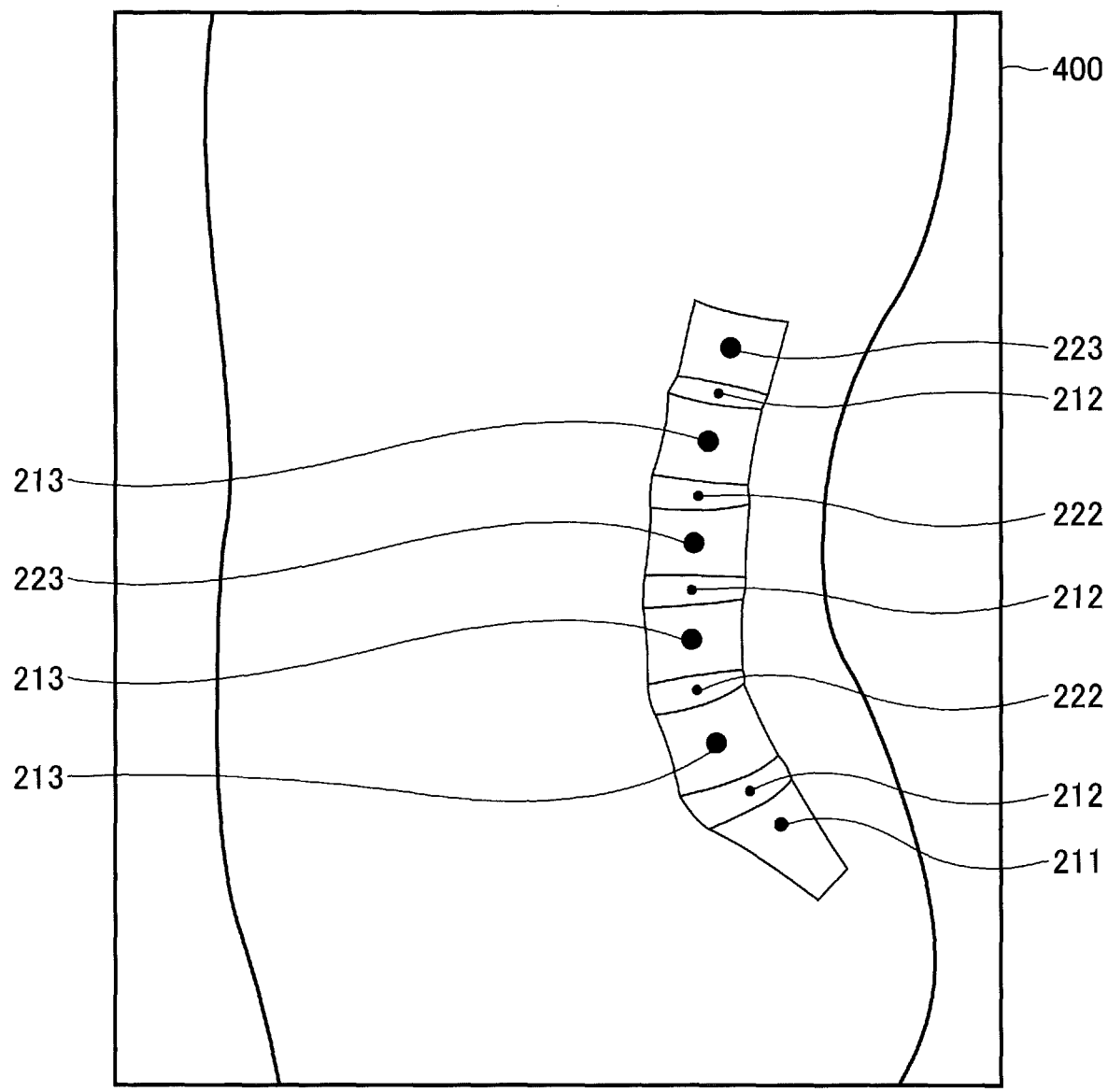
FIG. 10C is a diagram illustrating an example (third example) of labeling result display.

In the example illustrated in FIG. 10C, on the screen 400 of the display 105, the labeling point of the sacrum, the labeling points of the lumbar vertebrae, and the labeling points of the intervertebral disks are displayed in sizes different from each other.

Figure 10D:
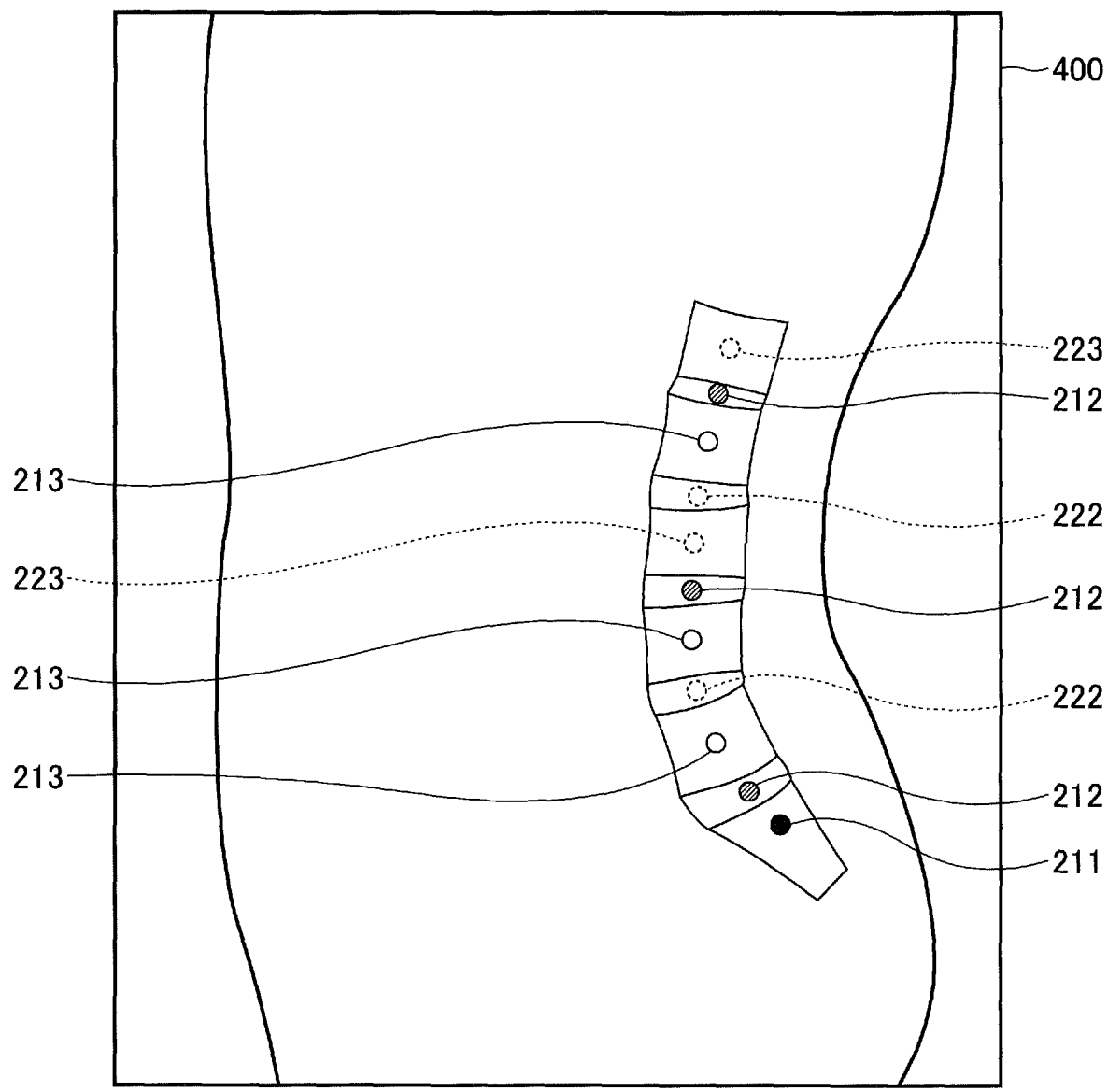
FIG. 10D is a diagram illustrating an example (fourth example) of a display of a result of labeling.

In the example illustrated in FIG. 10D, on the screen 400 of the display 105, the labeling point of the sacrum, the labeling points of the lumbar vertebrae, and the labeling points of the intervertebral disks are displayed in colors different from each other, and the interpolation points are displayed with blinking.

Figure 10E:
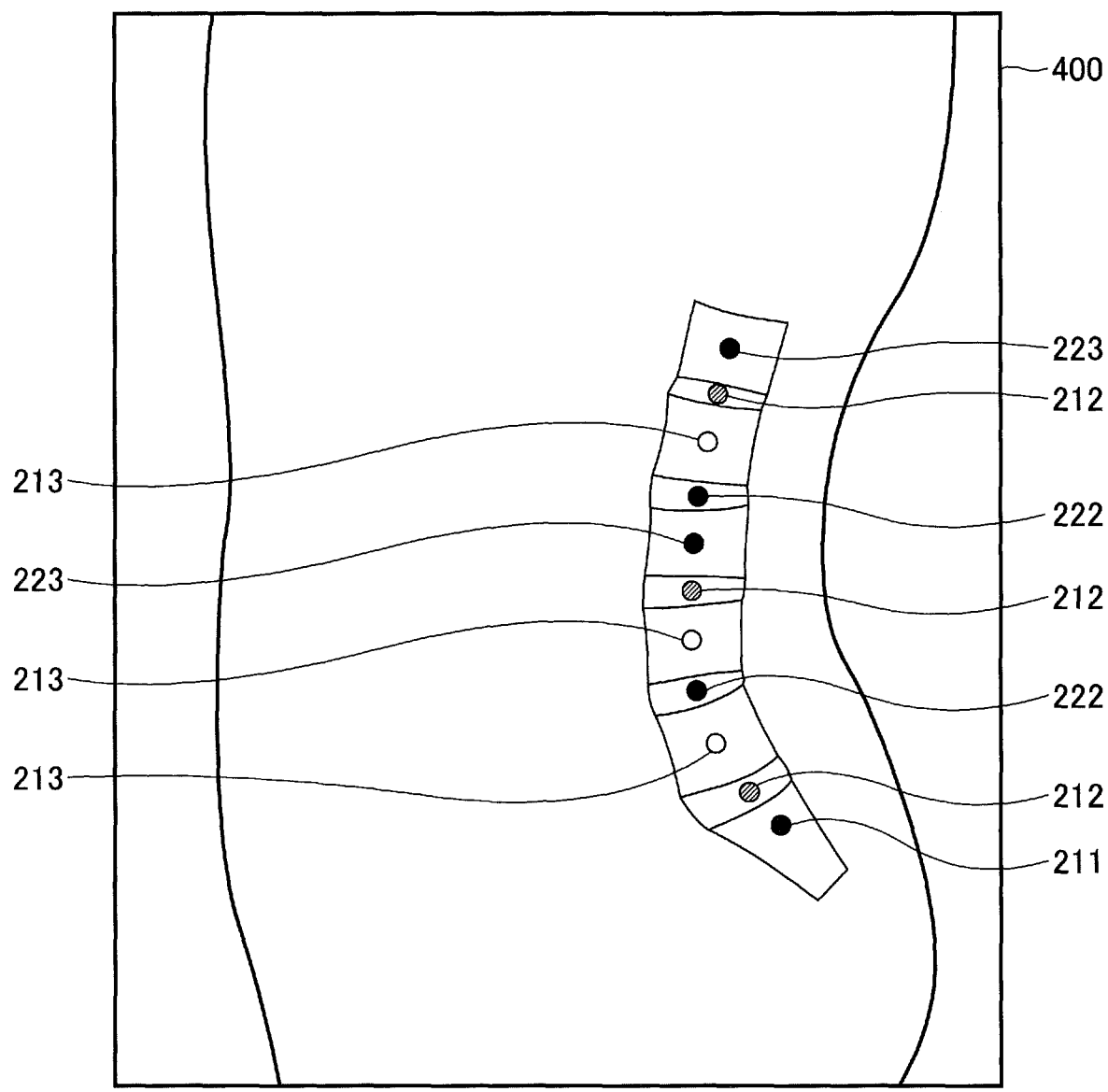
FIG. 10E is a diagram illustrating an example (fifth example) of a display of a result of labeling.

In the example illustrated in FIG. 10E, on the screen 400 of the display 105, the labeling point of the sacrum, the labeling points of the lumbar vertebrae, and the labeling points of the intervertebral disks are displayed in colors different from each other, and further, the interpolation points are displayed in a different color, for example, in black.

Figure 10F:
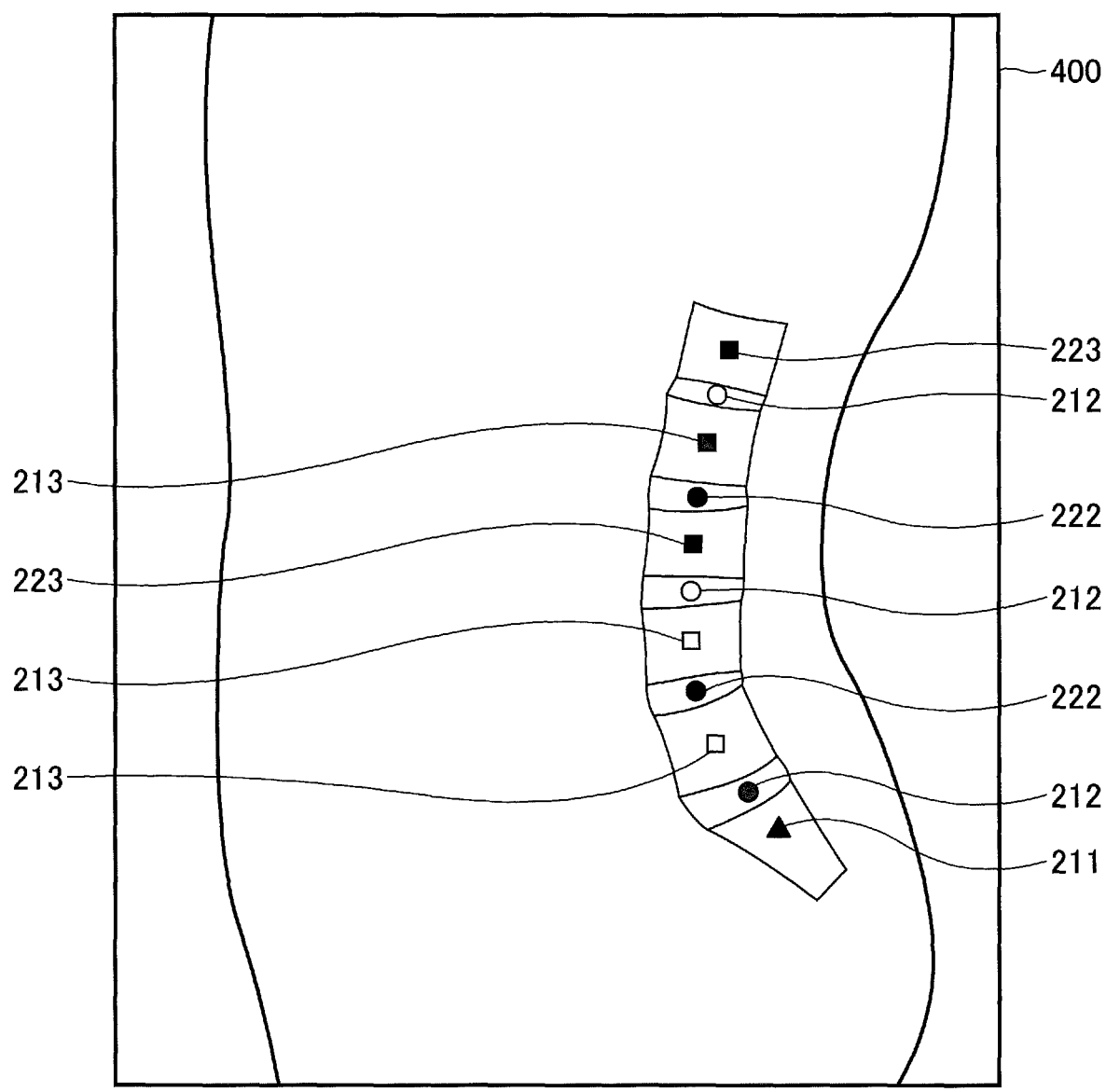
FIG. 10F is a diagram illustrating an example (sixth example) of a display of a result of labeling.

In the example illustrated in FIG. 10F, on the screen 400 of the display 105, the labeling point of the sacrum, the labeling points of the lumbar vertebrae, and the labeling points of the intervertebral disks are displayed in shapes different from each other, and further, a color depending on the reliability is attached to each labeling point.

In this way, the display form of a labeling result is not limited, which can be changed in terms of the color, shape, size, blinking, etc. of each mark. Display control is executed by the display controller 155.

Next, another specific example of operations of the medical image processing apparatus 100 will be described. FIGS. 11A to 11J are diagrams illustrating methods of processing a medical image including a second cervical vertebra.

Figure 11A:
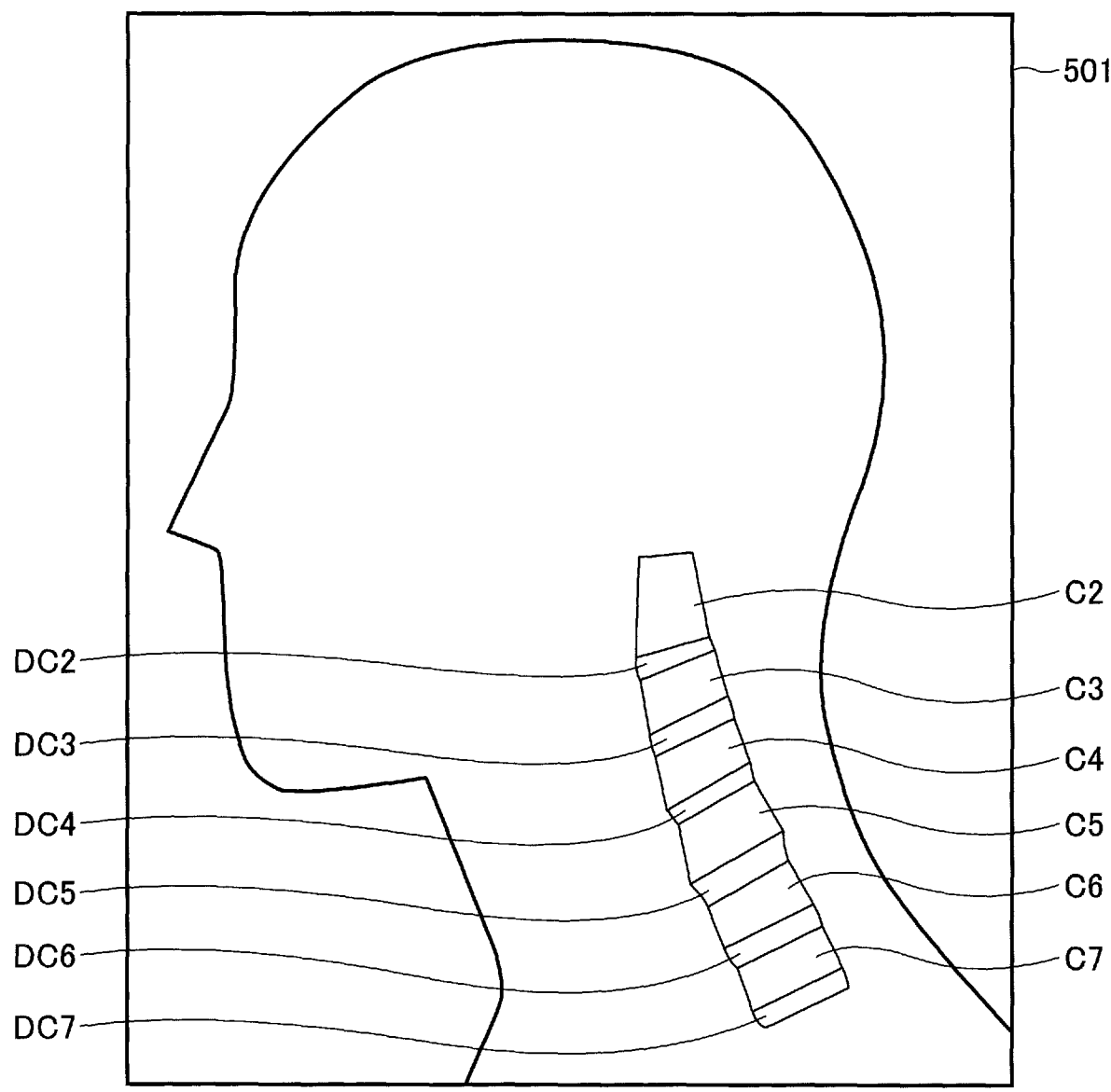
FIG. 11A is a diagram (first example) illustrating a method of processing a medical image including a second cervical vertebra.

In this example, as illustrated in FIG. 11A, assume that a medical image 501 is used in which a second cervical vertebra C2, a third cervical vertebra C3, a fourth cervical vertebra C4, a fifth cervical vertebra C5, a sixth cervical vertebra C6, and a seventh cervical vertebra C7 are imaged. There is an intervertebral disk DC2 between the second cervical vertebra C2 and the third cervical vertebra C3; there is an intervertebral disk DC3 between the third cervical vertebra C3 and the fourth cervical vertebrate C4; there is an intervertebral disk DC4 between the fourth cervical vertebra C4 and the fifth cervical vertebra C5; there is an intervertebral disk DC5 between the fifth cervical vertebra C5 and the sixth cervical vertebra C6; there is an intervertebral disk DC6 between the sixth cervical vertebra C6 and the seventh cervical vertebra C7; and there is an intervertebral disk DC7 under the seventh cervical vertebra C7. The data of the medical image 501 is obtained by the obtainer 151.

Figure 11B:
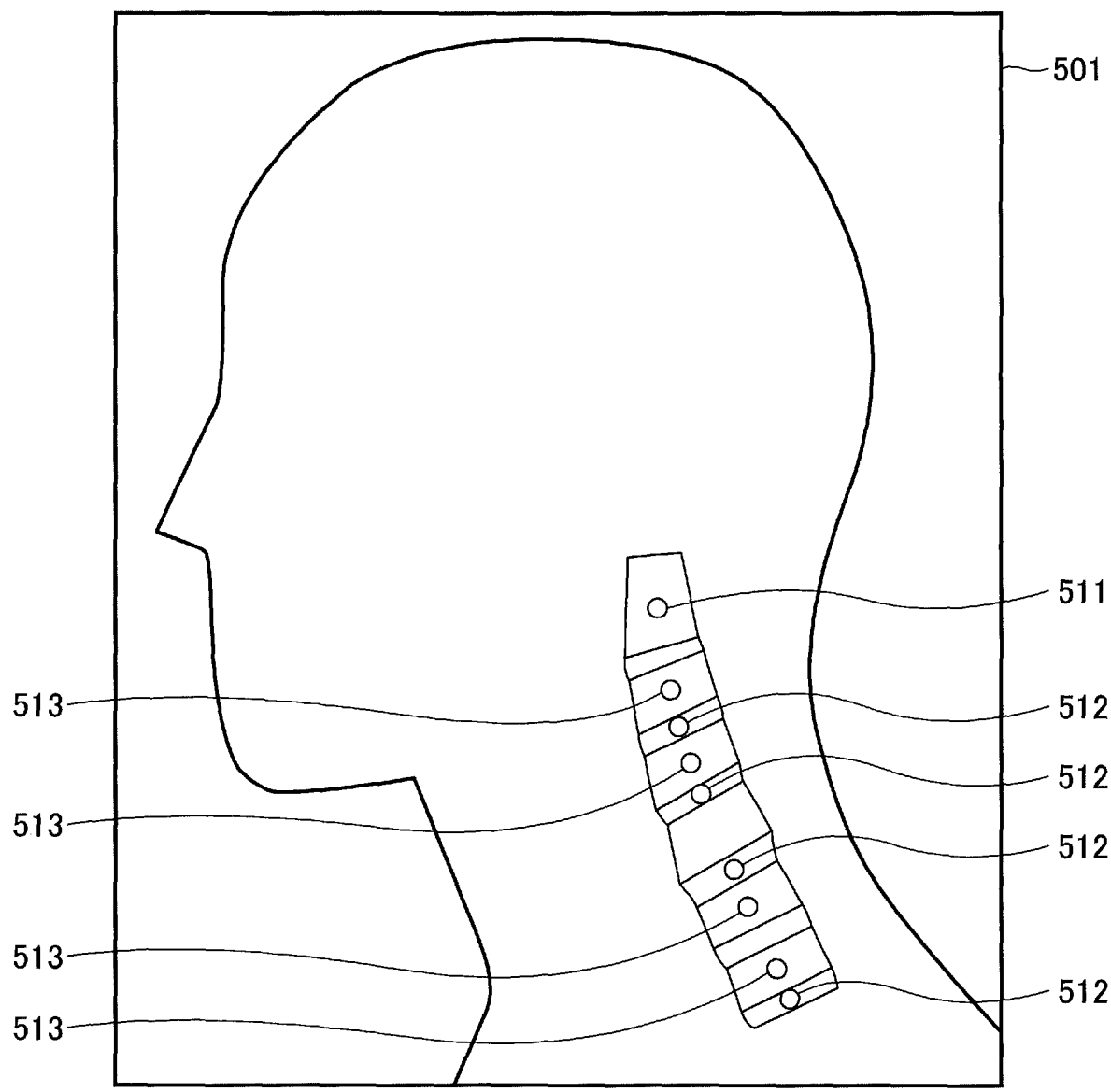
FIG. 11B is a diagram (second example) illustrating a method of processing a medical image including a second cervical vertebra.

The detector 152 attempts to detect the second cervical vertebra C2, the third cervical vertebra C3, the fourth cervical vertebra C4, the fifth cervical vertebra C5, the sixth cervical vertebra C6, the seventh cervical vertebra C7, the intervertebral disk DC2, the intervertebral disk DC3, the intervertebral disk DC4, the intervertebral disk DC5, the intervertebral disk DC6, and the intervertebral disk DC7, and then, determines the detection points for the parts that have been detected. In this example, as illustrated in FIG. 11B, assume that a detection point 511 of the second cervical vertebra C2 has been determined, detection points 512 have been determined for a part of the intervertebral disks, and detection points 513 have determined for a part of the cervical vertebrae; however, detection points could not be detected for another part of the intervertebral disks and another part of the cervical vertebrae.

Figure 11C:
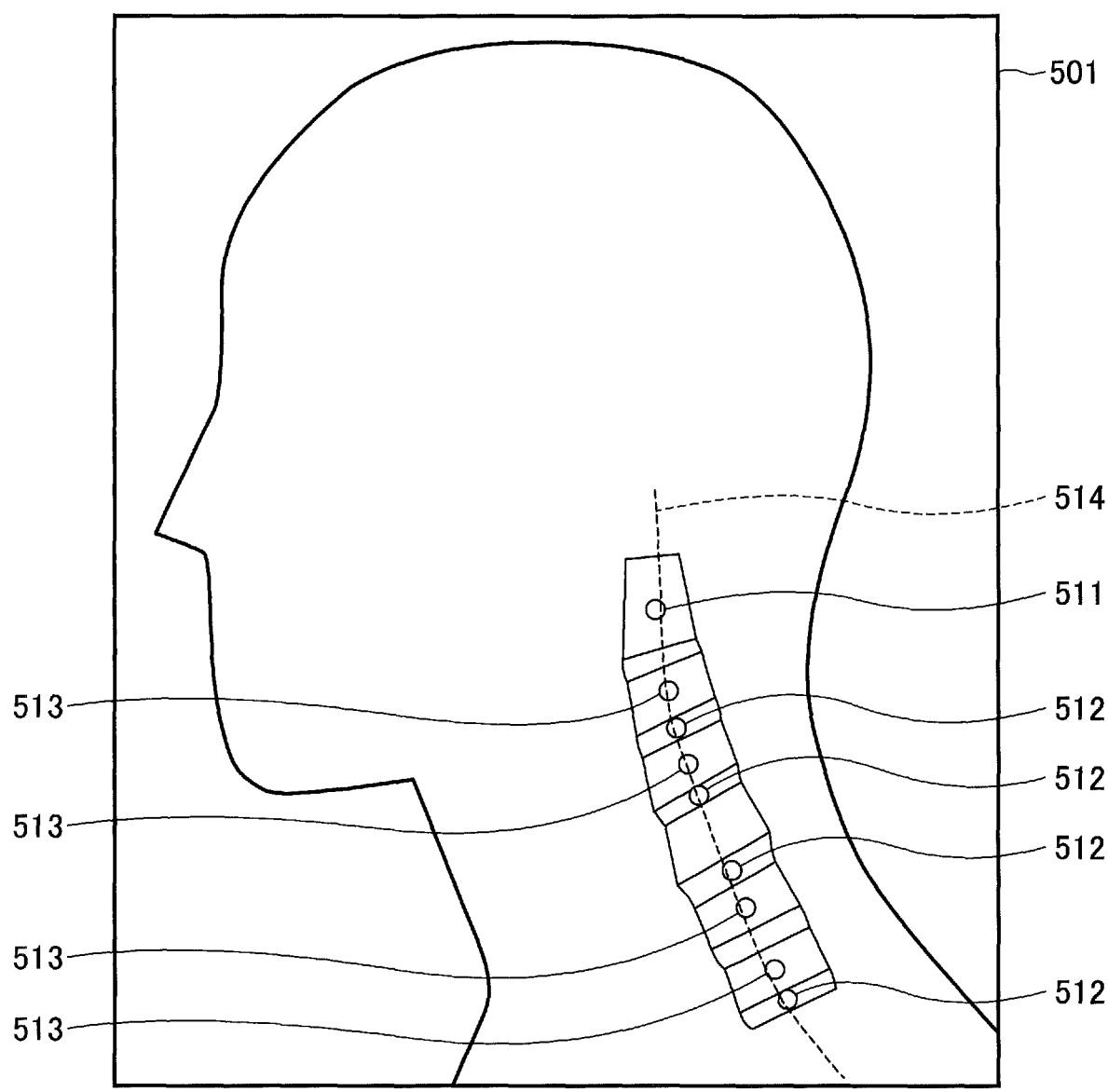
FIG. 11C is a diagram (third example) illustrating a method of processing a medical image including a second cervical vertebra.

As illustrated in FIG. 11C, the approximate curve generator 161 of the labeler 153 generates an approximate curve 514 of a group of line segments connecting the detection points 511, 512 and 513 determined by the detector 152.

Figure 11D:
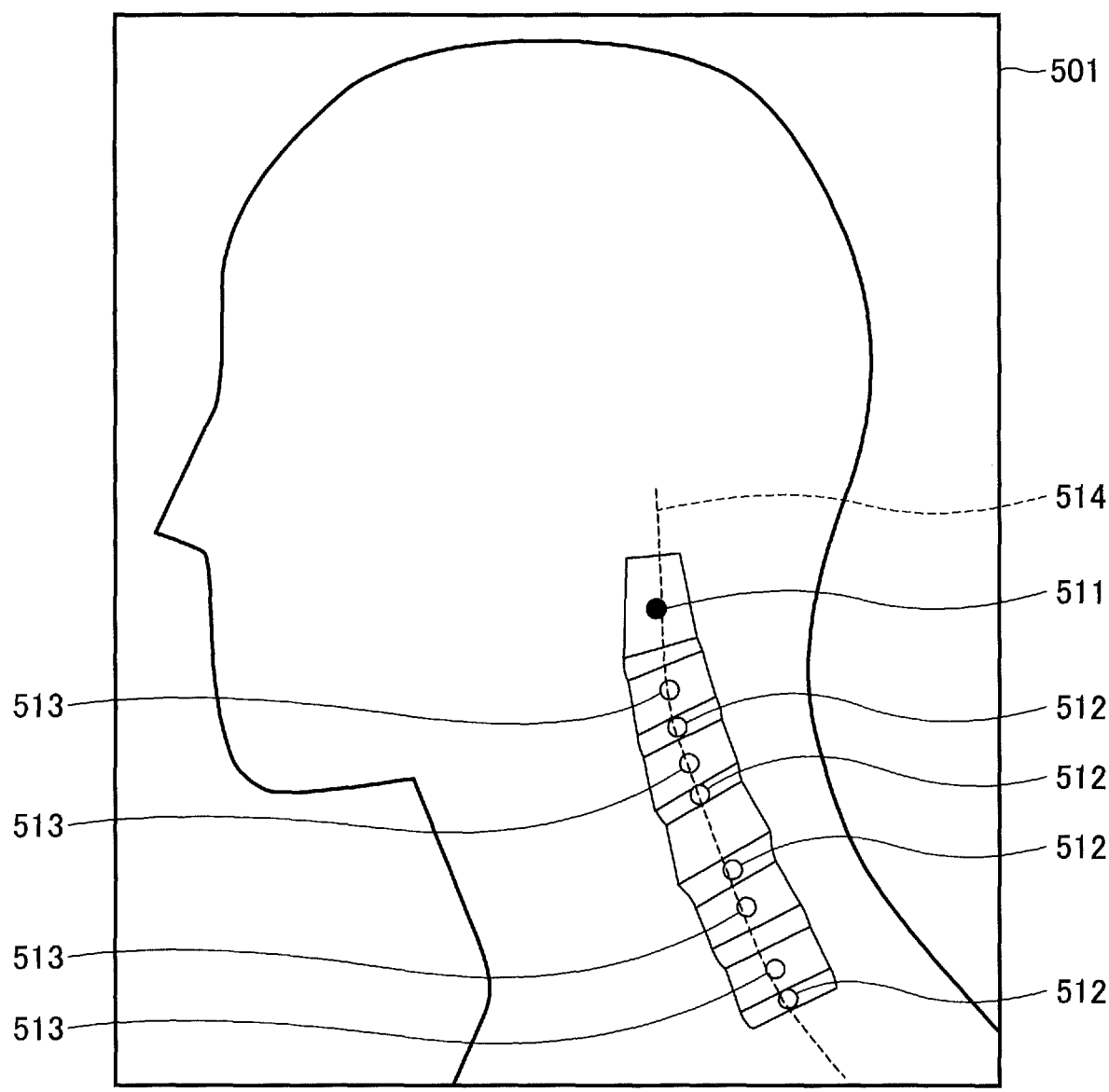
FIG. 11D is a diagram (fourth example) illustrating a method of processing a medical image including a second cervical vertebra.

As illustrated in FIG. 11D, the reference point determiner 162 of the labeler 153 determines a first reference point from among the detection points 511, 512, and 513 determined by the detector 152. In this example, the detection point 511 of the second cervical vertebra C2 is determined as the first reference point.

Figure 11E:
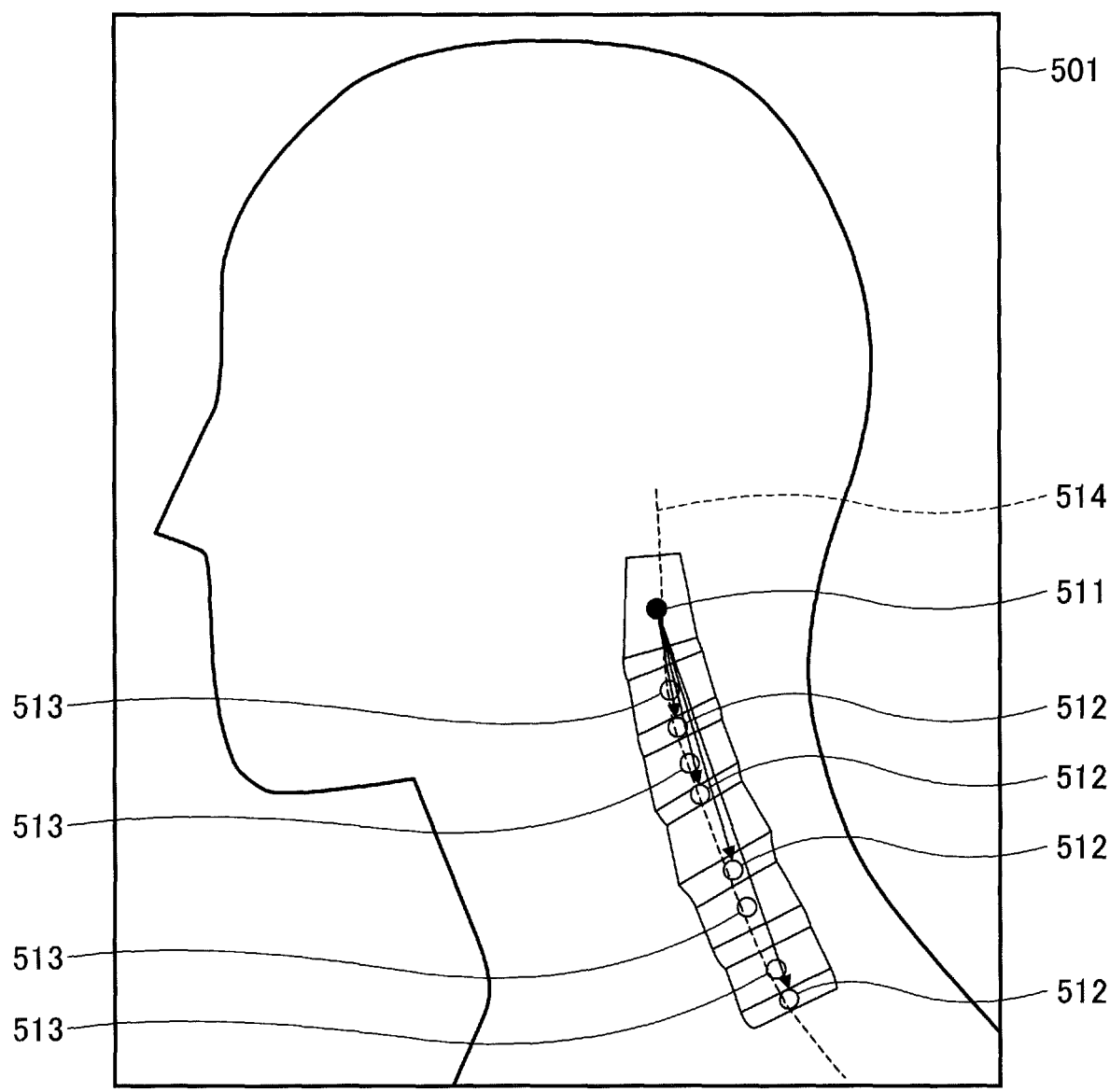
FIG. 11E is a diagram (fifth example) illustrating a method of processing a medical image including a second cervical vertebra.

As illustrated in FIG. 11E, since the current reference point is the second cervical vertebra C2, the next point determiner 163 of the labeler 153 determines multiple detection points 512 of the intervertebral disks as candidates for the next point.

Figure 11F:
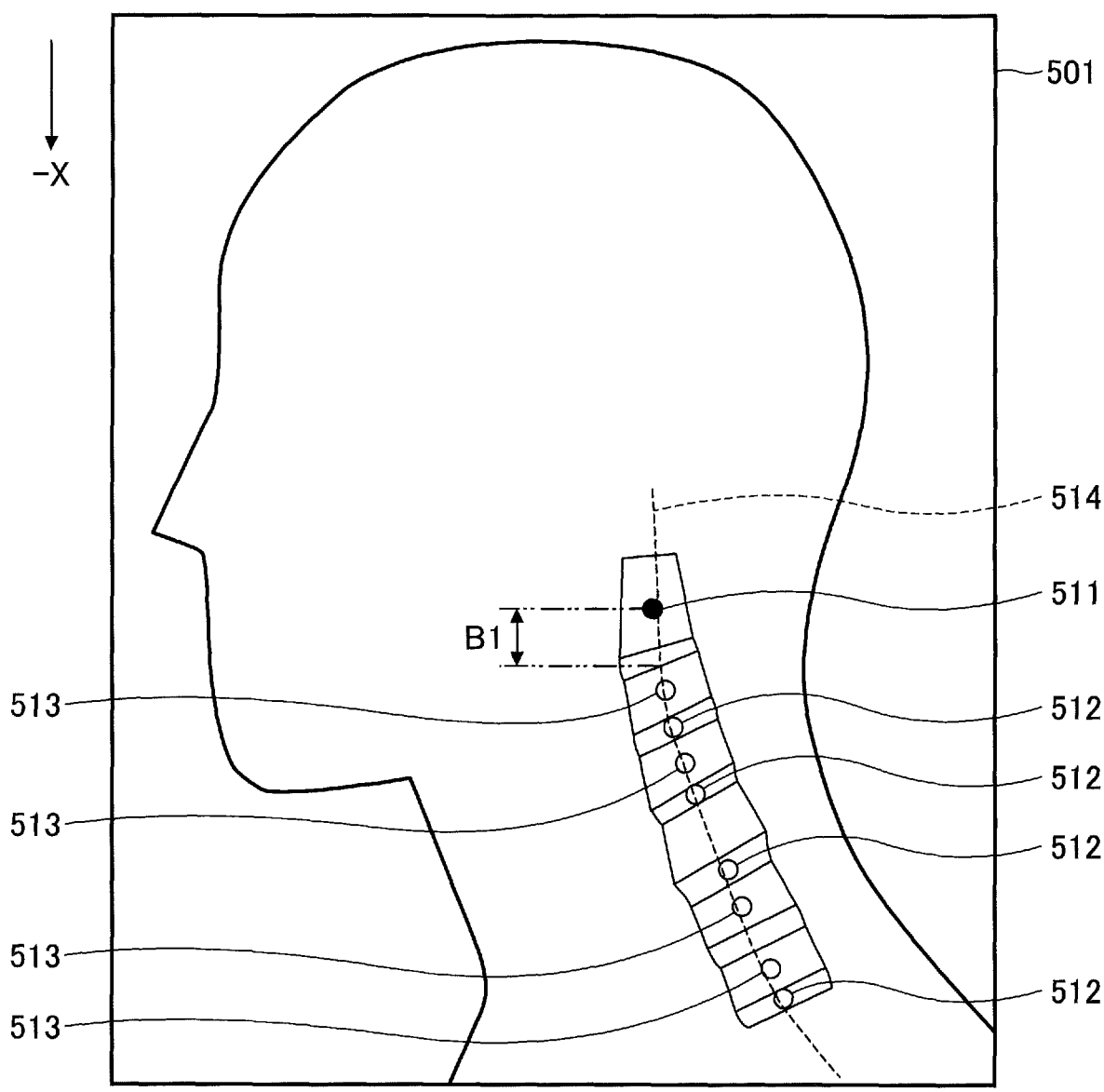
FIG. 11F is a diagram (sixth example) illustrating a method of processing a medical image including a second cervical vertebra.
Figure 11G:
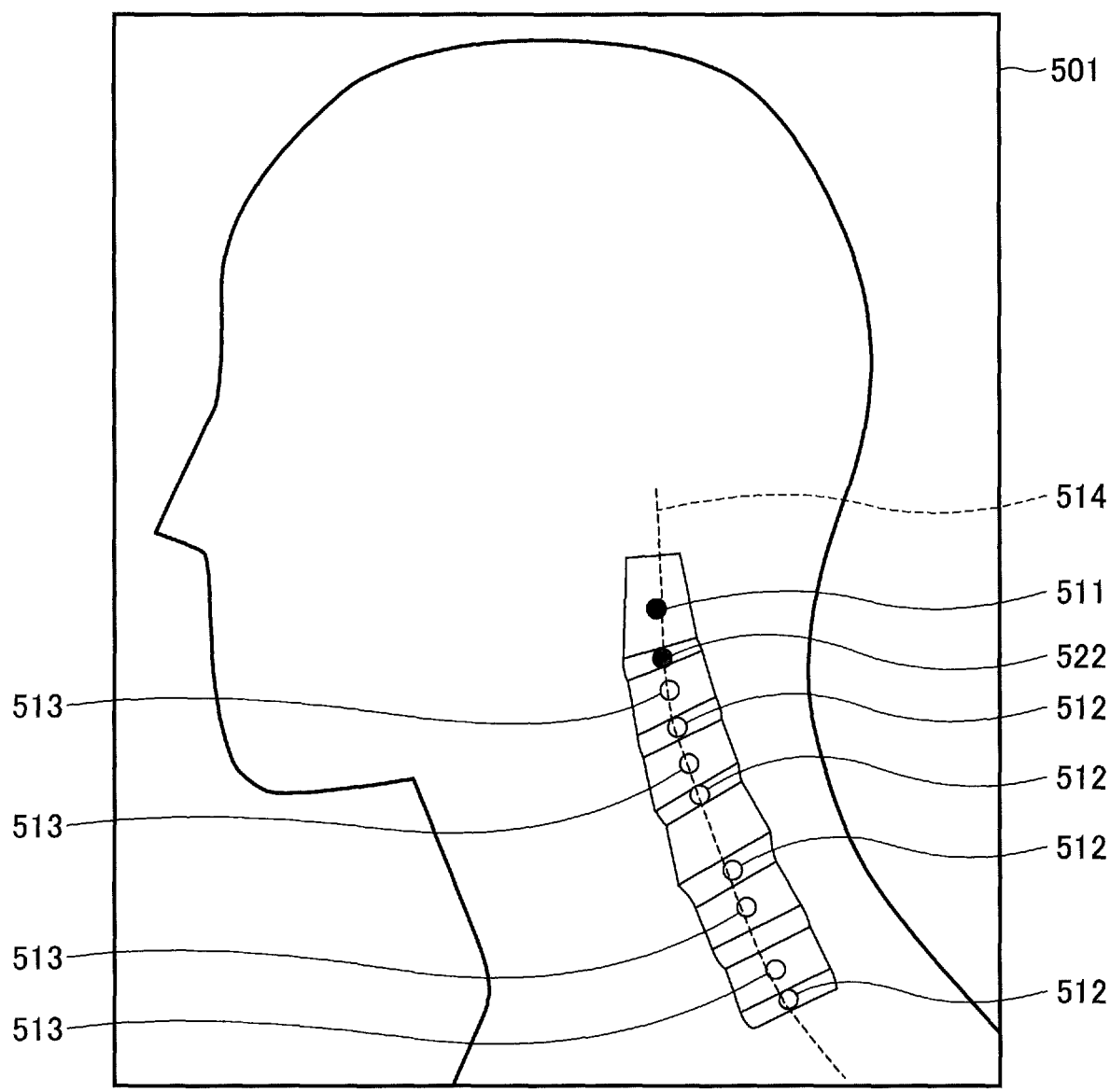
FIG. 11G is a diagram (seventh example) illustrating a method of processing a medical image including a second cervical vertebra.
Figure 11H:
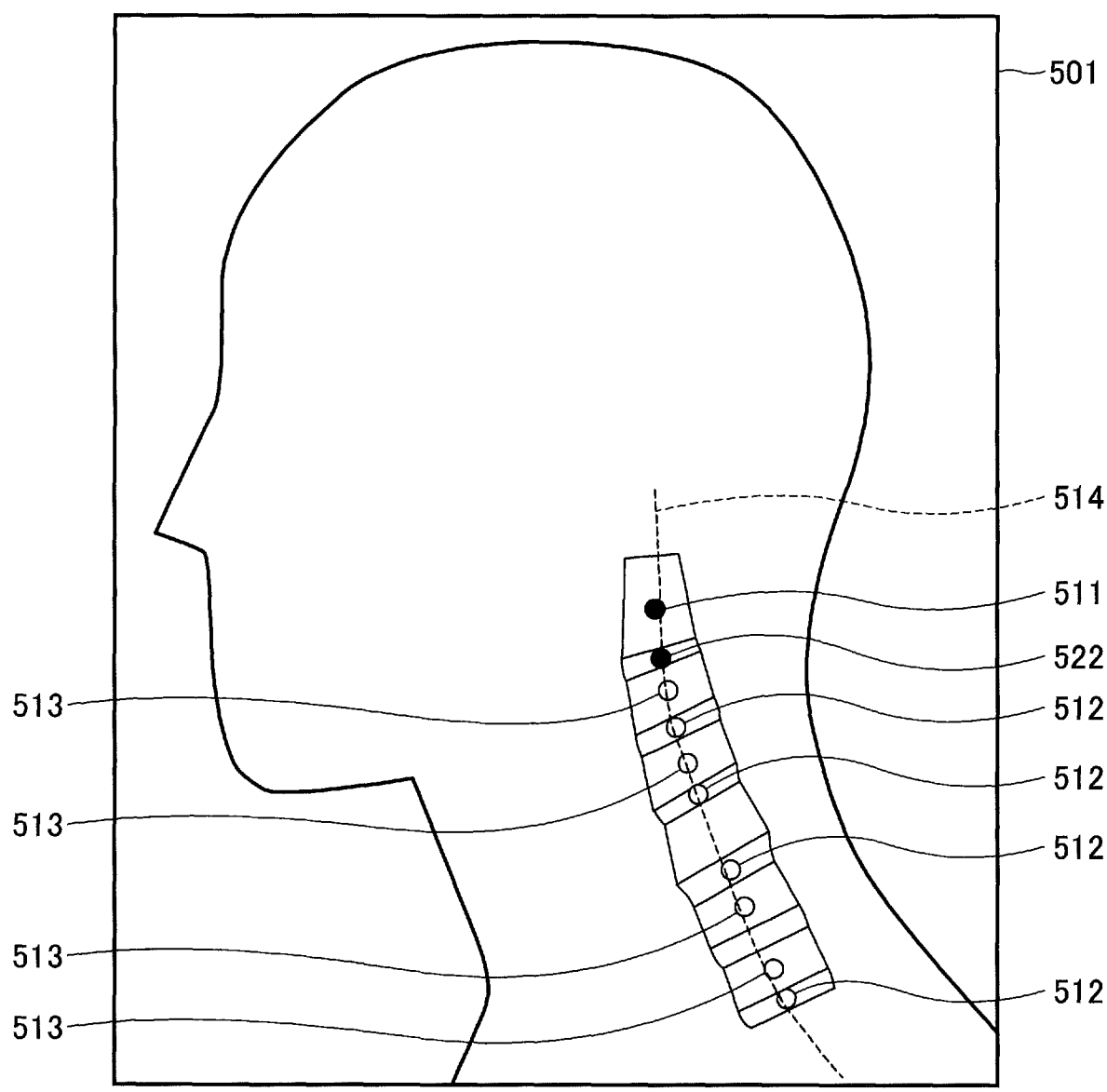
FIG. 11H is a diagram (eighth) illustrating a method of processing a medical image including a second cervical vertebra.

Then, the next point determiner 163 determines whether there is a detection point that satisfies a predetermined distance condition with respect to the second cervical vertebra C2 among the multiple detection points 512 of the intervertebral disks. For example, as illustrated in FIG. 11F, in a certain direction (−X direction), the next point determiner 163 determines whether there is a detection point whose distance from the detection point 511 is less than or equal to an interpolation distance B1 predetermined with respect to the second cervical vertebra C2. Here, assume that the intervertebral disk DC2 is not detected. In this case, there is no detection point whose distance in the −X direction is less than or equal to the interpolation distance B1. Therefore, as illustrated in FIG. 11G, the interpolation point calculator 171 calculates an interpolation point 522 of the intervertebral disk DC2. Then, as illustrated in FIG. 11H, the next point determiner 163 sets the interpolation point 522 of the intervertebral disk DC2 as the labeling point of the intervertebral disk DC2, and sets it as the next reference point.

Figure 11I:
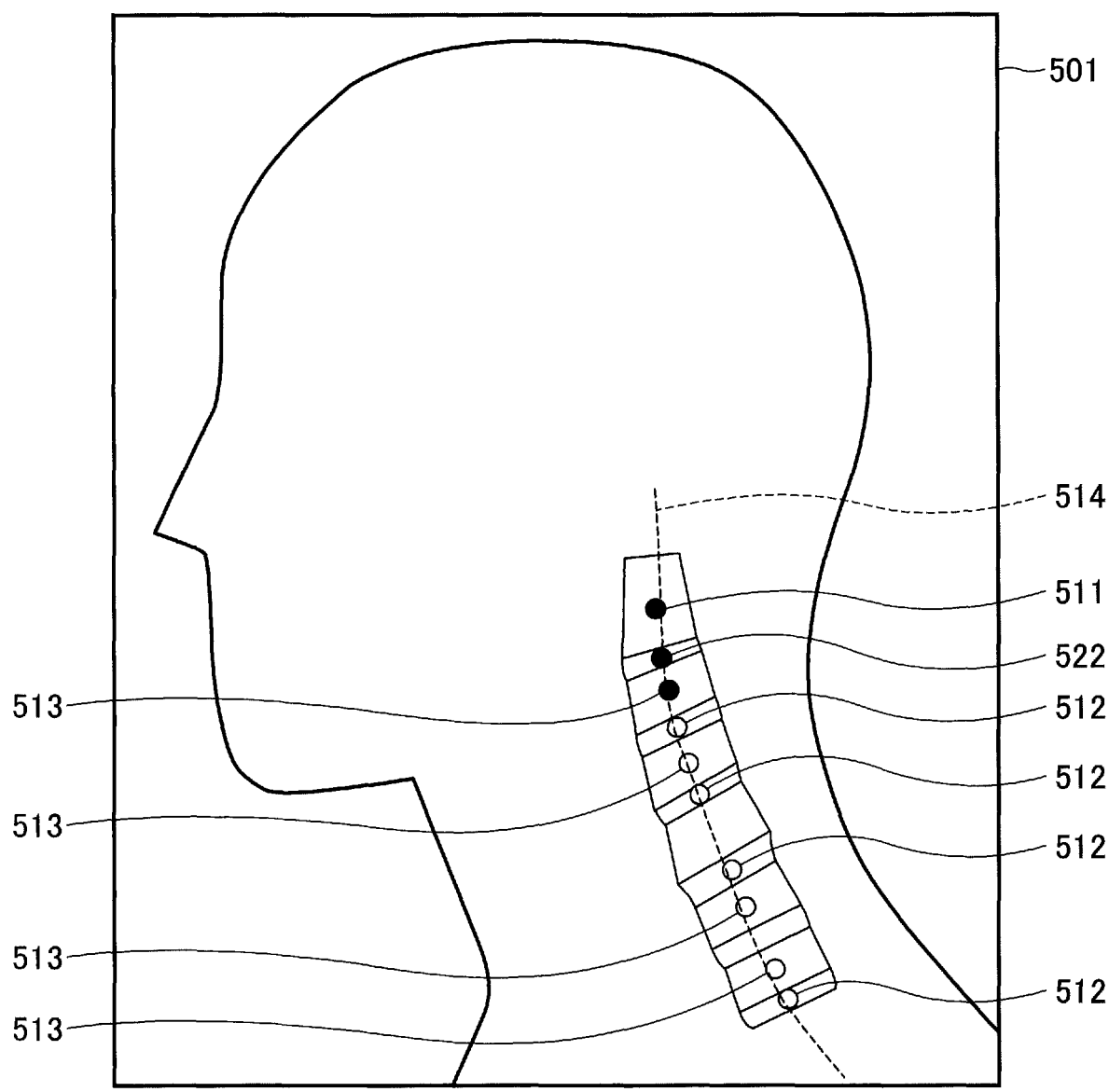
FIG. 11I is a diagram (ninth) illustrating a method of processing a medical image including a second cervical vertebra.

Next, the next point determiner 163 executes a similar process with the interpolation point 522 of the intervertebral disk DC2 as the reference point. Then, in this example, as illustrated in FIG. 11I, assume that the detection point 513 of the third cervical vertebra C3 as it is is set as the labeling point of the third cervical vertebra C3.

Figure 11J:
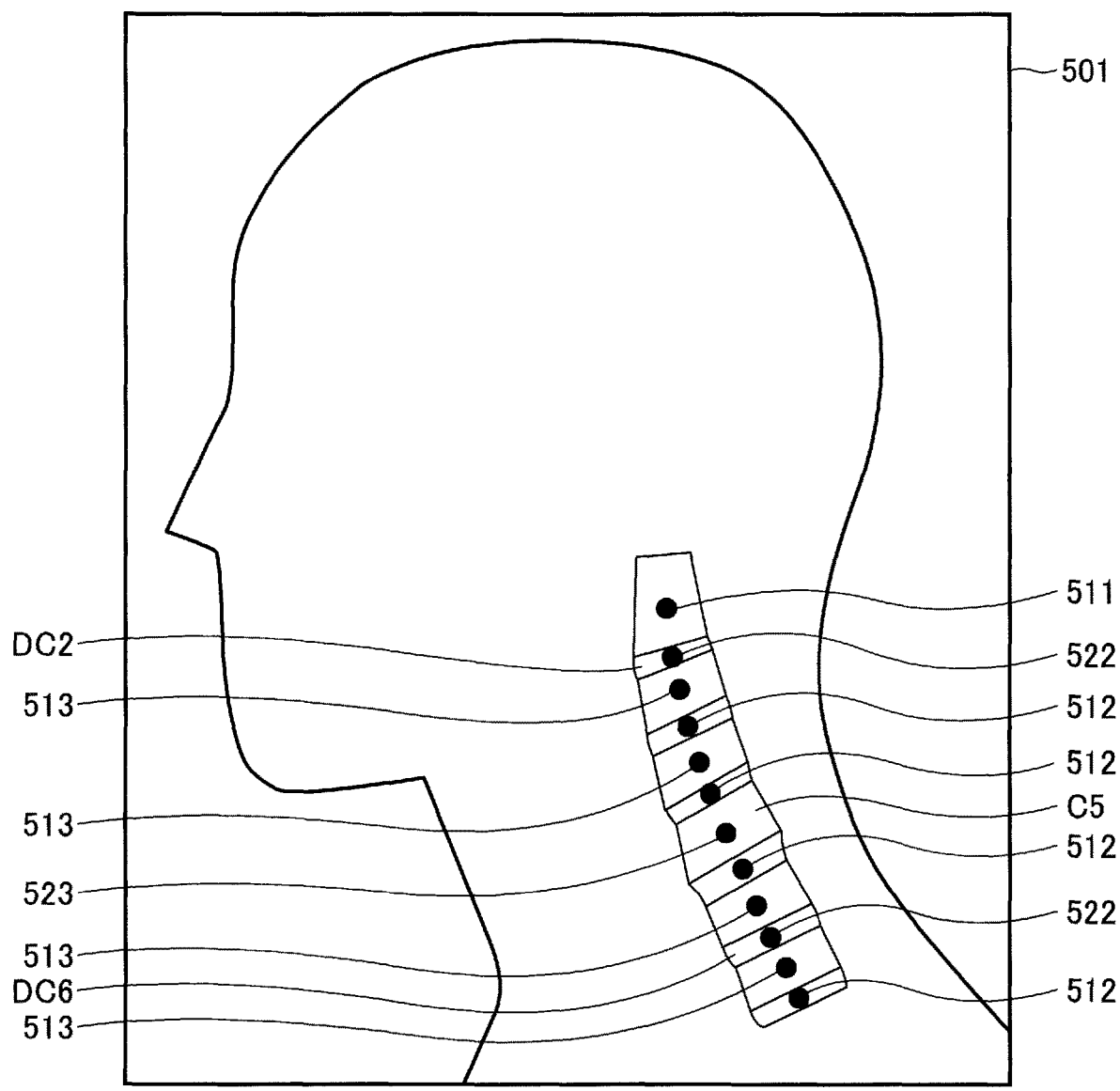
FIG. 11J is a diagram (tenth) illustrating a method of processing a medical image including a second cervical vertebra.

By repeating such a process, as illustrated in FIG. 11J, labeling is executed for all of the parts. Note that in the example illustrated in FIG. 11J, assume that the fifth cervical vertebra C5 is not detected, to which the interpolation point 523 is set, and the intervertebral disk DC2 and the intervertebral disk DC6 are not detected, to which the interpolation points 522 are set.

Figure 12:
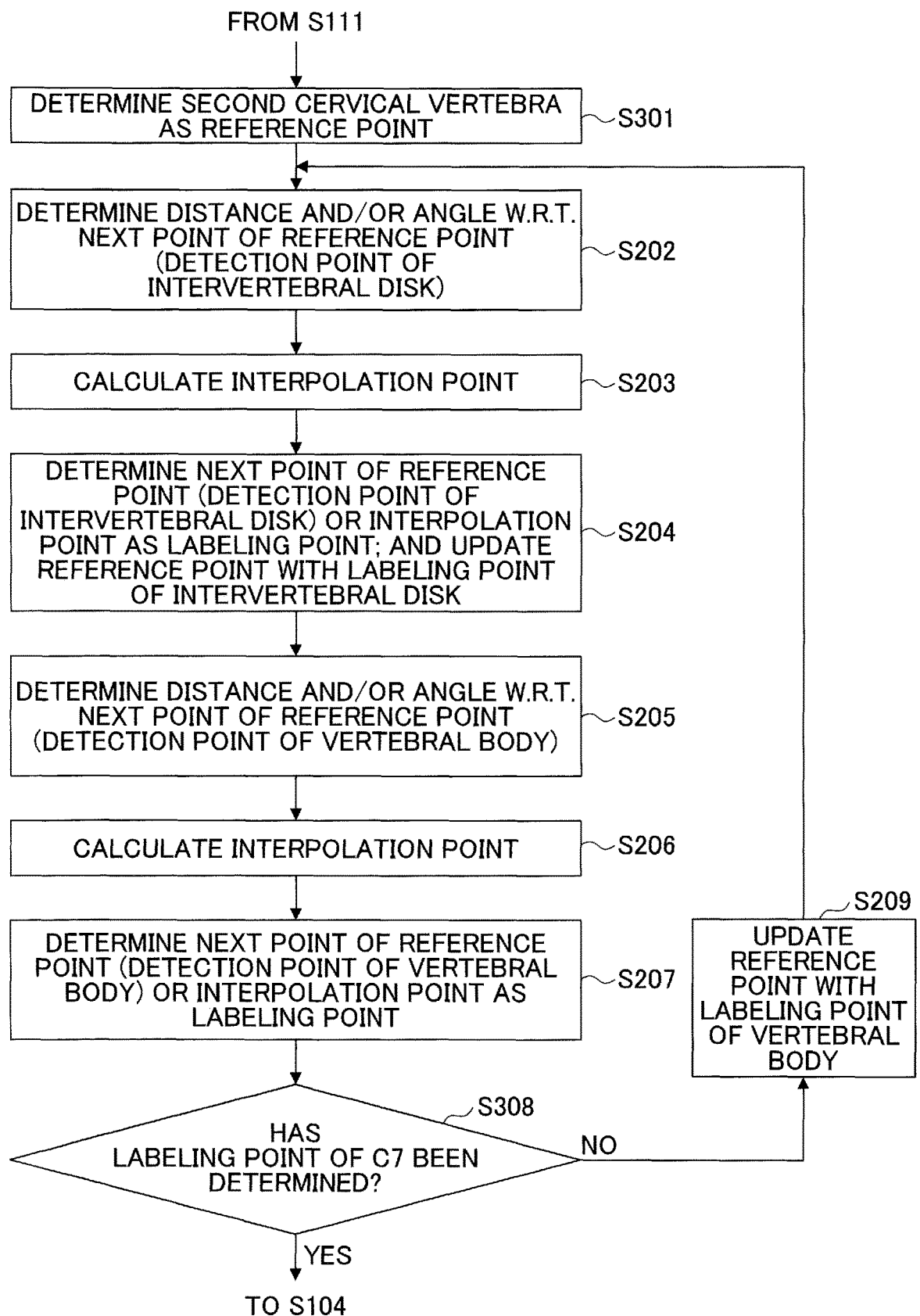
FIG. 12 is a flowchart illustrating a labeling process of cervical vertebrae.
Figure 13B:
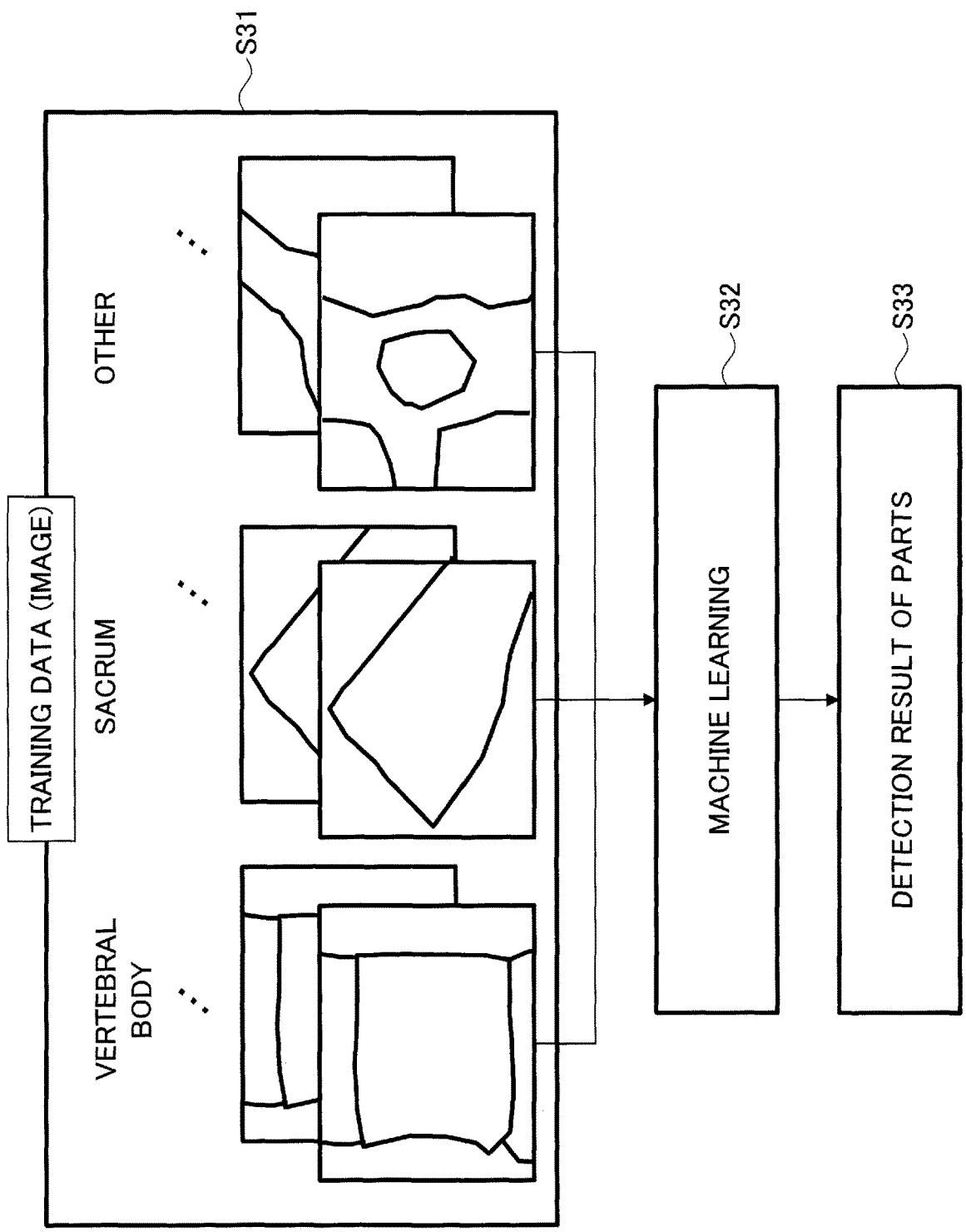
FIG. 13B is a flowchart (second example) illustrating a process of learning and detection executed by a detector.
Figure 13C:
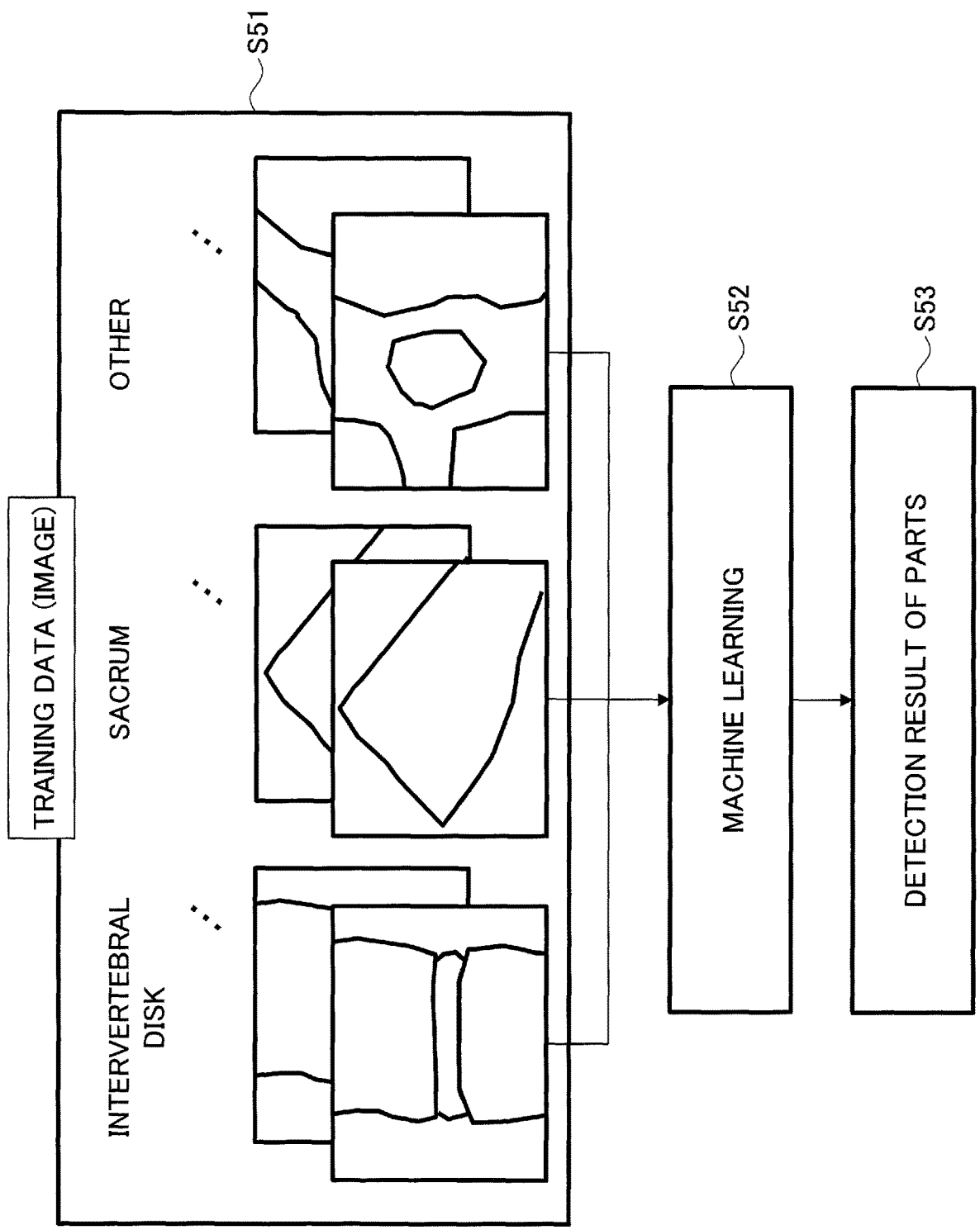
FIG. 13C is a flowchart (third example) illustrating a process of learning and detection executed by a detector.
Figure 13D:
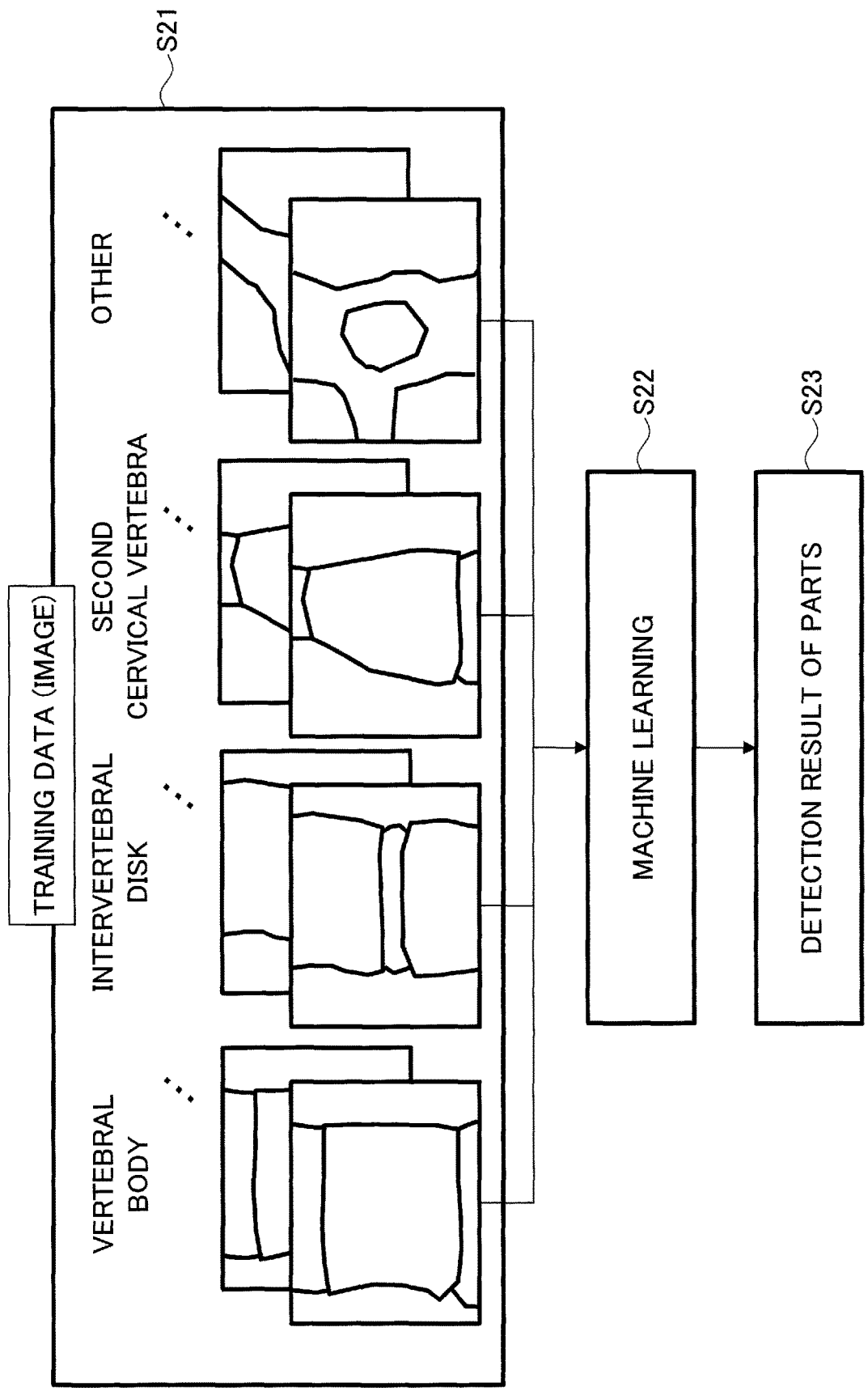
FIG. 13D is a flowchart (fourth) illustrating a process of learning and detection executed by a detector.
Figure 13E:
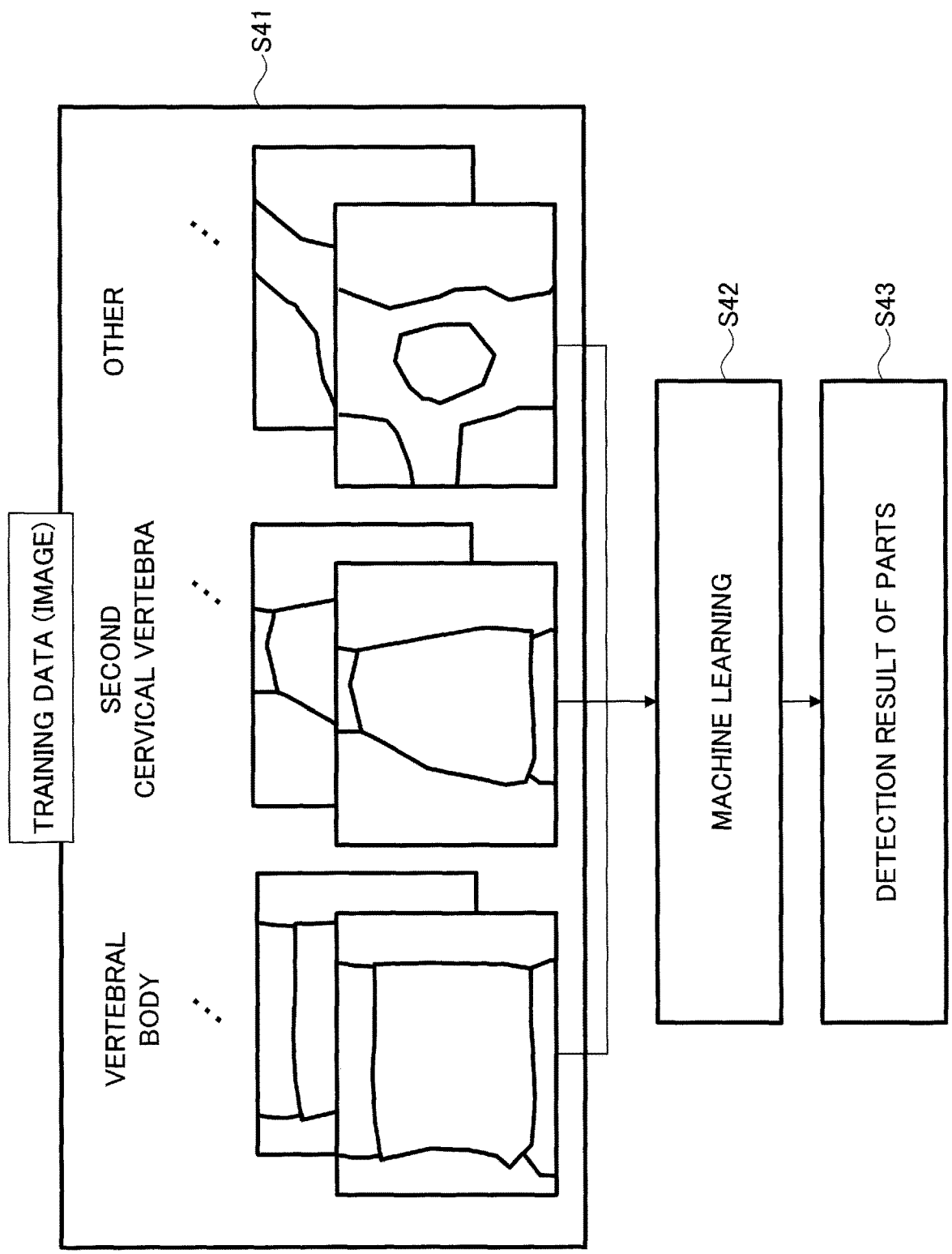
FIG. 13E is a flowchart (fifth example) illustrating a process of learning and detection executed by a detector.
Figure 13F:
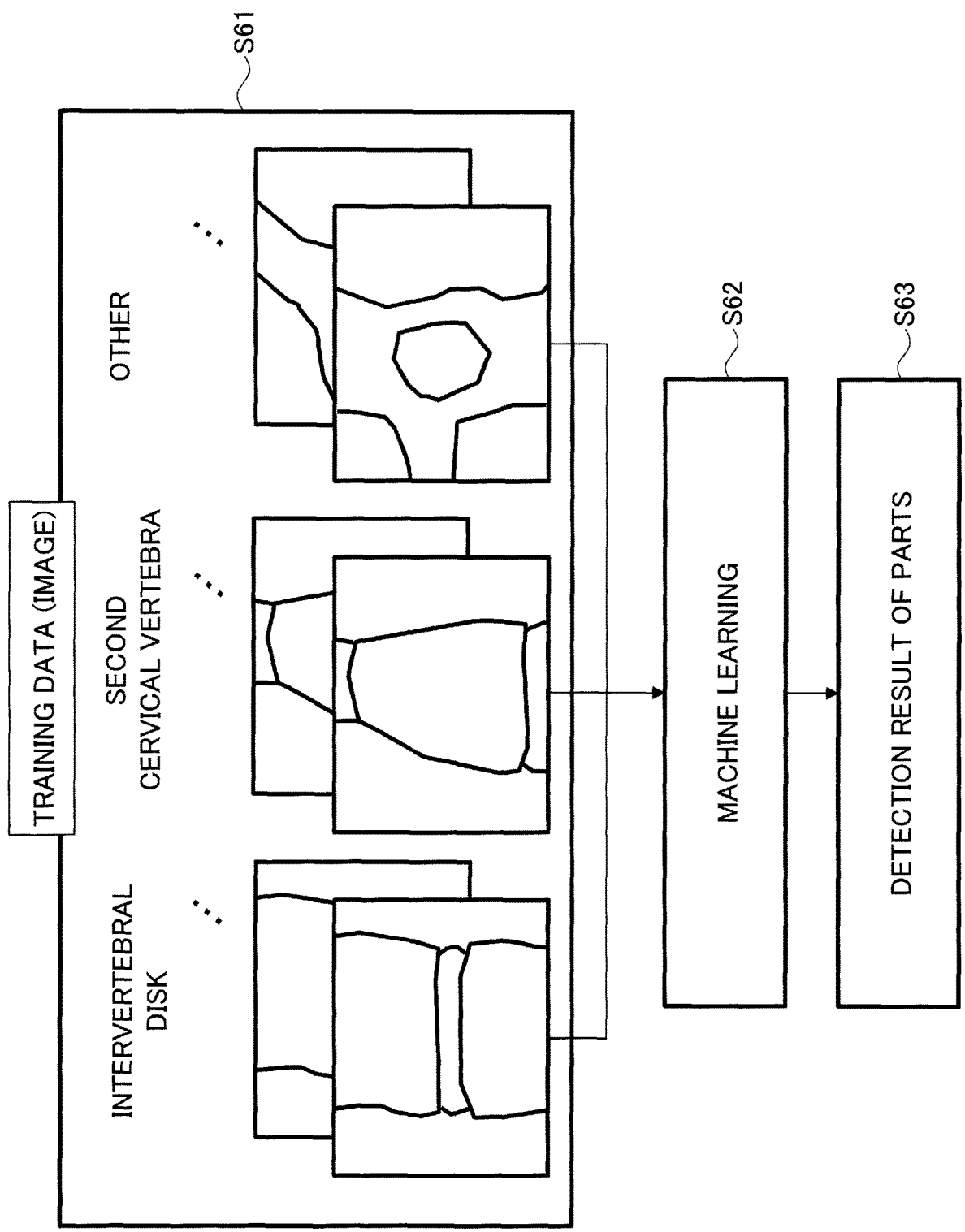
FIG. 13F is a flowchart (sixth example) illustrating a process of learning and detection executed by a detector.

Such a labeling process of the cervical vertebrae (Step S103) can be illustrated as a flowchart in FIG. 12. In other words, after generation of an approximate curve (Step S111), the detection point of the second cervical vertebra is determined as the first reference point (Step S301). Next, it is determined whether the distance condition and/or the angle condition with respect to the next point of the reference point (the detection point of the intervertebral disk) are satisfied (Step S202), and if either of the conditions is not satisfied, an interpolation point is calculated S203). Then, the next point of the current reference point (the detection point of the intervertebral disk) or the interpolation point is determined as the labeling point, and the reference point is updated with this determined labeling point of the intervertebral disk (Step S204). Thereafter, it is determined whether the distance condition and/or angle condition with respect to the next point of the current reference point (the detection point of the vertebral body) is satisfied (Step S205), and if either of the conditions is not satisfied, an interpolation point is calculated (Step S206). Then, the next point of the current reference point (the detection point of the vertebral body) or the interpolation point is determined as the labeling point (Step S207). Next, it is determined whether the labeling point of the seventh cervical vertebra C7 has been determined (Step S208), and if not determined, the reference point is updated with the labeling point of the vertebral body determined most recently (Step S209), and the process returns to Step S202. If the labeling point of the seventh cervical vertebra C7 has been determined, labeling may be executed for the intervertebral disk DC7.

Here, examples of methods of learning for causing the detector 152 to detect respective parts will be described. FIGS. 13A to 13F are flowcharts illustrating processes of learning and detection executed by the detector 152.

First, parts to be detected are cut out from a medical image, to generate training data (image) (Steps S11, S21, S31, S41, S51, and S61). As the training data (image), for example, an image is used in which two or more of the vertebral bodies, intervertebral disks, sacrums, and second cervical vertebrae are included, and other parts are included. In the example illustrated in FIG. 13A, the training data (image) includes vertebral bodies, intervertebral disks, sacrums, and other parts. In the example illustrated in FIG. 13B, the training data (image) includes vertebral bodies, sacrums, and other parts. In the example illustrated in FIG. 13C, the training data (image) includes intervertebral disks, sacrums, and other parts. In the example illustrated in FIG. 13D, the training data (image) includes vertebral bodies, intervertebral disks, second cervical vertebrae, and other parts. In the example illustrated in FIG. 13E, the training data (image) includes vertebral bodies, second cervical vertebrae, and other parts. In the example illustrated in FIG. 13F, the training data (image) includes intervertebral disks, second cervical vertebrae, and other parts.

Also, an image obtained by applying a preprocess to generated training data (image) may be used as the training data (image). For example, data augmentation may be applied in order to increase the number of items of training data (images) and to set them as the training data (images), in which an image is rotated or reversed; the resolution or size of an image is changed; the degree of blur is changed; the amount of noise is changed; and/or the like. As for augmentation by rotation, with a notation of representing (angle in the clockwise direction: angle in the counterclockwise direction: increment of rotation angle), the augmentation may be executed for an image of vertebral bodies by (30 degrees: 60 degrees: 5 degrees); for an image of intervertebral disks by (40 degrees: 60 degrees: 10 degrees); for an image of sacrums by (30 degrees: 60 degrees: 10 degrees); for an image of parts other than the above three parts by (5 degrees: 5 degrees: 1 degree); and the like. As for augmentation in the size, the augmentation may be executed to set the vertical width of the rectangular area to be cut=the vertical width of the cut rectangular area×(1, 1.1, 1.2); the horizontal width of the rectangular area to be cut=the horizontal width of the cut rectangular area×1, 1.1, 1.2, 1.3); and the like. If image processing is applied to training data (image), processes such as contrast flattening and/or edge enhancement may be applied.

Next, machine learning is executed (Steps S12, S22, S32, S42, S52, and S62). In the machine learning, labels are assigned to two or more of the vertebral bodies, the intervertebral disks, the sacrums, and the second cervical vertebrae; and other parts included in the generated training data (image), to generate a detector. This detector can be used as the detector 152. Also, the number of items of training data (images) to be learned may be changed for each part. For example, in a batch of learning, a method may be adopted to set the ratios of (vertebral bodies):(intervertebral disks): (sacrums):(other than vertebral bodies, intervertebral disks, and sacrums)=0.30:0.30:0.10:0.30.

Then, when detecting the parts from the medical image (Steps S13, S23, S33, S43, S53, and S63), the detector is applied to a medical image obtained by the obtainer 151, to treat labels corresponding to the output parts or regions as the detection result. In this way, treating labels corresponding to the parts as the detection result enables to detect multiple parts at one time, and thereby, the process can be executed at a higher speed. Also, detectors may be prepared for the respective parts, which may be, for example, a vertebral body detector, an intervertebral disk detector, a sacrum detector, and a second cervical vertebra detector, so as to execute learning and detection for each of the parts. Processing in this way enables to treat each of the detectors as an independent module, and thereby, enables to select a detector(s) appropriate for the image to be processed, and to make the process more flexible. Also, raster scanning that cuts out an image by scanning may be used to provide an image to be input into a detector. The size of a frame of a detection window used for raster scanning may be set to be compatible with the size of the vertebral body, intervertebral disk, or the sacrum; or may be set by a method in which a reference size is set to be changed as a detection window.

Figure 14B:
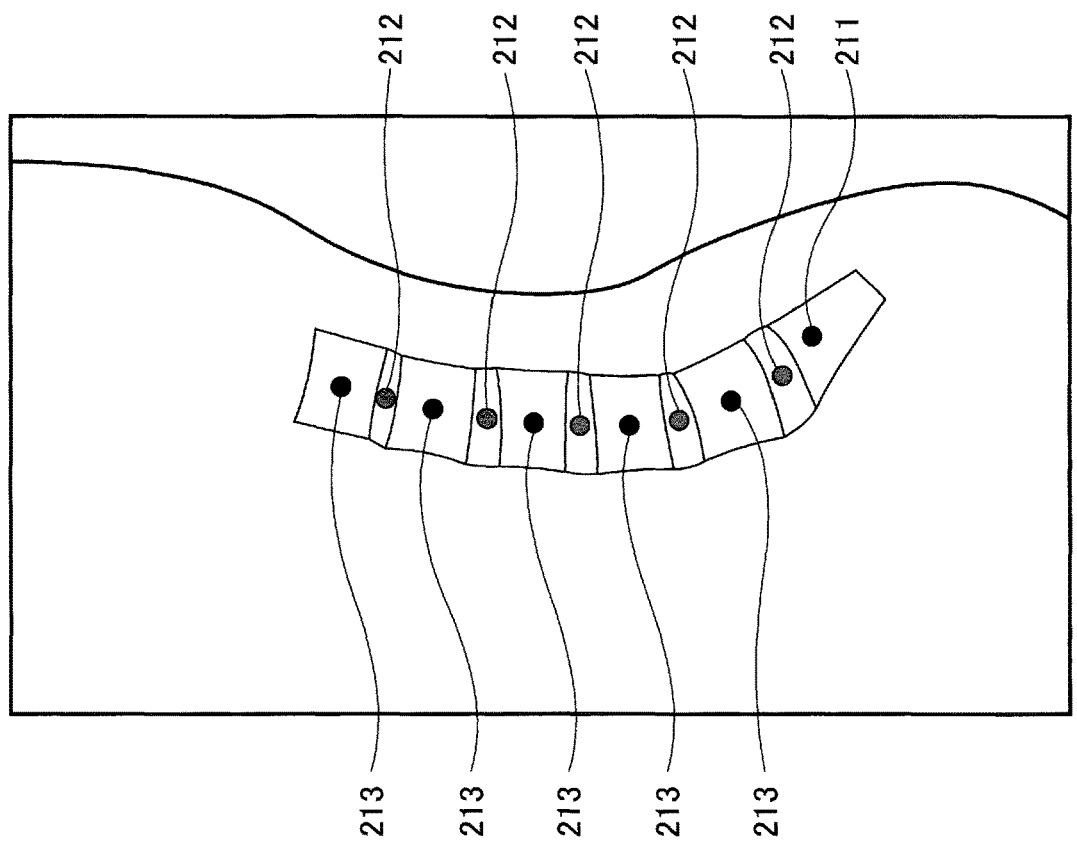
FIG. 14B is a diagram illustrating a content of learning with respect to lumbar vertebrae.
Figure 14A:
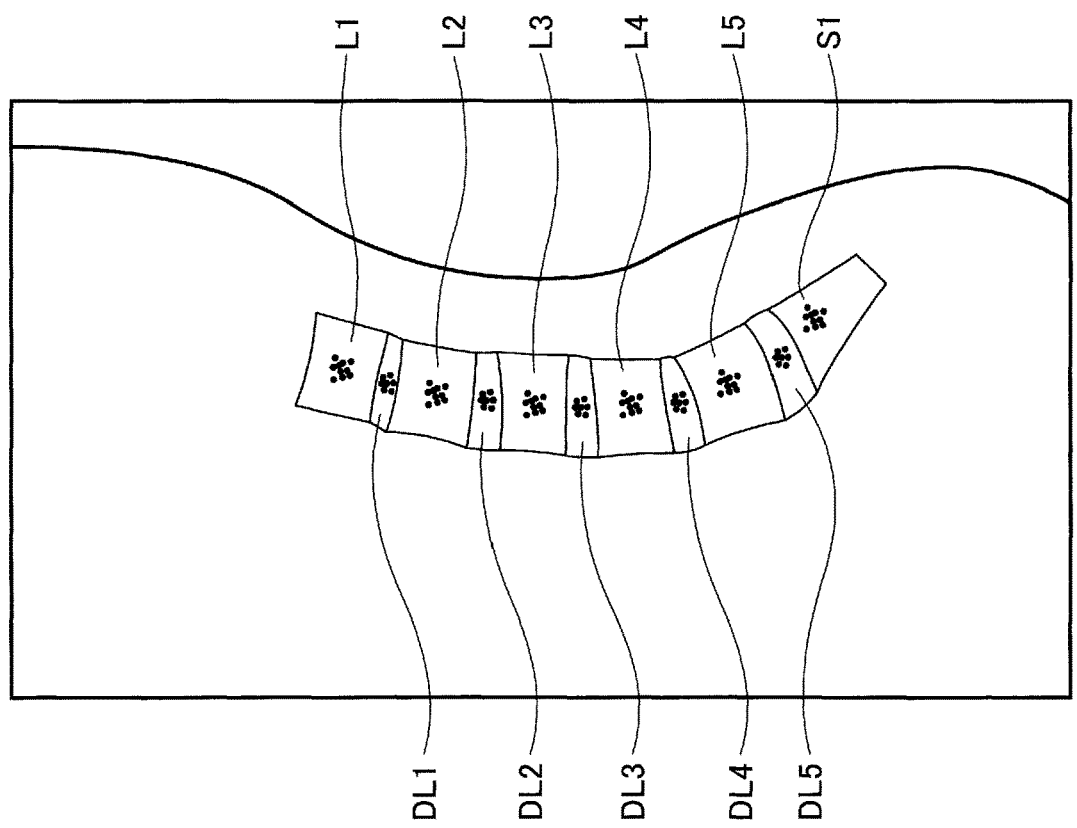
FIG. 14A is a diagram illustrating a content of learning with respect to lumbar vertebrae.
Figure 15A:
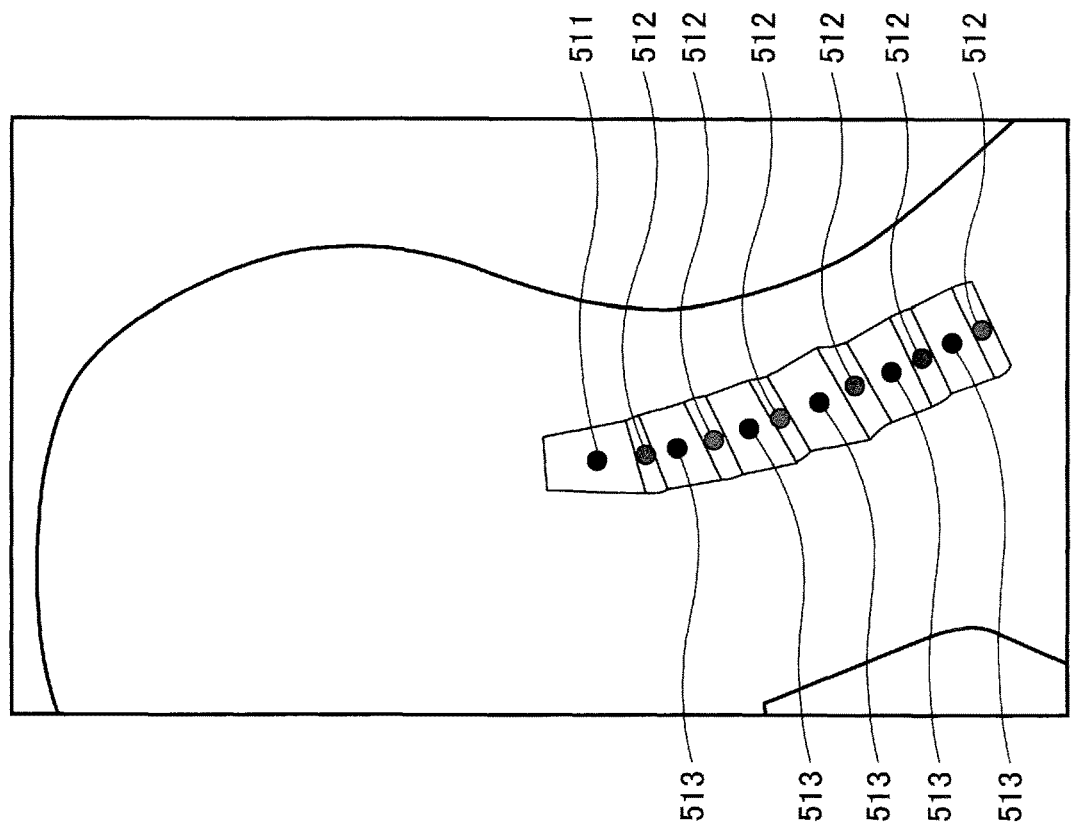
FIG. 15A is a diagram illustrating a content of learning with respect to cervical vertebrae.
Figure 15B:
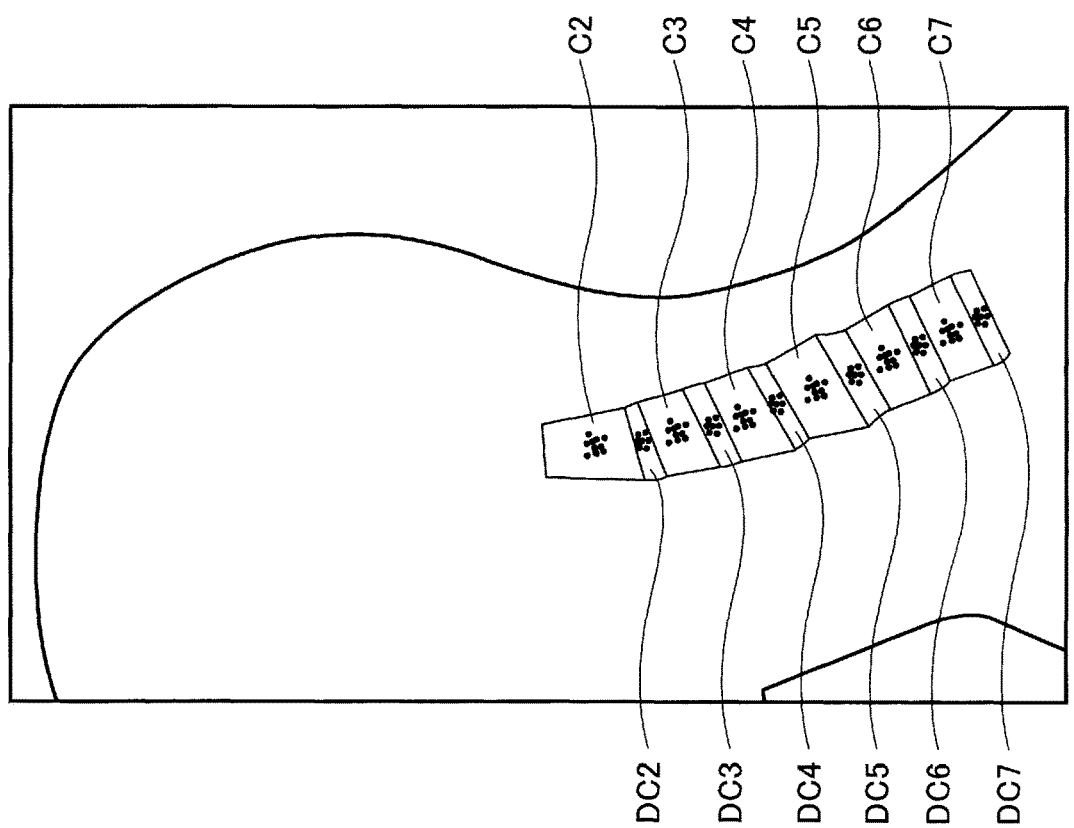
FIG. 15B is a diagram illustrating a content of learning with respect to cervical vertebrae.

Learning of the detector 152 may use CNN (Convolutional Neural Network), SVM (Support Vector Machine), Adaboost, or random forest; or may use Active Shape Model, General Hough Transfer, or Template Matching. These contents are described in, for example, "Vertebra identification using template matching model and K-means clustering", "Fully Automatic Vertebra Detection in X-Ray Images Based on Multi-Class SVM", and "Fast scale-invariant lateral lumbar vertebrae detection and segmentation in X-ray images". Also, false detection removal or isolation point removal using RANSAC (Random sample consensus) may be executed for a detected vertebral body, intervertebral disk, sacrum, or second cervical vertebra. Further, clustering may be executed for multiple detected vertebral bodies, intervertebral disks, sacrums, or second cervical vertebrae, to group the detection points. Also, a cluster obtained after the grouping may be treated as a detection point. FIGS. 14A-14B are diagrams illustrating learned contents of learning of lumbar vertebrae; and FIGS. 15A-15B are diagrams illustrating learned contents of cervical vertebrae. As illustrated in FIG. 14A, clustering may be executed when detection points around the lumbar vertebrae have been detected for each of multiple training data items (images), and as illustrated in FIG. 14B, each cluster obtained after the grouping may be treated as a detection point around the lumbar vertebrae. Also, as illustrated in FIG. 15A, clustering may be executed when detection points around the cervical vertebrae have been detected for each of multiple training data items (images), and as illustrated in FIG. 15B, each cluster obtained after the grouping may be treated as detection points around the cervical vertebrae. Also, as a method of false detection removal using RANSAC, there is a method in which a third-order approximation curve is estimated in consideration of the curvature of the spine, to calculate a distance with the approximate curve as the center, and to remove a detection point whose distance is greater than the distance of half the width of a vertebral body, as a false detection.

According to the embodiments, irrespective of the type of a medical image, it is possible to appropriately label vertebral bodies and intervertebral disks even when the medical image contains unclear vertebral bodies or intervertebral disks. Furthermore, when interpolating an intervertebral disk, not only detection points of the intervertebral disks, but also detection points of the vertebral bodies are used in the medical image. Therefore, compared with the case where interpolation is executed only by using the detection points of the intervertebral disks, the interval between the detection points including the intervertebral disks and the vertebral bodies becomes half to be dense, and thereby, the estimation error of an interpolation point can be reduced. Furthermore, even if the position of an intervertebral disk deviates from the normal position as in the case of a slipped disk, it is possible to interpolate an intervertebral disk with high accuracy from the detection points of vertebral bodies.

Note that even if a medical image does not include a sacrum and a second cervical vertebra, at least one vertebral body or intervertebral disk in the medical image has been known as a specific part of the spine, the detection point may be set as the first reference point to execute labeling. Therefore, for example, it is also possible to execute labeling on a medical image of thoracic vertebrae, which does not include both a sacrum and a second cervical vertebra. Also, it is not necessary for a medical image of cervical vertebrae to include all cervical vertebrae and intervertebral disks; for example, the image may not include a sixth cervical vertebra C6 and a seventh cervical vertebra C7 near the shoulders. Similarly, it is not necessary for a medical image of lumbar vertebrae to include all lumbar vertebrae and intervertebral disks; for example, the image may not include a first lumbar vertebra L1 and a second lumbar vertebra L2 near the ribs. The medical image does not need to be an X-ray image, and may be an MRI image.

The method of interpolation executed by the interpolator 154 is not limited in particular. For example, interpolation may be executed by extrapolation or by interpolation. The interpolation point calculator 171 may use a positional relationship between two parts detected by the detector 152, for example, a positional relationship between a vertebral body and an intervertebral disk, a positional relationship between a sacrum and a vertebral body or an intervertebral disk, a positional relationship between a second cervical vertebra and another vertebral body or an intervertebral disk, to interpolate the position of the vertebral body or intervertebral disk to be interpolated. The positional relationship here includes a relationship between a distance between the two parts or a relationship of an angle formed with any straight line or plane as a reference.

PRIOR ART DOCUMENTS

Patent Documents

[Patent Document 1] Japanese Unexamined Patent Publication No. 2016-168166
[Patent Document 2] Japanese Patent No. 6218569

The present application claims priority under 35 U.S.C. § 119 of Japanese Patent Application No. 2018-015941 filed on Jan. 31, 2018, and Japanese Patent Application No. 2018-111788 filed on Jun. 12, 2018, the entire contents of which are hereby incorporated by reference.

What is claimed is:
1. A medical image processing apparatus, comprising:
a memory; and
at least one processor configured to execute
detecting one or more vertebral bodies and one or more intervertebral disks in a sagittal sectional view of a medical image;
labeling each part satisfying a predetermined condition among the one or more vertebral bodies and the one or more intervertebral disks detected by the detecting;
interpolating a vertebral body or an intervertebral disk in the sagittal sectional view of the medical image in a case where the one or more vertebral bodies and the one or more intervertebral disks detected by the detecting do not include the vertebral body or the intervertebral disk that satisfies the predetermined condition; and
executing the labeling also for the vertebral body or the intervertebral disk interpolated by the interpolating,
wherein the interpolating includes calculating a position of the vertebral body or the intervertebral disk to be interpolated as an interpolation point, by using a position of at least one of the one or more vertebral bodies and the one or more intervertebral disks detected by the detecting.

2. The medical image processing apparatus as claimed in claim 1, wherein the detecting detects a sacrum or a second cervical vertebra in the medical image, and
wherein the labeling determines whether or not the predetermined condition is satisfied with the sacrum or the second cervical vertebra as a reference point.

3. The medical image processing apparatus as claimed in claim 2, wherein the interpolating includes calculating a position of the vertebral body or the intervertebral disk to be interpolated as an interpolation point, by using a position of at least one of the one or more vertebral bodies and the one or more intervertebral disks detected by the detecting.

4. The medical image processing apparatus as claimed in claim 1, wherein the calculating interpolates the position of the vertebral body or the intervertebral disk to be interpolated, by using a positional relationship between two parts among the one or more vertebral bodies and the one or more intervertebral disks detected by the detecting.

5. The medical image processing apparatus as claimed in claim 3, wherein the calculating interpolates the position of the vertebral body or the intervertebral disk to be interpolated, by using a positional relationship between two parts among the one or more vertebral bodies and the one or more intervertebral disks detected by the detecting.

6. The medical image processing apparatus as claimed in claim 1, further comprising:
a display device configured to display a result of the labeling executed by said at least one processor.

7. The medical image processing apparatus as claimed in claim 2, further comprising:
a display device configured to display a result of the labeling executed by said at least one processor.

8. The medical image processing apparatus as claimed in claim 1, further comprising:
a display device configured to display a result of the labeling executed by said at least one processor.

9. The medical image processing apparatus as claimed in claim 3, further comprising:
a display device configured to display a result of the labeling executed by said at least one processor.

10. The medical image processing apparatus as claimed in claim 4, further comprising:
a display device configured to display a result of the labeling executed by said at least one processor.

11. The medical image processing apparatus as claimed in claim 5, further comprising:
a display device configured to display a result of the labeling executed by said at least one processor.

12. A medical image processing method executed by a computer, the method comprising:
detecting one or more vertebral bodies and one or more intervertebral disks in a sagittal sectional view of a medical image;
labeling each part satisfying a predetermined condition among the one or more vertebral bodies and the one or more intervertebral disks detected by the detecting;
interpolating a vertebral body or an intervertebral disk in the sagittal sectional view of the medical image in a case where the one or more vertebral bodies and the one or more intervertebral disks detected by the detecting do not include the vertebral body or the intervertebral disk that satisfies the predetermined condition; and
executing the labeling also for the vertebral body or the intervertebral disk interpolated by the interpolating,
wherein the interpolating includes calculating a position of the vertebral body or the intervertebral disk to be interpolated as an interpolation point, by using a position of at least one of the one or more vertebral bodies and the one or more intervertebral disks detected by the detecting.

13. The method as claimed in claim 12, wherein the detecting detects a sacrum or a second cervical vertebra in the medical image, and
wherein the labeling determines whether or not the predetermined condition is satisfied with the sacrum or the second cervical vertebra as a reference point.

14. A non-transitory computer-readable recording medium having computer readable instructions stored thereon, which when executed, cause a computer to execute a method comprising:
detecting one or more vertebral bodies and one or more intervertebral disks in a sagittal sectional view of a medical image;
labeling each part satisfying a predetermined condition among the one or more vertebral bodies and the one or more intervertebral disks detected by the detecting;
interpolating, a vertebral body or an intervertebral disk in the sagittal sectional view of the medical image in a case where the one or more vertebral bodies and the one or more intervertebral disks detected by the detecting do not include the vertebral body or the intervertebral disk that satisfies the predetermined condition; and
executing the labeling also for the vertebral body or the intervertebral disk interpolated by the interpolating,
wherein the interpolating includes calculating a position of the vertebral body or the intervertebral disk to be interpolated as an interpolation point, by using a position of at least one of the one or more vertebral bodies and the one or more intervertebral disks detected by the detecting.

15. The non-transitory computer-readable recording medium as claimed in claim 14, wherein the detecting detects a sacrum or a second cervical vertebra in the medical image, and
wherein the labeling determines whether or not the predetermined condition is satisfied with the sacrum or the second cervical vertebra as a reference point.

16. A medical image processing system comprising:
a medical image capturing apparatus configured to capture a medical image; and
the medical image processing apparatus as claimed in claim 1 configured to process the medical image.

17. A medical image processing system comprising:
a medical image capturing apparatus configured to capture a medical image; and
the medical image processing apparatus as claimed in claim 2 configured to process the medical image.

18. A medical image processing system comprising:
a medical image capturing apparatus configured to capture a medical image; and
the medical image processing apparatus as claimed in claim 1 configured to process the medical image.

19. A medical image processing system comprising:
a medical image capturing apparatus configured to capture a medical image; and
the medical image processing apparatus as claimed in claim 3 configured to process the medical image.

* * * * *